US006197581B1

(12) United States Patent
Antoni et al.

(10) Patent No.: US 6,197,581 B1
(45) Date of Patent: Mar. 6, 2001

(54) HUMAN ADENYLATE CYCLASE AND USE THEREFOR

(75) Inventors: Ferenc Antoni; Janice M Paterson, both of Edinburgh (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 09/398,193

(22) Filed: Sep. 17, 1999

Related U.S. Application Data

(63) Continuation-in-part of application No. 08/894,173, filed as application No. PCT/GB96/00312 on Feb. 14, 1996, now Pat. No. 6,090,612.

(30) Foreign Application Priority Data

Feb. 14, 1995 (GB) .................................................. 9502806
Aug. 11, 1995 (GB) .................................................. 9516528

(51) Int. Cl.[7] .............................. C12N 5/10; C12N 5/00; C12N 1/20; C12N 15/00; C07H 21/04
(52) U.S. Cl. ................. 435/325; 435/252.3; 435/252.33; 435/320.1; 435/369; 536/23.2
(58) Field of Search ................................. 435/320.1, 232, 435/369, 252.3, 252.33, 325; 536/23.2

(56) References Cited

PUBLICATIONS

Hacker et al. (May 15, 1998) Genomics, vol.50, pp. 97–104.*
Antoni et al., Ca2+/calcineurin inhibition of adenylyl cyclase in mouse anterior pituitary corticotroph tumor cells, J. Physiol, vol. 475P, 1994, pp. 137P–138P.
Shipston et al., Glucocorticoid Negative Feedback in Pituitary Corticotropes, Annals NY Academy of Sciences, vol. 746, Nov. 30, 1994, pp. 453–455.
Paterson et al., Control of a Novel Adenlyl Cyclase by Calcineurin, Biochemical & Biophysical Resrch Communications, vol. 214, No. 3, Sep. 25, 1995, pp. 1000–1008.

Antoni et al., Calcineurin Feedback Inhibition of Agonist–evoked cAMP Formation, Journal of Biological Chemistry, vol. 270, No. 47, Nov. 24, 1995, pp. 28055–28061.
Krupinski et al., Molecular Diversity in the Adenylylcyclase Family, Journal of Biological Chemistry, vol. 267, No. 34, Dec. 5, 1992, pp. 24858–24862.
Premont et al., Two members of a widely expressed subfamily of hormone–stimulated adenylyl cyclases, Proc. Natl. Acad. Sci., vol. 89, Dec. 1992, pp. 9809–9813.
Premont, Identification of Adenylyl Cyclases by Amplification Using Degenerate Primers, Methods in Enzymology, vol. 238, pp. 116–127.
Kerwin et al., Adenylate Cyclase Subtypes as Molecular Drug Targets, Annual Reports in Medicinal Chemistry, Chapter 29, pp. 287–295.
Comparison Table of Xenopus Laevis Adenyl cyclase RNA (top sequence) compared to mRNA of the invention. (Xenopus sequence obtained from publicly available database.).
Pieroni et al., Signal Recognition and Integration by Gs–Stimulated Adenylyl Cyclases, Current Opinion in Neurobiology (1993), vol. 3, pp. 344–351.
Antoni et al., "Molecular cloning and expression of an adenylyl cyclose from xenopus laevis oocytes", of Biological Chemistry, vol. 271, Jul. 21, 1997, p 28060, Acession No. Z46958.

* cited by examiner

*Primary Examiner*—Elizabeth Slobodyansky
(74) *Attorney, Agent, or Firm*—Ratner & Prestia

(57) ABSTRACT

There is provided a novel adenylate cyclase enzyme, the nucleotide sequence of which is set out in SEQ ID NO: 98. The activity of the adenylate cyclase is uniquely regulated by calcineurin, a protein phosphatase. The calcineurin binding site has been identified at amino acids 503 to 610 of the novel adenylate cyclase.

Figure 1:
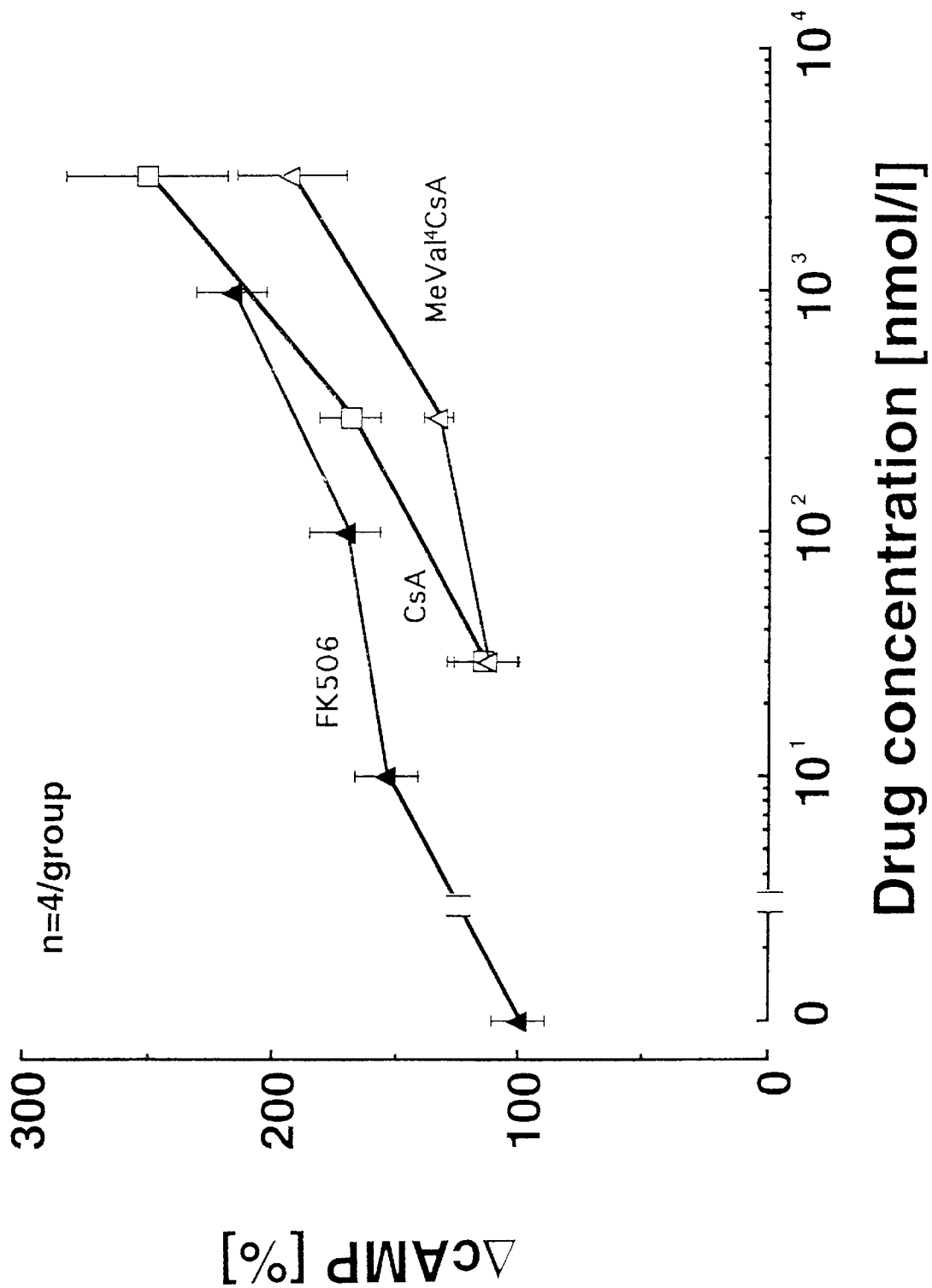

Regulation of the novel adenylate cycalse may be useful in treating certain disorders. Suitable regulators include agents which bind to the 503–610 amino acid site and include calcineurin, its activators, inhibitors and competitors and antibodies specific to that site. Specific disorders include neurological disorders such as Parkinsons' disease, cardiovascular disorders such as angina pectoris and tumors, especially ovarian tumors.

5 Claims, 26 Drawing Sheets

FIGURE 2
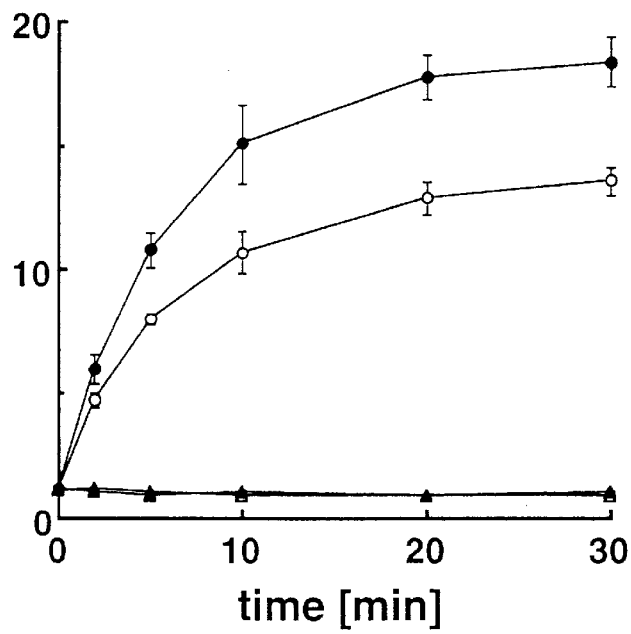
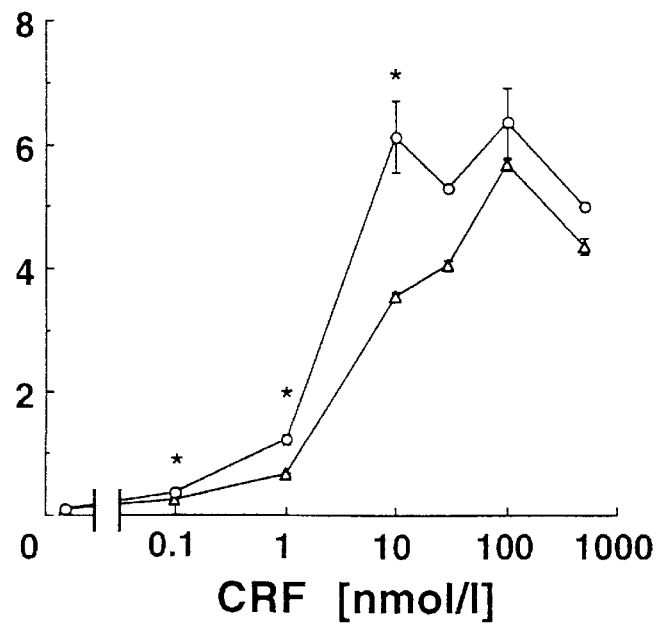

FIGURE 8

```
                 1306                                                    1356
hum7         KIKTIGSTYM  AAAGLSV...  .....ASGHEN  .QELERQHAH  IGVMVEFSIA
mmu12919     KIKTIGSTYM  AAAGLSA...  .....PSGHEN  .QDLERKHVH  IGVLVEFSMA
cya2_rat     KIKTIGSTYM  AATGLSA...  .....IPSQEH  AQEPERQYMH  IGTMVEFAYA
cya4_rat     KIKTIGSTYM  AATGLNA...  .....TPGQDT  QQDAERSCSH  LGTMVEFAVA
hsadencyr8   KIKTIGSTYM  AVSGLS....  ......PE...  KQQCEDKWGH  LCALADFSLA
ratacviii    KIKTIGSTYM  AVSGLS....  ......PE...  KQQCEDKWGH  LCALADFSLA
a46187       KIKTIGSTYM  AASGLN....  ......AS...  TYD.QVGRSH  ITALADYAMR
cya6_mouse   KIKTIGSTYM  AASGLN....  ......AS...  TYD.QVGRSH  ITALADYAMR
a49201       KIKTIGSTYM  AASGLN....  ......AS...  TYD.QVGRSH  ITALADYAMR
cya6_rat     KIKTIGSTYM  AASGLN....  ......AS...  TYD.QVGRSH  ITALADYAMR
cya6_canfa   KIKTIGSTYM  AASGLN....  ......AS...  TYD.QAGRSH  ITALADYAMR
s29717       KIKTIGSTYM  AASGLN....  ......DS...  TYD.KAGKTH  IKALADFAMK
ocmradcyv    KIKTIGSTYM  AASGLN....  ......DS...  TYD.KVGKTH  IKALADFAMK
cya5_canfa   KIKTIGSTYM  AASGLN....  ......DS...  TYD.KVGKTH  IKALADFAMK
cya1_bovin   KIKTIGSTYM  AAVGLAP...  .....TAG...  TKAKKCISSH  LSTLADFAIE
cya3_rat     KIKTIGSTYM  AASGVTPDVN  TNGFTSSSKE   EKSDKERWQH  LADLADFALA
AC           KIKTIGATYM  AASGLN....  .....TAQ...  CQEGGHPQEH  LRILFEFAKE
             ................  ..-   -.--o---.  .oo.o...-.

1357                                                    1405
hum7         LMSKLDGINR  HSFN.SFRLR  VGINHGPVIA  GVIGARKPQY  DIWGNTVNV
mmu12919     LMSKLDGINR  HSFN.SFRLR  VGINHGPVIA  GVIGARKPQY  DIWGNTVNV
cya2_rat     LVGKLDAINK  HSFN.DFKLR  VGINHGPVIA  GVIGAQKPQY  DIWGNTVNV
cya4_rat     LGSKLGVINK  HSFN.NFRLR  VGLNHGPVVA  GVIGAQKPQY  DIWGNTVNV
hsadencyr8   LTESIQEINK  HSFN.NFELR  IGISHGSVVA  GVIGAKKPQY  DIWGKTVNL
ratacviii    LTESIQEINK  HSFN.NFELR  IGISHGSVVA  GVIGAKKPQY  DIWGKTVNL
a46187       LMEQMKHINE  HSFN.NFQMK  IGLNMGPVVA  GVIGARKPQY  DIWGNTVNV
cya6_mouse   LMEQMKHINE  HSFN.NFQMK  IGLNMGPVVA  GVIGARKPQY  DIWGNTVNV
a49201       LMEQMKHINE  HSFN.NFQMK  IGLNMGPVVA  GVIGARKPQY  DIWGNTVNV
cya6_rat     LMEQMKHINE  HSFN.NFQMK  IGLNMGPVVA  GVIGARKPQY  DIWGNTVNV
cya6_canfa   LMEQMKHINE  HSFN.NFQMK  IGLNMGPVVA  GVIGARKPQY  DIWGNTVNV
s29717       LMDQMKYINE  HSFN.NFQMK  IGLNIGPVVA  GVIGARKPQY  DIWGNTVNV
ocmradcyv    LMDQMKYINE  HSFN.NFQMK  IGLNIGPVVA  GVIGARKPQY  DIWGNTVNV
cya5_canfa   LMDQMKYINE  HSFN.NFQMK  IGLNIGPVVA  GVIGARKPQY  DIWGNTVNV
cya1_bovin   MFDVLDEINY  QSYN.DFVLR  VGINVGPVVA  GVIGARRPQY  DIWGNTVNV
cya3_rat     MKDTLTNINN  QSFN.NFMLR  IGMNKGGVLA  GVIGARKPHY  DIWGNTVNV
AC           MMRVVDDFNN  NMLWFNFKLR  VGFNHGPLTA  GVIGTTKLLY  DIWGDTVNI
             ....o.oo..  o-o--....  ..---o-.  ........  ........o
```

```
AC      503.......+.........+.........+.........+.........+.........+ 550.......+
musAC        RFKFDVWSNDVNLANLMEQLGVAGKVHISEATAKYLDDRYEMEDGRVIERLGQSVVAD..NSFLKT
bovActp1     KWQYDVWSNDVTLANVMEAAGLPGKVHITKTTLACLNGDYEVEPGHGHER..NSFLKT
ratActp3     RWQYDVWSTDVTVANKMEAGGIPGRVHISQSTMDCLKGEFDVEPGDGGSR..CDYLDE
ratActp8     KWQFDVWSWDVDIANKLESGGIPGRIHISKATLDCLSGDYNVEEGHGKER..NEFLRK
ratActp5     KWQFDVWSNDVTLANHMEAGGKAGRIHITKATLNYLNGDYEVEPGCGGER..NAYLKE
ratActp6     KWQFDVWSNDVTLANHMEAGGRAGRIHITRATLQYLNGDYEVEPGRGGER..NGYLKE
ratActp2     KWQYDVWSHDVTLANHMEAGGVPGRVHISSVTLEHLNGAYKVEEGDGEIR..DPYLKQ
ratActp4     KNQYDVNSHDVTLANHMEAGGVPGRVHITGATLALLAGAVAVERADMEHR..DPYLRE
musActp7     KWQYDVWSHDVSLANRMEAAGVPGRVHITEATLNHLDKAYEVEDGHGEQR..DPYLKE
humACtp7     KWQYDVWSHDVSLANRMEAAGVPGRVHITEATLKHLDKAYEVEDGHGQQR..DPYLKE 561.......+.........+.........+.........+.........+.........+ 600.......+
musAC        QLKGLKTYLISGQRAKESHCSCAEALLSGFEVIDDSRESSGPRGQGTASP
bovActp1     H..NIETFFIVPSHRRKIFPGLILSDIKPAKRMKFKTVCYLLVQLMYHCR
ratActp3     K..GIETYLIIASKPEVKKTAQNGLNGSALPNGAPASKPSSSPALIETKE
ratActp8     H..NIETYLIKQPEESLLSLPEDIVKESVSCSDRRNSGATFTEGSWSPEL
ratActp5     H..SIETFLILRCTQKREEKAMIAKMNRQRTNSIGHNPPHWGAERPFYN
ratActp6     Q..CIETFLILGASQKRKEEKAMLVKLQRTRANSMEGLMPHWGAERPFYN
ratActp2     H..LVKTYFVINPKGERRSPQ..HLFRPRHTLDGAKMRASVRMTRYLSWG
ratActp4     L..GEPTYLVIDPWAEEEDEKGTERGLLS.SLEGHTMRPSLLMTRYLSWG
musActp7     M..NIRTYLVIDPRSQQPPPSHHLSKPKGDATL.KMRASVRVTRYLSWG
humACtp7     M..NIRTYLVIDPRSQQPPPPSQHLPRPKGDAAL.KMRASVRMTRYLSWG
```

Fig. 12C

1.  TGRVLCGVLGLRKWQYDVWSNDVTL--ANVMEAAGLPGKVHITKTT-LACLNGDYEVEPGH--GHERNSFLKTHNIETFF
2.  ANKMEAAGGIPGRVHISQSTMDCLKGEFDVEPGDGGSRCDYLDEKGIETYLIIASKPEVKKTAQNGLNGSALPNGAPASK
3.  ANKLESGGIPGRIHISKATLDCLSGDYNVEEGHGKERNEFLRKHNIETYLIKQPEESLLSLPEDIVKESVSCSDRRNS-
4.  ANHMESGGEPGRVHVTRA-T-DSLSGEY-EVEAGHGDERSSYLRDHGVDTFFI-VPPPHRRKPLMLNTLGVRSAIGSRR

5.  KWQFDVWS-NDVTLANHMEAGGKAGRIHITKATL-NYLNGDYEVEPGCGGERNAYLKEHSIETFLILRCTQKRKEEKAM
6.  GMDMIEAISLVREVTGVNVNMRVGIH-SGRVHCGVLGLRKWQFDVWSNDVTLANHMEAGGKAGRIHITKATLSYLNGDY
7.  KWQFDVWS-NDVTLANHMEAGGKAGRIHITKATLQYLN-GDYEVEPGRGGERNAYLKEQHIETFLILGASQKRKEEKAML
8.  RFKFDVWSN-DVNLANLMEQLGVAGKVHISEATAKYLDDRYEMEDGRVIERLG-QSVVADQLKGLKTYLISGQRAKESH

9.  KWQYDVWS-HDVTLANHMEAGGVPGRVHISSVTLEHLNGAYK-VEEGDGEIRDPYLKQHLVKTYFV-INPKGERRSPQH
10 KWQYDVWSH-DVTLANHMEAGGVPGRVHITGATLALLAGAY-AVERADMEHRDPYLRELGEPTYLVIDPWAEEEDEKGT
11 KWQYDVWSH-DVSLANRMEAAGVPGRVHITEATLNHLDKAYEVEDGHGEQRDPYLKEMN-IRTYLV-IDPRSQQPPPPS

Fig. 16A

1.  IVPSHRRKIFPGLIISDIKPAKRMKFKTVCYLIVQ
2.  PSSPALIETKEPNGSA--HASGSTSEEAEEQE
3.  GATFTEGSWSPEL------PFDNIVGKQN
4.  KLSFR-NVSNVVMQLLHTIKF-SEPVPF

5.  IAKMNRQRTNSIGHN----PPHWGAERPFYNHLGGN
6.  EVEPGC-GGERNAYLKEHSIETFLILRCTQKRVRGGGGPRPG
7.  AKLQRTRANSMEGLMPRWVPDRAFSRTKDSKAFRQM
8.  CSCAEALL-GFE-VIDDS-RESSGPRGQGTAS

9.  LFRPRHTLDGAKMRASVRMTRY-LESWGAAKPFA
10. ERGLLSSLE GHTMRPSLLMTR-YLESWGAAKPF
11. HHLSKPKGDK-ATLKMRASVRVTRYLESWGAARPFAHLN

Fig. 16B

FIGURE 21
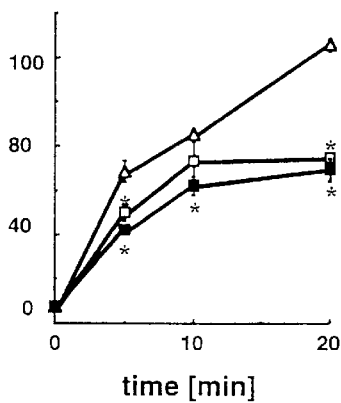
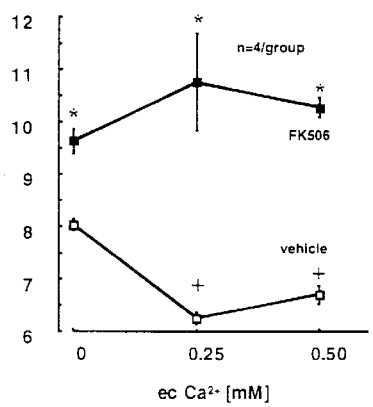
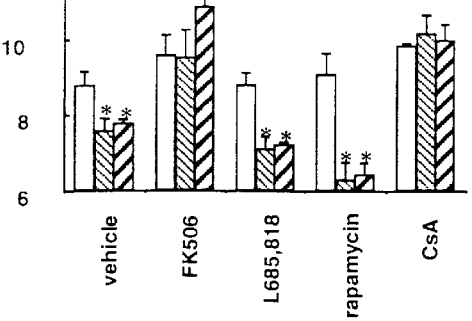

Fig. 22

SEQUENCE LISTING

<160> NUMBER OF SEQ ID NOS: 104

<210> SEQ ID NO 1
<211> LENGTH: 4473
<212> TYPE: DNA
<213> ORGANISM: Mouse
<220> FEATURE:
<221> NAME/KEY: CDS
<222> LOCATION: (43)..(4101)
<223> OTHER INFORMATION: PRODUCT = "Adenylate cyclase coding region"
<220> FEATURE:
<223> OTHER INFORMATION: ANTI-SENSE : NO
<220> FEATURE:
<223> OTHER INFORMATION: CELL TYPE :  Corticotroph tumour cell line
<220> FEATURE:
<223> OTHER INFORMATION: CELL LINE : AtT20
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : cDNA
<220> FEATURE:
<223> OTHER INFORMATION: HYPOTHETICAL : NO

<400> SEQUENCE: 1

```
tgcccctgac ctggtcggga aaggttccaa gagctcggca ac atg gct tcc tca         54
                                               Met Ala Ser Ser
                                                 1 ccc cac cag cag ctg ctg cat cac cat agc acc gag gtg agc tgc gac        102
Pro His Gln Gln Leu Leu His His His Ser Thr Glu Val Ser Cys Asp
  5                  10                  15                  20 tca agc gga gac agc aac agc gtg agg gtc aag atc aac cct aag cag       150
Ser Ser Gly Asp Ser Asn Ser Val Arg Val Lys Ile Asn Pro Lys Gln
                 25                  30                  35 ctg tcc tcc aac acc cac ccg aag cac tgc aag tac agc atc tcc tcc       198
Leu Ser Ser Asn Thr His Pro Lys His Cys Lys Tyr Ser Ile Ser Ser
             40                  45                  50 agc tgt agc agc tcg gga gac tca ggg ggc ctt ccc cgg agg gtt ggc       246
Ser Cys Ser Ser Ser Gly Asp Ser Gly Gly Leu Pro Arg Arg Val Gly
         55                  60                  65 ggc ggg ggt cgc ctg cgc aga cag aag aag ctg ccc cag ctt ttt gag       294
Gly Gly Gly Arg Leu Arg Arg Gln Lys Lys Leu Pro Gln Leu Phe Glu
     70                  75                  80 agg gcc tcc agc cgg tgg tgg gac ccc aaa ttc gac tcc atg aac ctg       342
Arg Ala Ser Ser Arg Trp Trp Asp Pro Lys Phe Asp Ser Met Asn Leu
 85                  90                  95                 100 gag gag gcc tgc ctg gag cgc tgc ttt ccg cag acc cag cgc cgc ttc       390
Glu Glu Ala Cys Leu Glu Arg Cys Phe Pro Gln Thr Gln Arg Arg Phe
                105                 110                 115 cgg tac gca ctc ttt tat gtg ggc ttc gcc tgc ctt ctc tgg agc atc       438
Arg Tyr Ala Leu Phe Tyr Val Gly Phe Ala Cys Leu Leu Trp Ser Ile
            120                 125                 130 tat ttc gct gtc cac atg aaa tcc aaa gtg att gtc atg gtg gtc cca       486
Tyr Phe Ala Val His Met Lys Ser Lys Val Ile Val Met Val Val Pro
        135                 140                 145 gct ctg tgc ttc ctg gtg gtg tgt gtg ggc ttt ttc ctg ttt act ttc       534
Ala Leu Cys Phe Leu Val Val Cys Val Gly Phe Phe Leu Phe Thr Phe
    150                 155                 160 acc aag ctg tac gcc cgg cat tat gcg tgg acc tcg ctg gct ctc acc       582
Thr Lys Leu Tyr Ala Arg His Tyr Ala Trp Thr Ser Leu Ala Leu Thr
165                 170                 175                 180 ctg ctg gtg ttc gcc ctg acc ctg gct gcg cag ttt cag gtt tgg aca       630
```

```
                    Leu Leu Val Phe Ala Leu Thr Leu Ala Ala Gln Phe Gln Val Trp Thr
                                    185                 190                 195 cct ctg tca gga cgt gtt gac agc tcc aat cat act ctc acg gcc act            678
Pro Leu Ser Gly Arg Val Asp Ser Ser Asn His Thr Leu Thr Ala Thr
            200                 205                 210 ccg gcg gac act tgc tta tct caa gta gga agc ttc tcc ata tgc atc            726
Pro Ala Asp Thr Cys Leu Ser Gln Val Gly Ser Phe Ser Ile Cys Ile
            215                 220                 225 gaa gtg ctc ctt ttg ctc tac aca gtc atg cag tta cct ctg tac ctg            774
Glu Val Leu Leu Leu Leu Tyr Thr Val Met Gln Leu Pro Leu Tyr Leu
        230                 235                 240 agc ttg ttt ttg ggg gtg gtc tat tct gtc ctt ttt gag acc ttc ggc            822
Ser Leu Phe Leu Gly Val Val Tyr Ser Val Leu Phe Glu Thr Phe Gly
245                 250                 255                 260 tac cac ttc cga aac gaa gac tgc tac cct tct ccg ggc cct ggg gcc            870
Tyr His Phe Arg Asn Glu Asp Cys Tyr Pro Ser Pro Gly Pro Gly Ala
                265                 270                 275 ctg cac tgg gag ctg ctg agc aga gcc ctg ctt cac gtg tgc att cac            918
Leu His Trp Glu Leu Leu Ser Arg Ala Leu Leu His Val Cys Ile His
            280                 285                 290 gct atc ggg atc cat ctg ttt gtc atg tct cag gtg agg tcc agg agc            966
Ala Ile Gly Ile His Leu Phe Val Met Ser Gln Val Arg Ser Arg Ser
            295                 300                 305 acc ttt ctc aag gtg gga caa tcc att atg cac ggc aaa gat ctg gaa           1014
Thr Phe Leu Lys Val Gly Gln Ser Ile Met His Gly Lys Asp Leu Glu
        310                 315                 320 gta gag aaa gcc ctg aaa gag agg atg att cat tca gtg atg cca aga           1062
Val Glu Lys Ala Leu Lys Glu Arg Met Ile His Ser Val Met Pro Arg
325                 330                 335                 340 atc ata gcc gac gac tta atg aaa caa ggg gac gag gag agt gag aat           1110
Ile Ile Ala Asp Asp Leu Met Lys Gln Gly Asp Glu Glu Ser Glu Asn
                345                 350                 355 tct gtc aag agg cat gcc acc tcc agt ccc aag aac agg aag aag aag           1158
Ser Val Lys Arg His Ala Thr Ser Ser Pro Lys Asn Arg Lys Lys Lys
            360                 365                 370 tcc tcc ata cag aag gca ccg ata gca ttc cgc ccc ttt aag atg cag           1206
Ser Ser Ile Gln Lys Ala Pro Ile Ala Phe Arg Pro Phe Lys Met Gln
        375                 380                 385 cag att gaa gaa gtc agt att tta ttt gca gac att gtg ggt ttc acc           1254
Gln Ile Glu Glu Val Ser Ile Leu Phe Ala Asp Ile Val Gly Phe Thr
390                 395                 400 aag atg agc gcc aac aaa tct gcg cat gcc ttg gta ggc cta ctc aat           1302
Lys Met Ser Ala Asn Lys Ser Ala His Ala Leu Val Gly Leu Leu Asn
405                 410                 415                 420 gac ctg ttc ggt cgc ttt gac cgc ctg tgt gag cag acc aag tgt gag           1350
Asp Leu Phe Gly Arg Phe Asp Arg Leu Cys Glu Gln Thr Lys Cys Glu
                425                 430                 435 aag atc agc act ctg ggg gac tgt tat tac tgt gtg gca ggg tgt ccg           1398
Lys Ile Ser Thr Leu Gly Asp Cys Tyr Tyr Cys Val Ala Gly Cys Pro
            440                 445                 450 gag ccc cgg gca gac cat gcc tac tgc tgc att gaa atg ggc tta ggc           1446
Glu Pro Arg Ala Asp His Ala Tyr Cys Cys Ile Glu Met Gly Leu Gly
        455                 460                 465 atg ata aaa gcc atc gag cag ttc tgc cag gag aag aaa gag atg gtg           1494
Met Ile Lys Ala Ile Glu Gln Phe Cys Gln Glu Lys Lys Glu Met Val
470                 475                 480 aac atg cgt gtt ggg gtt cac acg ggg act gtc ctg tgt ggc atc ctg           1542
Asn Met Arg Val Gly Val His Thr Gly Thr Val Leu Cys Gly Ile Leu
485                 490                 495                 500
```

-continued

| | |
|---|---|
| ggc atg agg agg ttt aaa ttt gat gtg tgg tcc aac gat gtg aac ttg<br>Gly Met Arg Arg Phe Lys Phe Asp Val Trp Ser Asn Asp Val Asn Leu<br>505 510 515 | 1590 |
| gct aat ctc atg gag cag ctg gga gtg gct ggc aaa gtt cac ata tct<br>Ala Asn Leu Met Glu Gln Leu Gly Val Ala Gly Lys Val His Ile Ser<br>520 525 530 | 1638 |
| gag gcc act gca aaa tac tta gac gac agg tat gaa atg gaa gat ggg<br>Glu Ala Thr Ala Lys Tyr Leu Asp Asp Arg Tyr Glu Met Glu Asp Gly<br>535 540 545 | 1686 |
| aga gtt att gag cgc ctt ggg cag agt gtg gtg gct gac cag ttg aaa<br>Arg Val Ile Glu Arg Leu Gly Gln Ser Val Val Ala Asp Gln Leu Lys<br>550 555 560 | 1734 |
| ggt ttg aag aca tac ctg ata tcg ggt cag aga gcc aag gag tcc cac<br>Gly Leu Lys Thr Tyr Leu Ile Ser Gly Gln Arg Ala Lys Glu Ser His<br>565 570 575 580 | 1782 |
| tgc agc tgt gca gag gcc ctg ctt tct ggc ttt gag gtc att gac gac<br>Cys Ser Cys Ala Glu Ala Leu Leu Ser Gly Phe Glu Val Ile Asp Asp<br>585 590 595 | 1830 |
| tca cgg gag tcc tca ggc cct agg gga cag ggg aca gca tcg cca ggg<br>Ser Arg Glu Ser Ser Gly Pro Arg Gly Gln Gly Thr Ala Ser Pro Gly<br>600 605 610 | 1878 |
| agt gtc agt gat ttg gcg cag act gtc aaa acc ttt gat aac ctt aag<br>Ser Val Ser Asp Leu Ala Gln Thr Val Lys Thr Phe Asp Asn Leu Lys<br>615 620 625 | 1926 |
| act tgc cct tct tgt gga atc aca ttt gct ccc aaa tct gaa gct ggt<br>Thr Cys Pro Ser Cys Gly Ile Thr Phe Ala Pro Lys Ser Glu Ala Gly<br>630 635 640 | 1974 |
| gca gaa gga gga act gtg caa aat ggc tgt caa gac gag cct aag acc<br>Ala Glu Gly Gly Thr Val Gln Asn Gly Cys Gln Asp Glu Pro Lys Thr<br>645 650 655 660 | 2022 |
| agc acc aag gct tct gga gga ccc aac tcc aaa acc cag aat gga ctt<br>Ser Thr Lys Ala Ser Gly Gly Pro Asn Ser Lys Thr Gln Asn Gly Leu<br>665 670 675 | 2070 |
| ctg agc cct cct gca gag gag aag ctc act aac agc cag acc tcc ctc<br>Leu Ser Pro Pro Ala Glu Glu Lys Leu Thr Asn Ser Gln Thr Ser Leu<br>680 685 690 | 2118 |
| tgt gag atc ctg caa gag aag gga cgg tgg gca ggc gtg agc ttg gac<br>Cys Glu Ile Leu Gln Glu Lys Gly Arg Trp Ala Gly Val Ser Leu Asp<br>695 700 705 | 2166 |
| cag tca gcc ctc ctc ccg ctc agg ttc aag aac atc cgt gag aaa act<br>Gln Ser Ala Leu Leu Pro Leu Arg Phe Lys Asn Ile Arg Glu Lys Thr<br>710 715 720 | 2214 |
| gat gcc cac ttt gtt gat gtc atc aaa gaa gac agc ctg atg aaa gat<br>Asp Ala His Phe Val Asp Val Ile Lys Glu Asp Ser Leu Met Lys Asp<br>725 730 735 740 | 2262 |
| tat ttc ttc aag ccg ccc atc aat cag ttc agc ctg aac ttc ctg gac<br>Tyr Phe Phe Lys Pro Pro Ile Asn Gln Phe Ser Leu Asn Phe Leu Asp<br>745 750 755 | 2310 |
| cag gag ctg gag cga tca tat aga acc agc tac cag gaa gag gtc ata<br>Gln Glu Leu Glu Arg Ser Tyr Arg Thr Ser Tyr Gln Glu Glu Val Ile<br>760 765 770 | 2358 |
| aag aat tct cct gtg aag acg ttc gcc agt gcc acc ttc agc tcc ctt<br>Lys Asn Ser Pro Val Lys Thr Phe Ala Ser Ala Thr Phe Ser Ser Leu<br>775 780 785 | 2406 |
| ctg gat gtg ttt ctg tca acc acc gtg ttc ctg att ctc tcc atc acc<br>Leu Asp Val Phe Leu Ser Thr Thr Val Phe Leu Ile Leu Ser Ile Thr<br>790 795 800 | 2454 |
| tgc ttc cta aag tat gga gcc acc gcc acc cct ccc cca ccg gct gcc<br>Cys Phe Leu Lys Tyr Gly Ala Thr Ala Thr Pro Pro Pro Pro Ala Ala<br>805 810 815 820 | 2502 |

```
ctg gcc gtc ttt ggt gca gac ctg ctg ctg gag gtg ctt tcc ctc ata      2550
Leu Ala Val Phe Gly Ala Asp Leu Leu Leu Glu Val Leu Ser Leu Ile
             825                 830                 835 gtg tcc atc aga atg gtg ttt ttc cta gag gat gtc atg aca tgc aca      2598
Val Ser Ile Arg Met Val Phe Phe Leu Glu Asp Val Met Thr Cys Thr
         840                 845                 850 aag tgg ttg ctg gaa tgg atc gct ggc tgg ctc cct cgc cac tgc att      2646
Lys Trp Leu Leu Glu Trp Ile Ala Gly Trp Leu Pro Arg His Cys Ile
     855                 860                 865 ggg gca atc ttg gtg tct ctt cct gcc ctg gct gtc tat tca cac atc      2694
Gly Ala Ile Leu Val Ser Leu Pro Ala Leu Ala Val Tyr Ser His Ile
 870                 875                 880 acc tct gag ttt gag acc aac ata cat gtc acc atg ttc act ggc tct      2742
Thr Ser Glu Phe Glu Thr Asn Ile His Val Thr Met Phe Thr Gly Ser
885                 890                 895                 900 gcg gtg ctg gtg gcc gtt gtg cac tac tgt aac ttc tgc cag ctc agc      2790
Ala Val Leu Val Ala Val Val His Tyr Cys Asn Phe Cys Gln Leu Ser
             905                 910                 915 tcc tgg atg agg tcc tcc ctt gcc acc atc gtg ggg gct ggg ctg ctg      2838
Ser Trp Met Arg Ser Ser Leu Ala Thr Ile Val Gly Ala Gly Leu Leu
         920                 925                 930 ctt ctg ctc cac atc tcc ctg tgt cag gac agt tcc att gtg atg tcc      2886
Leu Leu Leu His Ile Ser Leu Cys Gln Asp Ser Ser Ile Val Met Ser
     935                 940                 945 ccc ttg gac tca gca cag aat ttc agt gcc cag agg aac cca tgc aac      2934
Pro Leu Asp Ser Ala Gln Asn Phe Ser Ala Gln Arg Asn Pro Cys Asn
 950                 955                 960 agc tca gtg ctg cag gac ggc agg agg ccg gcc agc ctc ata ggc aag      2982
Ser Ser Val Leu Gln Asp Gly Arg Arg Pro Ala Ser Leu Ile Gly Lys
965                 970                 975                 980 gag ctt atc ctc acc ttc ttc ctc ctg ctc ctt gtc tgg ttc ctg          3030
Glu Leu Ile Leu Thr Phe Phe Leu Leu Leu Leu Val Trp Phe Leu
             985                 990                 995 aac cgg gag ttc gag gtc agc tac cgg ctg cac tac cat ggg gat gtg      3078
Asn Arg Glu Phe Glu Val Ser Tyr Arg Leu His Tyr His Gly Asp Val
         1000                1005                1010 gag gcc gac cta cac cgc acc aag atc cag agc atg aga gac cag gct      3126
Glu Ala Asp Leu His Arg Thr Lys Ile Gln Ser Met Arg Asp Gln Ala
     1015                1020                1025 gac tgg cta ctg cgg aac atc atc ccc tac cat gtg gct gag cag ctc      3174
Asp Trp Leu Leu Arg Asn Ile Ile Pro Tyr His Val Ala Glu Gln Leu
 1030                1035                1040 aag gtc tct cag acc tac tcc aag aac cat gac agc ggg gga gtc atc      3222
Lys Val Ser Gln Thr Tyr Ser Lys Asn His Asp Ser Gly Gly Val Ile
1045                1050                1055                1060 ttt gcc agc att gtc aac ttc agt gaa ttc tat gag gag aac tat gag      3270
Phe Ala Ser Ile Val Asn Phe Ser Glu Phe Tyr Glu Glu Asn Tyr Glu
             1065                1070                1075 ggg ggc aag gag tgc tac cgt gtc ctc aac gag ctg atc ggt gac ttc      3318
Gly Gly Lys Glu Cys Tyr Arg Val Leu Asn Glu Leu Ile Gly Asp Phe
         1080                1085                1090 gat gag ctc ttg agc aag ccg gac tat aat agc atc gag aag atc aag      3366
Asp Glu Leu Leu Ser Lys Pro Asp Tyr Asn Ser Ile Glu Lys Ile Lys
     1095                1100                1105 acc atc ggg gcc aca tac atg gca gcc tca ggg ctg aac acg gcc cag      3414
Thr Ile Gly Ala Thr Tyr Met Ala Ala Ser Gly Leu Asn Thr Ala Gln
 1110                1115                1120 tgt cag gag ggt ggc cac cca cag gag cat ctg cgt atc ctc ttc gag      3462
Cys Gln Glu Gly Gly His Pro Gln Glu His Leu Arg Ile Leu Phe Glu
```

```
                  1125               1130               1135               1140
ttc gcc aag gag atg atg cgc gtg gtg gat gac ttc aac aac aat atg      3510
Phe Ala Lys Glu Met Met Arg Val Val Asp Asp Phe Asn Asn Asn Met
                      1145               1150               1155 tta tgg ttc aac ttc aag ctc agg gtc ggc ttt aac cac gga ccc ctc      3558
Leu Trp Phe Asn Phe Lys Leu Arg Val Gly Phe Asn His Gly Pro Leu
        1160               1165               1170 aca gca ggt gtc ata ggt acc acc aag ctg ctg tat gac atc tgg ggg      3606
Thr Ala Gly Val Ile Gly Thr Thr Lys Leu Leu Tyr Asp Ile Trp Gly
    1175               1180               1185 gac acc gtc aac atc gcc agc agg atg gac acc act ggt gtg gag tgc      3654
Asp Thr Val Asn Ile Ala Ser Arg Met Asp Thr Thr Gly Val Glu Cys
1190               1195               1200 cgt atc cag gtg agc gaa gag agc tac cgt gtg ctg agc aag atg ggt      3702
Arg Ile Gln Val Ser Glu Glu Ser Tyr Arg Val Leu Ser Lys Met Gly
1205               1210               1215               1220 tat gac ttt gac tac cga ggg acc gtg aat gtc aag ggg aaa ggg cag      3750
Tyr Asp Phe Asp Tyr Arg Gly Thr Val Asn Val Lys Gly Lys Gly Gln
            1225               1230               1235 atg aag acc tac ctt tac cca aag tgc acg gac aat gga gtg gtt ccc      3798
Met Lys Thr Tyr Leu Tyr Pro Lys Cys Thr Asp Asn Gly Val Val Pro
        1240               1245               1250 cag cac cag ctg tcc atc tcc cca gac atc cga gtc cag gtg gac ggc      3846
Gln His Gln Leu Ser Ile Ser Pro Asp Ile Arg Val Gln Val Asp Gly
    1255               1260               1265 agc att ggg cgg tct ccc aca gat gag att gcc aac ttg gtg cct tcc      3894
Ser Ile Gly Arg Ser Pro Thr Asp Glu Ile Ala Asn Leu Val Pro Ser
1270               1275               1280 gtt cag tat tcg gac aag gct tcc ctg gga tct gat gat agc aca cag      3942
Val Gln Tyr Ser Asp Lys Ala Ser Leu Gly Ser Asp Asp Ser Thr Gln
1285               1290               1295               1300 gct aag gaa gct cac ctg tcc tct aag agg tcc tgg aga gag cca gtc      3990
Ala Lys Glu Ala His Leu Ser Ser Lys Arg Ser Trp Arg Glu Pro Val
            1305               1310               1315 aaa gca gag gaa agg ttt cca ttt ggc aaa gcc ata gaa aag gac agc      4038
Lys Ala Glu Glu Arg Phe Pro Phe Gly Lys Ala Ile Glu Lys Asp Ser
        1320               1325               1330 tgt gaa gac ata gga gta gaa gag gcc agt gaa ctc agc aag ctc aat      4086
Cys Glu Asp Ile Gly Val Glu Glu Ala Ser Glu Leu Ser Lys Leu Asn
    1335               1340               1345 gtc tca aag agt gtg tgaggcagcg ccgagagctg ccaaggtgct ctgcgtgtcc      4141
Val Ser Lys Ser Val
    1350 aaacacagta acatctgtgt cgataggctg ttgtgctatc tagcacctca gtttctgtcc      4201 ccagatgtgg tgtcacgtgg tcatttcagc ccgaatctct gtgtggagca cagttattca      4261 gggttcattt ccacccattt cggttttcct ttacttgcgt tcctggaagc cttttcctgg      4321 aagcctgccc ccagcccagc caggggatcc agtcagcagc gtggagggat tcaagtgcct      4381 tcagggtctg gccttgcgtc tggggctgag gccactggtg gaatcatggc cctggggatt      4441 atttgacttc tttaagtttt ttttttttt tt                                    4473

<210> SEQ ID NO 2
<211> LENGTH: 1353
<212> TYPE: PRT
<213> ORGANISM: Mouse
<220> FEATURE:
<223> OTHER INFORMATION: HYPOTHETICAL : NO

<400> SEQUENCE: 2
```

-continued

```
Met Ala Ser Ser Pro His Gln Gln Leu Leu His His His Ser Thr Glu
 1               5                  10                  15
Val Ser Cys Asp Ser Ser Gly Asp Ser Asn Ser Val Arg Val Lys Ile
             20                  25                  30
Asn Pro Lys Gln Leu Ser Ser Asn Thr His Pro Lys His Cys Lys Tyr
             35                  40                  45
Ser Ile Ser Ser Ser Cys Ser Ser Ser Gly Asp Ser Gly Gly Leu Pro
             50                  55                  60
Arg Arg Val Gly Gly Gly Arg Leu Arg Arg Gln Lys Lys Leu Pro
 65                  70                  75                  80
Gln Leu Phe Glu Arg Ala Ser Ser Arg Trp Trp Asp Pro Lys Phe Asp
                 85                  90                  95
Ser Met Asn Leu Glu Glu Ala Cys Leu Glu Arg Cys Phe Pro Gln Thr
                100                 105                 110
Gln Arg Arg Phe Arg Tyr Ala Leu Phe Tyr Val Gly Phe Ala Cys Leu
                115                 120                 125
Leu Trp Ser Ile Tyr Phe Ala Val His Met Lys Ser Lys Val Ile Val
 130                 135                 140
Met Val Val Pro Ala Leu Cys Phe Leu Val Val Cys Val Gly Phe Phe
 145                 150                 155                 160
Leu Phe Thr Phe Thr Lys Leu Tyr Ala Arg His Tyr Ala Trp Thr Ser
                 165                 170                 175
Leu Ala Leu Thr Leu Leu Val Phe Ala Leu Thr Leu Ala Ala Gln Phe
                 180                 185                 190
Gln Val Trp Thr Pro Leu Ser Gly Arg Val Asp Ser Ser Asn His Thr
                 195                 200                 205
Leu Thr Ala Thr Pro Ala Asp Thr Cys Leu Ser Gln Val Gly Ser Phe
 210                 215                 220
Ser Ile Cys Ile Glu Val Leu Leu Leu Tyr Thr Val Met Gln Leu
 225                 230                 235                 240
Pro Leu Tyr Leu Ser Leu Phe Leu Gly Val Val Tyr Ser Val Leu Phe
                 245                 250                 255
Glu Thr Phe Gly Tyr His Phe Arg Asn Glu Asp Cys Tyr Pro Ser Pro
                 260                 265                 270
Gly Pro Gly Ala Leu His Trp Glu Leu Leu Ser Arg Ala Leu Leu His
                 275                 280                 285
Val Cys Ile His Ala Ile Gly Ile His Leu Phe Val Met Ser Gln Val
 290                 295                 300
Arg Ser Arg Ser Thr Phe Leu Lys Val Gly Gln Ser Ile Met His Gly
 305                 310                 315                 320
Lys Asp Leu Glu Val Glu Lys Ala Leu Lys Glu Arg Met Ile His Ser
                 325                 330                 335
Val Met Pro Arg Ile Ile Ala Asp Asp Leu Met Lys Gln Gly Asp Glu
                 340                 345                 350
Glu Ser Glu Asn Ser Val Lys Arg His Ala Thr Ser Ser Pro Lys Asn
                 355                 360                 365
Arg Lys Lys Lys Ser Ser Ile Gln Lys Ala Pro Ile Ala Phe Arg Pro
 370                 375                 380
Phe Lys Met Gln Gln Ile Glu Glu Val Ser Ile Leu Phe Ala Asp Ile
 385                 390                 395                 400
Val Gly Phe Thr Lys Met Ser Ala Asn Lys Ser Ala His Ala Leu Val
                 405                 410                 415
```

```
Gly Leu Leu Asn Asp Leu Phe Gly Arg Phe Asp Arg Leu Cys Glu Gln
            420                 425                 430

Thr Lys Cys Glu Lys Ile Ser Thr Leu Gly Asp Cys Tyr Tyr Cys Val
            435                 440                 445

Ala Gly Cys Pro Glu Pro Arg Ala Asp His Ala Tyr Cys Cys Ile Glu
            450                 455                 460

Met Gly Leu Gly Met Ile Lys Ala Ile Glu Gln Phe Cys Gln Glu Lys
465                 470                 475                 480

Lys Glu Met Val Asn Met Arg Val Gly Val His Thr Gly Thr Val Leu
                485                 490                 495

Cys Gly Ile Leu Gly Met Arg Arg Phe Lys Phe Asp Val Trp Ser Asn
            500                 505                 510

Asp Val Asn Leu Ala Asn Leu Met Glu Gln Leu Gly Val Ala Gly Lys
            515                 520                 525

Val His Ile Ser Glu Ala Thr Ala Lys Tyr Leu Asp Asp Arg Tyr Glu
            530                 535                 540

Met Glu Asp Gly Arg Val Ile Glu Arg Leu Gly Gln Ser Val Val Ala
545                 550                 555                 560

Asp Gln Leu Lys Gly Leu Lys Thr Tyr Leu Ile Ser Gly Gln Arg Ala
                565                 570                 575

Lys Glu Ser His Cys Ser Cys Ala Glu Ala Leu Leu Ser Gly Phe Glu
            580                 585                 590

Val Ile Asp Asp Ser Arg Glu Ser Ser Gly Pro Arg Gly Gln Gly Thr
            595                 600                 605

Ala Ser Pro Gly Ser Val Ser Asp Leu Ala Gln Thr Val Lys Thr Phe
            610                 615                 620

Asp Asn Leu Lys Thr Cys Pro Ser Cys Gly Ile Thr Phe Ala Pro Lys
625                 630                 635                 640

Ser Glu Ala Gly Ala Glu Gly Gly Thr Val Gln Asn Gly Cys Gln Asp
                645                 650                 655

Glu Pro Lys Thr Ser Thr Lys Ala Ser Gly Gly Pro Asn Ser Lys Thr
            660                 665                 670

Gln Asn Gly Leu Leu Ser Pro Ala Glu Glu Lys Leu Thr Asn Ser
            675                 680                 685

Gln Thr Ser Leu Cys Glu Ile Leu Gln Glu Lys Gly Arg Trp Ala Gly
            690                 695                 700

Val Ser Leu Asp Gln Ser Ala Leu Leu Pro Leu Arg Phe Lys Asn Ile
705                 710                 715                 720

Arg Glu Lys Thr Asp Ala His Phe Val Asp Val Ile Lys Glu Asp Ser
                725                 730                 735

Leu Met Lys Asp Tyr Phe Phe Lys Pro Pro Ile Asn Gln Phe Ser Leu
            740                 745                 750

Asn Phe Leu Asp Gln Glu Leu Glu Arg Ser Tyr Arg Thr Ser Tyr Gln
            755                 760                 765

Glu Glu Val Ile Lys Asn Ser Pro Val Lys Thr Phe Ala Ser Ala Thr
            770                 775                 780

Phe Ser Ser Leu Leu Asp Val Phe Leu Ser Thr Thr Val Phe Leu Ile
785                 790                 795                 800

Leu Ser Ile Thr Cys Phe Leu Lys Tyr Gly Ala Thr Ala Thr Pro Pro
                805                 810                 815

Pro Pro Ala Ala Leu Ala Val Phe Gly Ala Asp Leu Leu Glu Val
            820                 825                 830

Leu Ser Leu Ile Val Ser Ile Arg Met Val Phe Phe Leu Glu Asp Val
```

-continued

```
                835                 840                 845
Met Thr Cys Thr Lys Trp Leu Leu Glu Trp Ile Ala Gly Trp Leu Pro
    850                 855                 860

Arg His Cys Ile Gly Ala Ile Leu Val Ser Leu Pro Ala Leu Ala Val
865                 870                 875                 880

Tyr Ser His Ile Thr Ser Glu Phe Glu Thr Asn Ile His Val Thr Met
                885                 890                 895

Phe Thr Gly Ser Ala Val Leu Val Ala Val Val His Tyr Cys Asn Phe
            900                 905                 910

Cys Gln Leu Ser Ser Trp Met Arg Ser Ser Leu Ala Thr Ile Val Gly
            915                 920                 925

Ala Gly Leu Leu Leu Leu His Ile Ser Leu Cys Gln Asp Ser Ser
930                 935                 940

Ile Val Met Ser Pro Leu Asp Ser Ala Gln Asn Phe Ser Ala Gln Arg
945                 950                 955                 960

Asn Pro Cys Asn Ser Ser Val Leu Gln Asp Gly Arg Arg Pro Ala Ser
                965                 970                 975

Leu Ile Gly Lys Glu Leu Ile Leu Thr Phe Phe Leu Leu Leu Leu
            980                 985                 990

Val Trp Phe Leu Asn Arg Glu Phe Glu Val Ser Tyr Arg Leu His Tyr
            995                 1000                1005

His Gly Asp Val Glu Ala Asp Leu His Arg Thr Lys Ile Gln Ser Met
    1010                1015                1020

Arg Asp Gln Ala Asp Trp Leu Leu Arg Asn Ile Ile Pro Tyr His Val
025                 1030                1035                1040

Ala Glu Gln Leu Lys Val Ser Gln Thr Tyr Ser Lys Asn His Asp Ser
                1045                1050                1055

Gly Gly Val Ile Phe Ala Ser Ile Val Asn Phe Ser Glu Phe Tyr Glu
            1060                1065                1070

Glu Asn Tyr Glu Gly Gly Lys Glu Cys Tyr Arg Val Leu Asn Glu Leu
            1075                1080                1085

Ile Gly Asp Phe Asp Glu Leu Leu Ser Lys Pro Asp Tyr Asn Ser Ile
    1090                1095                1100

Glu Lys Ile Lys Thr Ile Gly Ala Thr Tyr Met Ala Ala Ser Gly Leu
105                 1110                1115                1120

Asn Thr Ala Gln Cys Gln Glu Gly Gly His Pro Gln Glu His Leu Arg
                1125                1130                1135

Ile Leu Phe Glu Phe Ala Lys Glu Met Met Arg Val Val Asp Asp Phe
            1140                1145                1150

Asn Asn Asn Met Leu Trp Phe Asn Phe Lys Leu Arg Val Gly Phe Asn
            1155                1160                1165

His Gly Pro Leu Thr Ala Gly Val Ile Gly Thr Thr Lys Leu Leu Tyr
    1170                1175                1180

Asp Ile Trp Gly Asp Thr Val Asn Ile Ala Ser Arg Met Asp Thr Thr
185                 1190                1195                1200

Gly Val Glu Cys Arg Ile Gln Val Ser Glu Glu Ser Tyr Arg Val Leu
                1205                1210                1215

Ser Lys Met Gly Tyr Asp Phe Asp Tyr Arg Gly Thr Val Asn Val Lys
            1220                1225                1230

Gly Lys Gly Gln Met Lys Thr Tyr Leu Tyr Pro Lys Cys Thr Asp Asn
        1235                1240                1245

Gly Val Val Pro Gln His Gln Leu Ser Ile Ser Pro Asp Ile Arg Val
    1250                1255                1260
```

```
Gln Val Asp Gly Ser Ile Gly Arg Ser Pro Thr Asp Glu Ile Ala Asn
265                 1270                1275                1280

Leu Val Pro Ser Val Gln Tyr Ser Asp Lys Ala Ser Leu Gly Ser Asp
                1285                1290                1295

Asp Ser Thr Gln Ala Lys Glu Ala His Leu Ser Ser Lys Arg Ser Trp
            1300                1305                1310

Arg Glu Pro Val Lys Ala Glu Arg Phe Pro Phe Gly Lys Ala Ile
        1315                1320                1325

Glu Lys Asp Ser Cys Glu Asp Ile Gly Val Glu Glu Ala Ser Glu Leu
    1330                1335                1340

Ser Lys Leu Asn Val Ser Lys Ser Val
345                 1350

<210> SEQ ID NO 3
<211> LENGTH: 10
<212> TYPE: PRT
<213> ORGANISM: Unknown Organism
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: CELL TYPE : Skeletal muscle
<220> FEATURE:
<223> OTHER INFORMATION: Description of Unknown Organism:

<400> SEQUENCE: 3

Leu Arg Gln Ser Arg Leu Ser Ser Ser Lys
 1               5                   10

<210> SEQ ID NO 4
<211> LENGTH: 11
<212> TYPE: PRT
<213> ORGANISM: mouse
<220> FEATURE:
<223> OTHER INFORMATION: TOPOLOGY : Linear
<220> FEATURE:
<223> OTHER INFORMATION: MOLECULE  TYPE : Peptide
<220> FEATURE:
<223> OTHER INFORMATION: CELL LINE : AtT20

<400> SEQUENCE: 4

Ile Asp Asp Ser Arg Glu Ser Ser Gly Pro Arg
 1               5                   10

<210> SEQ ID NO 5
<211> LENGTH: 26
<212> TYPE: DNA
<213> ORGANISM: Artificial Sequence
<220> FEATURE:
<223> OTHER INFORMATION: HYPOTHETICAL : NO
<220> FEATURE:
<223> OTHER INFORMATION: ANTI-SENSE : NO
<220> FEATURE:
<223> OTHER INFORMATION: CELL LINE : mammalian adenylate cyclases
<220> FEATURE:
<223> OTHER INFORMATION: TOPOLOGY : Linear
<220> FEATURE:
<221> NAME/KEY: misc_feature
<222> LOCATION: (12)
<223> OTHER INFORMATION: Modified base; mod_base= i
<220> FEATURE:
<223> OTHER INFORMATION: STRANDEDNESS : Single
<220> FEATURE:
<223> OTHER INFORMATION: Description of Artificial Sequence:  PCR Primer
      corresponding to highly conserved first
      cytoplasmic domain of mammalian adenyl cyclases
```

```
<400> SEQUENCE: 5
ctcatcgatg gagaytgyta ytaytg                                      26

<210> SEQ ID NO 6
<211> LENGTH: 26
<212> TYPE: DNA
<213> ORGANISM: Artificial Sequence
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : cDNA
<220> FEATURE:
<223> OTHER INFORMATION: HYPOTHETICAL : NO
<220> FEATURE:
<223> OTHER INFORMATION: ANTI-SENSE : NO
<220> FEATURE:
<223> OTHER INFORMATION: CELL LINE : Mammalian adenylate cyclases
<220> FEATURE:
<221> NAME/KEY: misc_feature
<222> LOCATION: (12)
<223> OTHER INFORMATION: modified base; mod_base = i
<220> FEATURE:
<223> OTHER INFORMATION: Description of Artificial Sequence:PCR Primer
      corresponding to highly conserved first
      cytoplasmic domain of mammalian adenyl cyclases

<400> SEQUENCE: 6
ggctcgagcc aaacrtcrta ytgcca                                      26

<210> SEQ ID NO 7
<211> LENGTH: 39
<212> TYPE: DNA
<213> ORGANISM: Artificial Sequence
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : cDNA
<220> FEATURE:
<223> OTHER INFORMATION: HYPOTHETICAL : NO
<220> FEATURE:
<223> OTHER INFORMATION: ANTI-SENSE : NO
<220> FEATURE:
<223> OTHER INFORMATION: CELL LINE : Mammalian adenylate cyclases
<220> FEATURE:
<221> NAME/KEY: misc_feature
<222> LOCATION: (13)
<223> OTHER INFORMATION: modified base; mod_base= i
<220> FEATURE:
<221> NAME/KEY: misc_feature
<222> LOCATION: (19)
<223> OTHER INFORMATION: modified base; mod_base= i
<220> FEATURE:
<221> NAME/KEY: misc_feature
<222> LOCATION: (22)
<223> OTHER INFORMATION: Modified base; mod_base= i
<220> FEATURE:
<221> NAME/KEY: misc_feature
<222> LOCATION: (25)
<223> OTHER INFORMATION: Modified base; mod_base =i
<220> FEATURE:
<221> NAME/KEY: misc_feature
<222> LOCATION: (28)
<223> OTHER INFORMATION: Modified base; Mod_base= i
<220> FEATURE:
<221> NAME/KEY: misc_feature
<222> LOCATION: (31)
<223> OTHER INFORMATION: Modified base; mod_base= i
<220> FEATURE:
<223> OTHER INFORMATION: Description of Artificial Sequence: PCR Primer
      corresponsing to highly conserved second
      cytoplasmic domain of mammalian adenyl cyclases
```

<400> SEQUENCE: 7
gaagcttaar ataaaracaa taggawsaac atayatggc                                39

<210> SEQ ID NO 8
<211> LENGTH: 36
<212> TYPE: DNA
<213> ORGANISM: Artificial Sequence
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE  TYPE : cDNA
<220> FEATURE:
<223> OTHER INFORMATION: HYPOTHETICAL : NO
<220> FEATURE:
<223> OTHER INFORMATION: ANTI-SENSE : NO
<220> FEATURE:
<223> OTHER INFORMATION: CELL LINE : Mammalian adenylate cyclases
<220> FEATURE:
<221> NAME/KEY: misc_feature
<222> LOCATION: (13)
<223> OTHER INFORMATION: Modified base; mod_base= i
<220> FEATURE:
<221> NAME/KEY: misc_feature
<222> LOCATION: (16)
<223> OTHER INFORMATION: Modified base; mod_base= i
<220> FEATURE:
<221> NAME/KEY: misc_feature
<222> LOCATION: (22)
<223> OTHER INFORMATION: Modified base; mod_base= i
<220> FEATURE:
<221> NAME/KEY: misc_feature
<222> LOCATION: (28)
<223> OTHER INFORMATION: Modified base; Mod_base= i
<220> FEATURE:
<223> OTHER INFORMATION: Description of Artificial Sequence: PCR Primer
      corresponding to highly conserved second
      cytoplasmic domain of mammalian adenyl cyclases

<400> SEQUENCE: 8
gggatccacr ttaacagtrt taccccaaat rtcrta                                   36

<210> SEQ ID NO 9
<211> LENGTH: 19
<212> TYPE: DNA
<213> ORGANISM: Artificial Sequence
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : cDNA
<220> FEATURE:
<223> OTHER INFORMATION: HYPOTHETICAL : NO
<220> FEATURE:
<223> OTHER INFORMATION: ANTI-SENSE : YES
<220> FEATURE:
<223> OTHER INFORMATION: CELL LINE : AtT20
<220> FEATURE:
<223> OTHER INFORMATION: Description of Artificial Sequence:PCR Primer
      to cDNA clone jp134 of AtT20

<400> SEQUENCE: 9
cgtcaatgac ctcaaagcc                                                      19

<210> SEQ ID NO 10
<211> LENGTH: 27
<212> TYPE: DNA
<213> ORGANISM: Artificial Sequence
<220> FEATURE:
<223> OTHER INFORMATION: STRANDEDNESS : Single

```
<220> FEATURE:
<223> OTHER INFORMATION: TOPOLOGY : Linear
<220> FEATURE:
<223> OTHER INFORMATION: MOLECULE TYPE : cDNA
<220> FEATURE:
<223> OTHER INFORMATION: HYPOTHETICAL : NO
<220> FEATURE:
<223> OTHER INFORMATION: ANTI-SENSE : YES
<220> FEATURE:
<223> OTHER INFORMATION: CELL LINE : AtT20
<220> FEATURE:
<223> OTHER INFORMATION: Description of Artificial Sequence:PCR Primer
      to cDNA clone jp134 of AtT20

<400> SEQUENCE: 10
gcctctgcac agctgcagtg ggactcc                                            27

<210> SEQ ID NO 11
<211> LENGTH: 33
<212> TYPE: DNA
<213> ORGANISM: Artificial Sequence
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : cDNA
<220> FEATURE:
<223> OTHER INFORMATION: HYPOTHETICAL : NO
<220> FEATURE:
<223> OTHER INFORMATION: ANTI-SENSE : YES
<220> FEATURE:
<223> OTHER INFORMATION: CELL LINE : AtT20
<220> FEATURE:
<223> OTHER INFORMATION: Description of Artificial Sequence:PCR Primer
      to cDNA clone jp134 of AtT20

<400> SEQUENCE: 11
cctggcagaa ctgctcgatg gcttttatca tgc                                     33

<210> SEQ ID NO 12
<211> LENGTH: 18
<212> TYPE: DNA
<213> ORGANISM: Artificial Sequence
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : cDNA
<220> FEATURE:
<223> OTHER INFORMATION: HYPOTHETICAL : NO
<220> FEATURE:
<223> OTHER INFORMATION: ANTI-SENSE : YES
<220> FEATURE:
<223> OTHER INFORMATION: CELL LINE : AtT20
<220> FEATURE:
<223> OTHER INFORMATION: Description of Artificial Sequence: PCR Primer
      to 1kb extension of cDNA clone jp134 of AtT20

<400> SEQUENCE: 12
ggagaagctt cctacttg                                                      18

<210> SEQ ID NO 13
<211> LENGTH: 29
<212> TYPE: DNA
<213> ORGANISM: Artificial Sequence
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE  TYPE :  cDNA
```

```
<220> FEATURE:
<223> OTHER INFORMATION: HYPOTHETICAL : NO
<220> FEATURE:
<223> OTHER INFORMATION: ANTI-SENSE : YES
<220> FEATURE:
<223> OTHER INFORMATION: CELL LINE : AtT20
<220> FEATURE:
<223> OTHER INFORMATION: Description of Artificial Sequence: PCR Primer
      to 1kb extension of cDNA clone jp134 of AtT20

<400> SEQUENCE: 13
gtggccgtga gagtatgatt ggagctgtc                                        29

<210> SEQ ID NO 14
<211> LENGTH: 26
<212> TYPE: DNA
<213> ORGANISM: Artificial Sequence
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE: cDNA
<220> FEATURE:
<223> OTHER INFORMATION: HYPOTHETICAL : NO
<220> FEATURE:
<223> OTHER INFORMATION: ANTI-SENSE : YES
<220> FEATURE:
<223> OTHER INFORMATION: CELL LINE : AtT20
<220> FEATURE:
<223> OTHER INFORMATION: Description of Artificial Sequence: PCR Primer
      to 1kb extension of cDNA clone jp134 of AtT20

<400> SEQUENCE: 14
gtccaaacct gaaactgcgc acgcag                                           26

<210> SEQ ID NO 15
<211> LENGTH: 4
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE  TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 15

Arg Ala Ser Ser
  1

<210> SEQ ID NO 16
<211> LENGTH: 4
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE  TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 16
```

```
Arg Val Asp Ser
  1

<210> SEQ ID NO 17
<211> LENGTH: 4
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE  :  NO

<400> SEQUENCE: 17

Arg Ser Arg Ser
  1

<210> SEQ ID NO 18
<211> LENGTH: 4
<212> TYPE: PRT
<213> ORGANISM: Mouse
<220> FEATURE:
<223> OTHER INFORMATION: STRANDEDNESS: Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 18

Arg Glu Ser Ser
  1

<210> SEQ ID NO 19
<211> LENGTH: 4
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 19

Arg Pro Ala Ser
  1

<210> SEQ ID NO 20
<211> LENGTH: 4
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
```

```
<223> OTHER INFORMATION: HYPOTHETICAL : NO
<220> FEATURE:
<223> OTHER INFORMATION: ANTI-SENSE : NO

<400> SEQUENCE: 20

Arg Val Leu Ser
  1

<210> SEQ ID NO 21
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 21

Lys Ile Lys Thr Ile
  1               5

<210> SEQ ID NO 22
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 22

Lys Thr Ala Thr Leu
  1               5

<210> SEQ ID NO 23
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 23

Lys Ile Ser Thr Leu
  1               5

<210> SEQ ID NO 24
<211> LENGTH: 5
<212> TYPE: PRT
<213> ORGANISM: Mouse
<220> FEATURE:
<223> OTHER INFORMATION: STRANDEDNESS : Single
```

```
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 24

Lys Lys Ser Ser Ile
 1               5

<210> SEQ ID NO 25
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 25

Lys Glu Asp Ser Leu
 1               5

<210> SEQ ID NO 26
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 26

Lys Phe Asp Ser Met
 1               5

<210> SEQ ID NO 27
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 27

Lys Ile Gln Ser Met
 1               5

<210> SEQ ID NO 28
```

-continued

```
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 28

Arg Pro Ala Ser Leu
 1               5

<210> SEQ ID NO 29
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 29

Ser Cys Ala Glu Ala
 1               5

<210> SEQ ID NO 30
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 30

Ser Gly Phe Glu Val
 1               5

<210> SEQ ID NO 31
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 31
```

```
Ser Leu Cys Glu Ile
  1               5

<210> SEQ ID NO 32
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 32

Ser Tyr Gln Glu Glu
  1               5

<210> SEQ ID NO 33
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 33

Ser Glu Phe Glu Thr
  1               5

<210> SEQ ID NO 34
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 34

Ser Trp Arg Glu Pro
  1               5

<210> SEQ ID NO 35
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
```

```
<220> FEATURE:
<223> OTHER INFORMATION: ANTI-SENSE : NO

<400> SEQUENCE: 35

Thr Thr Ser Glu Thr
 1               5

<210> SEQ ID NO 36
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 36

Thr Lys Cys Glu Lys
 1               5

<210> SEQ ID NO 37
<211> LENGTH: 5
<212> TYPE: PRT
<213> ORGANISM: Mouse
<220> FEATURE:
<223> OTHER INFORMATION: STRANDENESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 37

Thr Gly Val Glu Cys
 1               5

<210> SEQ ID NO 38
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 38

Glu Arg Ala Ser Ser
 1               5

<210> SEQ ID NO 39
<211> LENGTH: 5
<212> TYPE: PRT
<213> ORGANISM: Mouse
<220> FEATURE:
<223> OTHER INFORMATION: STRANDEDNESS : Single
<220> FEATURE:
```

```
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 39

Gly Arg Val Asp Ser
 1               5

<210> SEQ ID NO 40
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 40

Val Arg Ser Arg Ser
 1               5

<210> SEQ ID NO 41
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 41

Ser Arg Glu Ser Ser
 1               5

<210> SEQ ID NO 42
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 42

Arg Arg Pro Ala Ser
 1               5

<210> SEQ ID NO 43
<211> LENGTH: 5
```

```
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 43

Tyr Arg Val Leu Ser
 1               5

<210> SEQ ID NO 44
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 44

Lys Arg His Ala Thr
 1               5

<210> SEQ ID NO 45
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 45

Ile Arg Glu Lys Thr
 1               5

<210> SEQ ID NO 46
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 46

Ser Arg Met Asp Thr
```

-continued

```
                1               5
```

<210> SEQ ID NO 47
<211> LENGTH: 5
<212> TYPE: PRT
<213> ORGANISM: Mouse
<220> FEATURE:
<223> OTHER INFORMATION: STRANDEDNESS : Single
<220> FEATURE:
<223> OTHER INFORMATION: TOPOLOGY : Linear
<220> FEATURE:
<223> OTHER INFORMATION: MOLECULE TYPE : Peptide
<220> FEATURE:
<223> OTHER INFORMATION: HYPOTHETICAL : NO
<220> FEATURE:
<223> OTHER INFORMATION: ANTI-SENSE : NO

<400> SEQUENCE: 47

```
Gly Arg Ser Pro Thr
  1               5
```

<210> SEQ ID NO 48
<211> LENGTH: 90
<212> TYPE: PRT
<213> ORGANISM: Human

<400> SEQUENCE: 48

```
Lys Ile Lys Thr Ile Gly Ser Thr Tyr Met Ala Ala Gly Leu Ser
  1               5                  10                  15

Val Ala Ser Gly His Glu Asn Gln Glu Leu Glu Arg Gln His Ala His
             20                  25                  30

Ile Gly Val Met Val Glu Phe Ser Ile Ala Leu Met Ser Lys Leu Asp
         35                  40                  45

Gly Ile Asn Arg His Ser Phe Asn Ser Phe Arg Leu Arg Val Gly Ile
     50                  55                  60

Asn His Gly Pro Val Ile Ala Gly Val Ile Gly Ala Arg Lys Pro Gln
 65                  70                  75                  80

Tyr Asp Ile Trp Gly Asn Thr Val Asn Val
                 85                  90
```

<210> SEQ ID NO 49
<211> LENGTH: 90
<212> TYPE: PRT
<213> ORGANISM: Mouse

<400> SEQUENCE: 49

```
Lys Ile Lys Thr Ile Gly Ser Thr Tyr Met Ala Ala Gly Leu Ser
  1               5                  10                  15

Ala Pro Ser Gly His Glu Asn Gln Asp Leu Glu Arg Lys His Val His
             20                  25                  30

Ile Gly Val Leu Val Glu Phe Ser Met Ala Leu Met Ser Lys Leu Asp
         35                  40                  45

Gly Ile Asn Arg His Ser Phe Asn Ser Phe Arg Leu Arg Val Gly Ile
     50                  55                  60

Asn His Gly Pro Val Ile Ala Gly Val Ile Gly Ala Arg Lys Pro Gln
 65                  70                  75                  80

Tyr Asp Ile Trp Gly Asn Thr Val Asn Val
                 85                  90
```

<210> SEQ ID NO 50
<211> LENGTH: 91
<212> TYPE: PRT

<213> ORGANISM: Rat

<400> SEQUENCE: 50

Lys Ile Lys Thr Ile Gly Ser Thr Tyr Met Ala Ala Thr Gly Leu Ser
1               5                   10                  15

Ala Ile Pro Ser Gln Glu His Ala Gln Glu Pro Glu Arg Gln Tyr Met
            20                  25                  30

His Ile Gly Thr Met Val Glu Phe Ala Tyr Ala Leu Val Gly Lys Leu
        35                  40                  45

Asp Ala Ile Asn Lys His Ser Phe Asn Asp Phe Lys Leu Arg Val Gly
    50                  55                  60

Ile Asn His Gly Pro Val Ile Ala Gly Val Ile Gly Ala Gln Lys Pro
65                  70                  75                  80

Gln Tyr Asp Ile Trp Gly Asn Thr Val Asn Val
                85                  90

<210> SEQ ID NO 51
<211> LENGTH: 91
<212> TYPE: PRT
<213> ORGANISM: Rat

<400> SEQUENCE: 51

Lys Ile Lys Thr Ile Gly Ser Thr Tyr Met Ala Ala Thr Gly Leu Asn
1               5                   10                  15

Ala Thr Pro Gly Gln Asp Thr Gln Gln Asp Ala Glu Arg Ser Cys Ser
            20                  25                  30

His Leu Gly Thr Met Val Glu Phe Ala Val Ala Leu Gly Ser Lys Leu
        35                  40                  45

Gly Val Ile Asn Lys His Ser Phe Asn Asn Phe Arg Leu Arg Val Gly
    50                  55                  60

Leu Asn His Gly Pro Val Val Ala Gly Val Ile Gly Ala Gln Lys Pro
65                  70                  75                  80

Gln Tyr Asp Ile Trp Gly Asn Thr Val Asn Val
                85                  90

<210> SEQ ID NO 52
<211> LENGTH: 86
<212> TYPE: PRT
<213> ORGANISM: Human

<400> SEQUENCE: 52

Lys Ile Lys Thr Ile Gly Ser Thr Tyr Met Ala Val Ser Gly Leu Ser
1               5                   10                  15

Pro Glu Lys Gln Gln Cys Glu Asp Lys Trp Gly His Leu Cys Ala Leu
            20                  25                  30

Ala Asp Phe Ser Leu Ala Leu Thr Glu Ser Ile Gln Glu Ile Asn Lys
        35                  40                  45

His Ser Phe Asn Asn Phe Glu Leu Arg Ile Gly Ile Ser His Gly Ser
    50                  55                  60

Val Val Ala Gly Val Ile Gly Ala Lys Lys Pro Gln Tyr Asp Ile Trp
65                  70                  75                  80

Gly Lys Thr Val Asn Leu
                85

<210> SEQ ID NO 53
<211> LENGTH: 86
<212> TYPE: PRT
<213> ORGANISM: Rat

<400> SEQUENCE: 53

Lys Ile Lys Thr Ile Gly Ser Thr Tyr Met Ala Val Ser Gly Leu Ser
1               5                  10                  15

Pro Glu Lys Gln Gln Cys Glu Asp Lys Trp Gly His Leu Cys Ala Leu
            20                  25                  30

Ala Asp Phe Ser Leu Ala Leu Thr Glu Ser Ile Gln Glu Ile Asn Lys
        35                  40                  45

His Ser Phe Asn Asn Phe Glu Leu Arg Ile Gly Ile Ser His Gly Ser
    50                  55                  60

Val Val Ala Gly Val Ile Gly Ala Lys Lys Pro Gln Tyr Asp Ile Trp
65                  70                  75                  80

Gly Lys Thr Val Asn Leu
                85

<210> SEQ ID NO 54
<211> LENGTH: 85
<212> TYPE: PRT
<213> ORGANISM: Human

<400> SEQUENCE: 54

Lys Ile Lys Thr Ile Gly Ser Thr Tyr Met Ala Ser Gly Leu Asn
1               5                  10                  15

Ala Ser Thr Tyr Asp Gln Val Gly Arg Ser His Ile Thr Ala Leu Ala
            20                  25                  30

Asp Tyr Ala Met Arg Leu Met Glu Gln Met Lys His Ile Asn Glu His
        35                  40                  45

Ser Phe Asn Asn Phe Gln Met Lys Ile Gly Leu Asn Met Gly Pro Val
    50                  55                  60

Val Ala Gly Val Ile Gly Ala Arg Lys Pro Gln Tyr Asp Ile Trp Gly
65                  70                  75                  80

Asn Thr Val Asn Val
                85

<210> SEQ ID NO 55
<211> LENGTH: 85
<212> TYPE: PRT
<213> ORGANISM: Mouse

<400> SEQUENCE: 55

Lys Ile Lys Thr Ile Gly Ser Thr Tyr Met Ala Ala Ser Gly Leu Asn
1               5                  10                  15

Ala Ser Thr Tyr Asp Gln Val Gly Arg Ser His Ile Thr Ala Leu Ala
            20                  25                  30

Asp Tyr Ala Met Arg Leu Met Glu Gln Met Lys His Ile Asn Glu His
        35                  40                  45

Ser Phe Asn Asn Phe Gln Met Lys Ile Gly Leu Asn Met Gly Pro Val
    50                  55                  60

Val Ala Gly Val Ile Gly Ala Arg Lys Pro Gln Tyr Asp Ile Trp Gly
65                  70                  75                  80

Asn Thr Val Asn Val
                85

<210> SEQ ID NO 56
<211> LENGTH: 85
<212> TYPE: PRT
<213> ORGANISM: Mouse

-continued

<400> SEQUENCE: 56

Lys Ile Lys Thr Ile Gly Ser Thr Tyr Met Ala Ala Ser Gly Leu Asn
1               5                   10                  15

Ala Ser Thr Tyr Asp Gln Val Gly Arg Ser His Ile Thr Ala Leu Ala
            20                  25                  30

Asp Tyr Ala Met Arg Leu Met Glu Gln Met Lys His Ile Asn Glu His
        35                  40                  45

Ser Phe Asn Asn Phe Gln Met Lys Ile Gly Leu Asn Met Gly Pro Val
    50                  55                  60

Val Ala Gly Val Ile Gly Ala Arg Lys Pro Gln Tyr Asp Ile Trp Gly
65                  70                  75                  80

Asn Thr Val Asn Val
                85

<210> SEQ ID NO 57
<211> LENGTH: 85
<212> TYPE: PRT
<213> ORGANISM: Rat

<400> SEQUENCE: 57

Lys Ile Lys Thr Ile Gly Ser Thr Tyr Met Ala Ala Ser Gly Leu Asn
1               5                   10                  15

Ala Ser Thr Tyr Asp Gln Val Gly Arg Ser His Ile Thr Ala Leu Ala
            20                  25                  30

Asp Tyr Ala Met Arg Leu Met Glu Gln Met Lys His Ile Asn Glu His
        35                  40                  45

Ser Phe Asn Asn Phe Gln Met Lys Ile Gly Leu Asn Met Gly Pro Val
    50                  55                  60

Val Ala Gly Val Ile Gly Ala Arg Lys Pro Gln Tyr Asp Ile Trp Gly
65                  70                  75                  80

Asn Thr Val Asn Val
                85

<210> SEQ ID NO 58
<211> LENGTH: 85
<212> TYPE: PRT
<213> ORGANISM: Dog

<400> SEQUENCE: 58

Lys Ile Lys Thr Ile Gly Ser Thr Tyr Met Ala Ala Ser Gly Leu Asn
1               5                   10                  15

Ala Ser Thr Tyr Asp Gln Ala Gly Arg Ser His Ile Thr Ala Leu Ala
            20                  25                  30

Asp Tyr Ala Met Arg Leu Met Glu Gln Met Lys His Ile Asn Glu His
        35                  40                  45

Ser Phe Asn Asn Phe Gln Met Lys Ile Gly Leu Asn Met Gly Pro Val
    50                  55                  60

Val Ala Gly Val Ile Gly Ala Arg Lys Pro Gln Tyr Asp Ile Trp Gly
65                  70                  75                  80

Asn Thr Val Asn Val
                85

<210> SEQ ID NO 59
<211> LENGTH: 85
<212> TYPE: PRT
<213> ORGANISM: Rat

<400> SEQUENCE: 59

```
Lys Ile Lys Thr Ile Gly Ser Thr Tyr Met Ala Ala Ser Gly Leu Asn
  1               5                  10                  15

Asp Ser Thr Tyr Asp Lys Ala Gly Lys Thr His Ile Lys Ala Leu Ala
               20                  25                  30

Asp Phe Ala Met Lys Leu Met Asp Gln Met Lys Tyr Ile Asn Glu His
           35                  40                  45

Ser Phe Asn Asn Phe Gln Met Lys Ile Gly Leu Asn Ile Gly Pro Val
       50                  55                  60

Val Ala Gly Val Ile Gly Ala Arg Lys Pro Gln Tyr Asp Ile Trp Gly
 65                  70                  75                  80

Asn Thr Val Asn Val
               85

<210> SEQ ID NO 60
<211> LENGTH: 85
<212> TYPE: PRT
<213> ORGANISM: Rabbit

<400> SEQUENCE: 60

Lys Ile Lys Thr Ile Gly Ser Thr Tyr Met Ala Ala Ser Gly Leu Asn
  1               5                  10                  15

Asp Ser Thr Tyr Asp Lys Val Gly Lys Thr His Ile Lys Ala Leu Ala
               20                  25                  30

Asp Phe Ala Met Lys Leu Met Asp Gln Met Lys Tyr Ile Asn Glu His
           35                  40                  45

Ser Phe Asn Asn Phe Gln Met Lys Ile Gly Leu Asn Ile Gly Pro Val
       50                  55                  60

Val Ala Gly Val Ile Gly Ala Arg Lys Pro Gln Tyr Asp Ile Trp Gly
 65                  70                  75                  80

Asn Thr Val Asn Val
               85

<210> SEQ ID NO 61
<211> LENGTH: 85
<212> TYPE: PRT
<213> ORGANISM: Dog

<400> SEQUENCE: 61

Lys Ile Lys Thr Ile Gly Ser Thr Tyr Met Ala Ala Ser Gly Leu Asn
  1               5                  10                  15

Asp Ser Thr Tyr Asp Lys Val Gly Lys Thr His Ile Lys Ala Leu Ala
               20                  25                  30

Asp Phe Ala Met Lys Leu Met Asp Gln Met Lys Tyr Ile Asn Glu His
           35                  40                  45

Ser Phe Asn Asn Phe Gln Met Lys Ile Gly Leu Asn Ile Gly Pro Val
       50                  55                  60

Val Ala Gly Val Ile Gly Ala Arg Lys Pro Gln Tyr Asp Ile Trp Gly
 65                  70                  75                  80

Asn Thr Val Asn Val
               85

<210> SEQ ID NO 62
<211> LENGTH: 88
<212> TYPE: PRT
<213> ORGANISM: Bovine

<400> SEQUENCE: 62
```

-continued

Lys Ile Lys Thr Ile Gly Ser Thr Tyr Met Ala Ala Val Gly Leu Ala
 1               5                  10                 15

Pro Thr Ala Gly Thr Lys Ala Lys Lys Cys Ile Ser Ser His Leu Ser
            20                  25                  30

Thr Leu Ala Asp Phe Ala Ile Glu Met Phe Asp Val Leu Asp Glu Ile
         35                  40                  45

Asn Tyr Gln Ser Tyr Asn Asp Phe Val Leu Arg Val Gly Ile Asn Val
     50                  55                  60

Gly Pro Val Val Ala Gly Val Ile Gly Ala Arg Arg Pro Gln Tyr Asp
 65                  70                  75                  80

Ile Trp Gly Asn Thr Val Asn Val
                 85

<210> SEQ ID NO 63
<211> LENGTH: 98
<212> TYPE: PRT
<213> ORGANISM: Rat

<400> SEQUENCE: 63

Lys Ile Lys Thr Ile Gly Ser Thr Tyr Met Ala Ala Ser Gly Val Thr
 1               5                  10                 15

Pro Asp Val Asn Thr Asn Gly Phe Thr Ser Ser Ser Lys Glu Glu Lys
            20                  25                  30

Ser Asp Lys Glu Arg Trp Gln His Leu Ala Asp Leu Ala Asp Phe Ala
         35                  40                  45

Leu Ala Met Lys Asp Thr Leu Thr Asn Ile Asn Asn Gln Ser Phe Asn
     50                  55                  60

Asn Phe Met Leu Arg Ile Gly Met Asn Lys Gly Gly Val Leu Ala Gly
 65                  70                  75                  80

Val Ile Gly Ala Arg Lys Pro His Tyr Asp Ile Trp Gly Asn Thr Val
                 85                  90                  95

Asn Val

<210> SEQ ID NO 64
<211> LENGTH: 88
<212> TYPE: PRT
<213> ORGANISM: Mouse
<220> FEATURE:
<223> OTHER INFORMATION: Description of Artificial Sequence: Primer
      based on mouse adenyl cyclase 9

<400> SEQUENCE: 64

Lys Ile Lys Thr Ile Gly Ala Thr Tyr Met Ala Ala Ser Gly Leu Asn
 1               5                  10                 15

Thr Ala Gln Cys Gln Glu Gly Gly His Pro Gln Glu His Leu Arg Ile
            20                  25                  30

Leu Phe Glu Phe Ala Lys Glu Met Met Arg Val Val Asp Asp Phe Asn
         35                  40                  45

Asn Asn Met Leu Trp Phe Asn Phe Lys Leu Arg Val Gly Phe Asn His
     50                  55                  60

Gly Pro Leu Thr Ala Gly Val Ile Gly Thr Thr Lys Leu Leu Tyr Asp
 65                  70                  75                  80

Ile Trp Gly Asp Thr Val Asn Ile
                 85

<210> SEQ ID NO 65
<211> LENGTH: 108
<212> TYPE: PRT

```
<213> ORGANISM: Mouse

<400> SEQUENCE: 65

Arg Phe Lys Phe Asp Val Trp Ser Asn Asp Val Asn Leu Ala Asn Leu
 1               5                  10                  15

Met Glu Gln Leu Gly Val Ala Gly Lys Val His Ile Ser Glu Ala Thr
            20                  25                  30

Ala Lys Tyr Leu Asp Asp Arg Tyr Glu Met Glu Asp Gly Arg Val Ile
        35                  40                  45

Glu Arg Leu Gly Gln Ser Val Val Ala Asp Gln Leu Lys Gly Leu Lys
    50                  55                  60

Thr Tyr Leu Ile Ser Gly Gln Arg Ala Lys Glu Ser His Cys Ser Cys
65                  70                  75                  80

Ala Glu Ala Leu Leu Ser Gly Phe Glu Val Ile Asp Asp Ser Arg Glu
                85                  90                  95

Ser Ser Gly Pro Arg Gly Gln Gly Thr Ala Ser Pro
            100                 105

<210> SEQ ID NO 66
<211> LENGTH: 107
<212> TYPE: PRT
<213> ORGANISM: Saccharomyces cerevisiae

<400> SEQUENCE: 66

Asn Val Lys Ile Asp Arg Ile Ser Pro Gly Asp Gly Ala Thr Phe Pro
 1               5                  10                  15

Lys Thr Gly Asp Leu Val Thr Ile His Tyr Thr Gly Thr Leu Glu Asn
            20                  25                  30

Gly Gln Lys Phe Asp Ser Ser Val Asp Arg Gly Ser Pro Phe Gln Cys
        35                  40                  45

Asn Ile Gly Val Gly Gln Val Ile Lys Gly Trp Asp Val Gly Ile Pro
    50                  55                  60

Lys Leu Ser Val Gly Glu Lys Ala Arg Leu Thr Ile Pro Gly Pro Tyr
65                  70                  75                  80

Ala Tyr Gly Pro Arg Gly Phe Pro Gly Leu Ile Pro Pro Asn Ser Thr
                85                  90                  95

Leu Val Phe Asp Val Glu Leu Leu Lys Val Asn
            100                 105

<210> SEQ ID NO 67
<211> LENGTH: 107
<212> TYPE: PRT
<213> ORGANISM: Human

<400> SEQUENCE: 67

Gly Val Gln Val Glu Thr Ile Ser Pro Gly Asp Gly Arg Thr Phe Pro
 1               5                  10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95
```

```
Leu Val Phe Asp Val Glu Leu Leu Lys Leu Glu
            100                 105

<210> SEQ ID NO 68
<211> LENGTH: 107
<212> TYPE: PRT
<213> ORGANISM: Mouse

<400> SEQUENCE: 68

Gly Val Gln Val Glu Thr Ile Ser Pro Gly Asp Gly Arg Thr Phe Pro
  1               5                  10                  15

Lys Arg Gly Gln Thr Cys Val Val His Tyr Thr Gly Met Leu Glu Asp
             20                  25                  30

Gly Lys Lys Phe Asp Ser Ser Arg Asp Arg Asn Lys Pro Phe Lys Phe
         35                  40                  45

Thr Leu Gly Lys Gln Glu Val Ile Arg Gly Trp Glu Glu Gly Val Ala
     50                  55                  60

Gln Met Ser Val Gly Gln Arg Ala Lys Leu Ile Ile Ser Ser Asp Tyr
 65                  70                  75                  80

Ala Tyr Gly Ala Thr Gly His Pro Gly Ile Ile Pro Pro His Ala Thr
                 85                  90                  95

Leu Val Phe Asp Val Glu Leu Leu Lys Leu Glu
            100                 105

<210> SEQ ID NO 69
<211> LENGTH: 107
<212> TYPE: PRT
<213> ORGANISM: Neurospora crassa

<400> SEQUENCE: 69

Gly Leu Gln Ile Glu Val Gln Gln Glu Gly Gln Gly Thr Arg Glu Thr
  1               5                  10                  15

Arg Arg Gly Asp Asn Val Asp Val His Tyr Lys Gly Val Leu Thr Ser
             20                  25                  30

Gly Lys Lys Phe Asp Ala Ser Tyr Asp Arg Gly Glu Pro Leu Asn Phe
         35                  40                  45

Thr Val Gly Gln Gly Gln Val Ile Lys Gly Trp Asp Glu Gly Leu Leu
     50                  55                  60

Gly Met Lys Ile Gly Glu Lys Arg Lys Leu Thr Ile Ala Pro His Leu
 65                  70                  75                  80

Ala Tyr Gly Asn Arg Ala Val Gly Gly Ile Ile Pro Ala Asn Ser Thr
                 85                  90                  95

Leu Ile Phe Glu Thr Glu Leu Val Gly Ile Lys
            100                 105

<210> SEQ ID NO 70
<211> LENGTH: 104
<212> TYPE: PRT
<213> ORGANISM: Bovine

<400> SEQUENCE: 70

Lys Trp Gln Tyr Asp Val Trp Ser Asn Asp Val Thr Leu Ala Asn Val
  1               5                  10                  15

Met Glu Ala Ala Gly Leu Pro Gly Lys Val His Ile Thr Lys Thr Thr
             20                  25                  30

Leu Ala Cys Leu Asn Gly Asp Tyr Glu Val Glu Pro Gly His Gly His
         35                  40                  45
```

-continued

```
Glu Arg Asn Ser Phe Leu Lys Thr His Asn Ile Glu Thr Phe Phe Ile
 50                  55                  60
Val Pro Ser His Arg Arg Lys Ile Phe Pro Gly Leu Ile Leu Ser Asp
 65                  70                  75                  80
Ile Lys Pro Ala Lys Arg Met Lys Phe Lys Thr Val Cys Tyr Leu Leu
                 85                  90                  95
Val Gln Leu Met Tyr His Cys Arg
            100
```

<210> SEQ ID NO 71
<211> LENGTH: 104
<212> TYPE: PRT
<213> ORGANISM: Rat

<400> SEQUENCE: 71

```
Arg Trp Gln Tyr Asp Val Trp Ser Thr Asp Val Thr Val Ala Asn Lys
 1                5                  10                  15
Met Glu Ala Gly Gly Ile Pro Gly Arg Val His Ile Ser Gln Ser Thr
                 20                  25                  30
Met Asp Cys Leu Lys Gly Glu Phe Asp Val Glu Pro Gly Asp Gly Gly
             35                  40                  45
Ser Arg Cys Asp Tyr Leu Asp Glu Lys Gly Ile Glu Thr Tyr Leu Ile
 50                  55                  60
Ile Ala Ser Lys Pro Glu Val Lys Lys Thr Ala Gln Asn Gly Leu Asn
 65                  70                  75                  80
Gly Ser Ala Leu Pro Asn Gly Ala Pro Ala Ser Lys Pro Ser Ser Ser
                 85                  90                  95
Pro Ala Leu Ile Glu Thr Lys Glu
            100
```

<210> SEQ ID NO 72
<211> LENGTH: 104
<212> TYPE: PRT
<213> ORGANISM: Rat

<400> SEQUENCE: 72

```
Lys Trp Gln Phe Asp Val Trp Ser Trp Asp Val Asp Ile Ala Asn Lys
 1                5                  10                  15
Leu Glu Ser Gly Gly Ile Pro Gly Arg Ile His Ile Ser Lys Ala Thr
                 20                  25                  30
Leu Asp Cys Leu Ser Gly Asp Tyr Asn Val Glu Glu Gly His Gly Lys
             35                  40                  45
Glu Arg Asn Glu Phe Leu Arg Lys His Asn Ile Glu Thr Tyr Leu Ile
 50                  55                  60
Lys Gln Pro Glu Glu Ser Leu Leu Ser Leu Pro Glu Asp Ile Val Lys
 65                  70                  75                  80
Glu Ser Val Ser Cys Ser Asp Arg Arg Asn Ser Gly Ala Thr Phe Thr
                 85                  90                  95
Glu Gly Ser Trp Ser Pro Glu Leu
            100
```

<210> SEQ ID NO 73
<211> LENGTH: 104
<212> TYPE: PRT
<213> ORGANISM: Rat

<400> SEQUENCE: 73

```
Lys Trp Gln Phe Asp Val Trp Ser Asn Asp Val Thr Leu Ala Asn His
 1                5                  10                  15
```

```
                1               5                  10                      15
            Met Glu Ala Gly Gly Lys Ala Gly Arg Ile His Ile Thr Lys Ala Thr
                            20                  25                  30
            Leu Asn Tyr Leu Asn Gly Asp Tyr Glu Val Glu Pro Gly Cys Gly Gly
                        35                  40                  45
            Glu Arg Asn Ala Tyr Leu Lys Glu His Ser Ile Glu Thr Phe Leu Ile
                    50                  55                  60
            Leu Arg Cys Thr Gln Lys Arg Lys Glu Glu Lys Ala Met Ile Ala Lys
            65                  70                  75                  80
            Met Asn Arg Gln Arg Thr Asn Ser Ile Gly His Asn Pro Pro His Trp
                            85                  90                  95
            Gly Ala Glu Arg Pro Phe Tyr Asn
                            100
```

<210> SEQ ID NO 74
<211> LENGTH: 104
<212> TYPE: PRT
<213> ORGANISM: Rat

<400> SEQUENCE: 74

```
                1               5                  10                      15
            Lys Trp Gln Phe Asp Val Trp Ser Asn Asp Val Thr Leu Ala Asn His
                            20                  25                  30
            Met Glu Ala Gly Gly Arg Ala Gly Arg Ile His Ile Thr Arg Ala Thr
                        35                  40                  45
            Leu Gln Tyr Leu Asn Gly Asp Tyr Glu Val Glu Pro Gly Arg Gly Gly
                    50                  55                  60
            Glu Arg Asn Gly Tyr Leu Lys Glu Gln Cys Ile Glu Thr Phe Leu Ile
            65                  70                  75                  80
            Leu Gly Ala Ser Gln Lys Arg Lys Glu Glu Lys Ala Met Leu Val Lys
                            85                  90                  95
            Leu Gln Arg Thr Arg Ala Asn Ser Met Glu Gly Leu Met Pro His Trp
                            100
            Gly Ala Glu Arg Pro Phe Tyr Asn
```

<210> SEQ ID NO 75
<211> LENGTH: 102
<212> TYPE: PRT
<213> ORGANISM: Rat

<400> SEQUENCE: 75

```
                1               5                  10                      15
            Lys Trp Gln Tyr Asp Val Trp Ser His Asp Val Thr Leu Ala Asn His
                            20                  25                  30
            Met Glu Ala Gly Gly Val Pro Gly Arg Val His Ile Ser Ser Val Thr
                        35                  40                  45
            Leu Glu His Leu Asn Gly Ala Tyr Lys Val Glu Gly Asp Gly Glu
                    50                  55                  60
            Ile Arg Asp Pro Tyr Leu Lys Gln His Leu Val Lys Thr Tyr Phe Val
            65                  70                  75                  80
            Ile Asn Pro Lys Gly Glu Arg Arg Ser Pro Gln His Leu Phe Arg Pro
                            85                  90                  95
            Arg His Thr Leu Asp Gly Ala Lys Met Arg Ala Ser Val Arg Met Thr
                            100
            Arg Tyr Leu Ser Trp Gly
```

-continued

```
<210> SEQ ID NO 76
<211> LENGTH: 103
<212> TYPE: PRT
<213> ORGANISM: Rat

<400> SEQUENCE: 76

Lys Asn Gln Tyr Asp Val Asn Ser His Asp Val Thr Leu Ala Asn His
  1               5                  10                  15

Met Glu Ala Gly Gly Val Pro Gly Arg Val His Ile Thr Gly Ala Thr
             20                  25                  30

Leu Ala Leu Leu Ala Gly Ala Tyr Ala Val Glu Arg Ala Asp Met Glu
         35                  40                  45

His Arg Asp Pro Tyr Leu Arg Glu Leu Gly Glu Pro Thr Tyr Leu Val
     50                  55                  60

Ile Asp Pro Trp Ala Glu Glu Asp Glu Lys Gly Thr Glu Arg Gly
 65                  70                  75                  80

Leu Leu Ser Ser Leu Glu Gly His Thr Met Arg Pro Ser Leu Leu Met
                 85                  90                  95

Thr Arg Tyr Leu Ser Trp Gly
            100

<210> SEQ ID NO 77
<211> LENGTH: 103
<212> TYPE: PRT
<213> ORGANISM: Mouse

<400> SEQUENCE: 77

Lys Trp Gln Tyr Asp Val Trp Ser His Asp Val Ser Leu Ala Asn Arg
  1               5                  10                  15

Met Glu Ala Ala Gly Val Pro Gly Arg Val His Ile Thr Glu Ala Thr
             20                  25                  30

Leu Asn His Leu Asp Lys Ala Tyr Glu Val Glu Asp Gly His Gly Glu
         35                  40                  45

Gln Arg Asp Pro Tyr Leu Lys Glu Met Asn Ile Arg Thr Tyr Leu Val
     50                  55                  60

Ile Asp Pro Arg Ser Gln Gln Pro Pro Pro Ser His His Leu Ser
 65                  70                  75                  80

Lys Pro Lys Gly Asp Ala Thr Leu Lys Met Arg Ala Ser Val Arg Val
                 85                  90                  95

Thr Arg Tyr Leu Ser Trp Gly
            100

<210> SEQ ID NO 78
<211> LENGTH: 103
<212> TYPE: PRT
<213> ORGANISM: Human

<400> SEQUENCE: 78

Lys Trp Gln Tyr Asp Val Trp Ser His Asp Val Ser Leu Ala Asn Arg
  1               5                  10                  15

Met Glu Ala Ala Gly Val Pro Gly Arg Val His Ile Thr Glu Ala Thr
             20                  25                  30

Leu Lys His Leu Asp Lys Ala Tyr Glu Val Glu Asp Gly His Gly Gln
         35                  40                  45

Gln Arg Asp Pro Tyr Leu Lys Glu Met Asn Ile Arg Thr Tyr Leu Val
     50                  55                  60

Ile Asp Pro Arg Ser Gln Gln Pro Pro Pro Ser Gln His Leu Pro
 65                  70                  75                  80
```

-continued

```
Arg Pro Lys Gly Asp Ala Ala Leu Lys Met Arg Ala Ser Val Arg Met
                85                  90                  95

Thr Arg Tyr Leu Ser Trp Gly
            100

<210> SEQ ID NO 79
<211> LENGTH: 107
<212> TYPE: PRT
<213> ORGANISM: Yeast

<400> SEQUENCE: 79

Asn Val Lys Ile Asp Arg Ile Ser Pro Gly Asp Gly Ala Thr Phe Pro
  1               5                  10                  15

Lys Thr Gly Asp Leu Val Thr Ile His Tyr Thr Gly Thr Leu Glu Asn
             20                  25                  30

Gly Gln Lys Phe Asp Ser Ser Val Asp Arg Gly Ser Pro Phe Gln Cys
         35                  40                  45

Asn Ile Gly Val Gly Gln Val Ile Lys Gly Trp Asp Val Gly Ile Pro
 50                  55                  60

Lys Leu Ser Val Gly Glu Lys Ala Arg Leu Thr Ile Pro Gly Pro Tyr
 65                  70                  75                  80

Ala Tyr Gly Pro Arg Gly Phe Pro Gly Leu Ile Pro Pro Asn Ser Thr
                 85                  90                  95

Leu Val Phe Asp Val Glu Leu Leu Lys Val Asn
            100                 105

<210> SEQ ID NO 80
<211> LENGTH: 107
<212> TYPE: PRT
<213> ORGANISM: Human

<400> SEQUENCE: 80

Gly Val Gln Val Glu Thr Ile Ser Pro Gly Asp Gly Arg Thr Phe Pro
  1               5                  10                  15

Lys Arg Gly Gln Thr Cys Val Val His Tyr Thr Gly Met Leu Glu Asp
             20                  25                  30

Gly Lys Lys Phe Asp Ser Ser Arg Asp Arg Asn Lys Pro Phe Lys Phe
         35                  40                  45

Met Leu Gly Lys Gln Glu Val Ile Arg Gly Trp Glu Glu Gly Val Ala
 50                  55                  60

Gln Met Ser Val Gly Gln Arg Ala Lys Leu Thr Ile Ser Pro Asp Tyr
 65                  70                  75                  80

Ala Tyr Gly Ala Thr Gly His Pro Gly Ile Ile Pro Pro His Ala Thr
                 85                  90                  95

Leu Val Phe Asp Val Glu Leu Leu Lys Leu Glu
            100                 105

<210> SEQ ID NO 81
<211> LENGTH: 107
<212> TYPE: PRT
<213> ORGANISM: Mouse

<400> SEQUENCE: 81

Gly Val Gln Val Glu Thr Ile Ser Pro Gly Asp Gly Arg Thr Phe Pro
  1               5                  10                  15

Lys Arg Gly Gln Thr Cys Val Val His Tyr Thr Gly Met Leu Glu Asp
             20                  25                  30
```

```
Gly Lys Lys Phe Asp Ser Ser Arg Asp Arg Asn Lys Pro Phe Lys Phe
            35                  40                  45

Thr Leu Gly Lys Gln Glu Val Ile Arg Gly Trp Glu Glu Gly Val Ala
        50                  55                  60

Gln Met Ser Val Gly Gln Arg Ala Lys Leu Ile Ile Ser Ser Asp Tyr
 65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 82
<211> LENGTH: 107
<212> TYPE: PRT
<213> ORGANISM: Bovine

<400> SEQUENCE: 82

Gly Val Glu Ile Glu Thr Ile Ser Pro Gly Asp Gly Arg Thr Phe Pro
  1               5                  10                  15

Lys Lys Gly Gln Thr Cys Val Val His Tyr Thr Gly Met Leu Gln Asn
            20                  25                  30

Gly Lys Lys Phe Asp Ser Ser Arg Asp Arg Asn Lys Pro Phe Lys Phe
            35                  40                  45

Arg Ile Gly Lys Gln Glu Val Ile Lys Gly Phe Glu Glu Gly Ala Ala
        50                  55                  60

Gln Met Ser Leu Gly Gln Arg Ala Lys Leu Thr Cys Thr Pro Asp Val
 65                  70                  75                  80

Ala Tyr Gly Ala Thr Gly His Pro Gly Val Ile Pro Pro Asn Ala Thr
                85                  90                  95

Leu Ile Phe Asp Val Glu Leu Leu Asn Leu Glu
            100                 105

<210> SEQ ID NO 83
<211> LENGTH: 107
<212> TYPE: PRT
<213> ORGANISM: Neurospora crassa

<400> SEQUENCE: 83

Gly Leu Gln Ile Glu Val Gln Glu Gly Gln Gly Thr Arg Glu Thr
  1               5                  10                  15

Arg Arg Gly Asp Asn Val Asp Val His Tyr Lys Gly Val Leu Thr Ser
            20                  25                  30

Gly Lys Lys Phe Asp Ala Ser Tyr Asp Arg Gly Glu Pro Leu Asn Phe
            35                  40                  45

Thr Val Gly Gln Gly Val Ile Lys Gly Trp Asp Glu Gly Leu Leu
        50                  55                  60

Gly Met Lys Ile Gly Glu Lys Arg Lys Leu Thr Ile Ala Pro His Leu
 65                  70                  75                  80

Ala Tyr Gly Asn Arg Ala Val Gly Gly Ile Ile Pro Ala Asn Ser Thr
                85                  90                  95

Leu Ile Phe Glu Thr Glu Leu Val Gly Ile Lys
            100                 105

<210> SEQ ID NO 84
<211> LENGTH: 105
<212> TYPE: PRT
<213> ORGANISM: Human
```

```
<400> SEQUENCE: 84

Arg Val Asp His Cys Pro Ile Lys Ser Arg Lys Gly Asp Val Leu His
 1               5                  10                  15

Met His Tyr Thr Gly Lys Leu Glu Asp Gly Thr Glu Phe Asp Ser Ser
             20                  25                  30

Leu Pro Gln Asn Gln Pro Phe Val Phe Ser Leu Gly Thr Gly Gln Val
         35                  40                  45

Ile Lys Gly Trp Asp Gln Gly Leu Leu Gly Met Tyr Glu Gly Glu Lys
 50                  55                  60

Arg Lys Leu Val Ile Pro Ser Glu Leu Gly Tyr Gly Glu Arg Gly Ala
 65                  70                  75                  80

Pro Pro Lys Ile Pro Gly Gly Ala Thr Leu Val Phe Glu Val Glu Leu
             85                  90                  95

Leu Lys Ile Glu Arg Arg Thr Glu Leu
            100                 105

<210> SEQ ID NO 85
<211> LENGTH: 103
<212> TYPE: PRT
<213> ORGANISM: Human

<400> SEQUENCE: 85

Ser Val Leu Lys Lys Gly Asp Lys Thr Asn Phe Pro Lys Lys Gly Asp
 1               5                  10                  15

Val Val His Cys Trp Tyr Thr Gly Thr Leu Gln Asp Gly Thr Val Phe
             20                  25                  30

Asp Thr Asn Ile Gln Thr Ser Lys Pro Leu Ser Phe Lys Val Gly Val
         35                  40                  45

Gly Lys Val Ile Arg Gly Trp Asp Glu Ala Leu Leu Thr Met Ser Lys
 50                  55                  60

Gly Glu Lys Ala Arg Leu Glu Ile Glu Pro Glu Trp Ala Tyr Gly Lys
 65                  70                  75                  80

Lys Gly Gln Pro Ala Lys Ile Pro Pro Asn Ala Lys Leu Thr Phe Glu
             85                  90                  95

Val Glu Leu Val Asp Ile Asp
            100

<210> SEQ ID NO 86
<211> LENGTH: 104
<212> TYPE: PRT
<213> ORGANISM: Yeast

<400> SEQUENCE: 86

Ile Lys Arg Ile Pro Val Glu Asp Cys Leu Ile Lys Ala Met Pro Gly
 1               5                  10                  15

Asp Lys Val Lys Val His Tyr Thr Gly Ser Leu Glu Ser Gly Thr Val
             20                  25                  30

Phe Asp Ser Ser Tyr Ser Arg Gly Ser Pro Ile Ala Phe Glu Leu Gly
         35                  40                  45

Val Gly Arg Val Ile Lys Gly Trp Asp Gln Gly Val Ala Gly Met Cys
 50                  55                  60

Val Gly Glu Lys Arg Lys Leu Gln Ile Pro Ser Ser Leu Ala Tyr Gly
 65                  70                  75                  80

Glu Arg Gly Val Pro Gly Val Ile Pro Pro Ser Ala Asp Leu Val Phe
             85                  90                  95

Asp Val Glu Leu Val Asp Val Lys
```

-continued

<210> SEQ ID NO 87
<211> LENGTH: 110
<212> TYPE: PRT
<213> ORGANISM: Bovine

<400> SEQUENCE: 87

```
Thr Gly Arg Val Leu Cys Gly Val Leu Gly Leu Arg Lys Trp Gln Tyr
  1               5                  10                  15
Asp Val Trp Ser Asn Asp Val Thr Leu Ala Asn Val Met Glu Ala Ala
                 20                  25                  30
Gly Leu Pro Gly Lys Val His Ile Thr Lys Thr Thr Leu Ala Cys Leu
             35                  40                  45
Asn Gly Asp Tyr Glu Val Glu Pro Gly His Gly His Glu Arg Asn Ser
         50                  55                  60
Phe Leu Lys Thr His Asn Ile Glu Thr Phe Phe Ile Val Pro Ser His
 65                  70                  75                  80
Arg Arg Lys Ile Phe Pro Gly Leu Ile Ile Ser Asp Ile Lys Pro Ala
                 85                  90                  95
Lys Arg Met Lys Phe Lys Thr Val Cys Tyr Leu Ile Val Gln
                100                 105                 110
```

<210> SEQ ID NO 88
<211> LENGTH: 109
<212> TYPE: PRT
<213> ORGANISM: Rat

<400> SEQUENCE: 88

```
Ala Asn Lys Met Glu Ala Gly Gly Ile Pro Gly Arg Val His Ile Ser
  1               5                  10                  15
Gln Ser Thr Met Asp Cys Leu Lys Gly Glu Phe Asp Val Glu Pro Gly
                 20                  25                  30
Asp Gly Gly Ser Arg Cys Asp Tyr Leu Asp Glu Lys Gly Ile Glu Thr
             35                  40                  45
Tyr Leu Ile Ile Ala Ser Lys Pro Glu Val Lys Lys Thr Ala Gln Asn
         50                  55                  60
Gly Leu Asn Gly Ser Ala Leu Pro Asn Gly Ala Pro Ala Ser Lys Pro
 65                  70                  75                  80
Ser Ser Pro Ala Leu Ile Glu Thr Lys Glu Pro Asn Gly Ser Ala His
                 85                  90                  95
Ala Ser Gly Ser Thr Ser Glu Glu Ala Glu Glu Gln Glu
                100                 105
```

<210> SEQ ID NO 89
<211> LENGTH: 101
<212> TYPE: PRT
<213> ORGANISM: Rat

<400> SEQUENCE: 89

```
Ala Asn Lys Leu Glu Ser Gly Gly Ile Pro Gly Arg Ile His Ile Ser
  1               5                  10                  15
Lys Ala Thr Leu Asp Cys Leu Ser Gly Asp Tyr Asn Val Glu Glu Gly
                 20                  25                  30
His Gly Lys Glu Arg Asn Glu Phe Leu Arg Lys His Asn Ile Glu Thr
             35                  40                  45
Tyr Leu Ile Lys Gln Pro Glu Glu Ser Leu Leu Ser Leu Pro Glu Asp
         50                  55                  60
```

Ile Val Lys Glu Ser Val Ser Cys Ser Asp Arg Arg Asn Ser Gly Ala
65                  70                  75                  80

Thr Phe Thr Glu Gly Ser Trp Ser Pro Glu Leu Pro Phe Asp Asn Ile
                85                  90                  95

Val Gly Lys Gln Asn
            100

<210> SEQ ID NO 90
<211> LENGTH: 101
<212> TYPE: PRT
<213> ORGANISM: Drosophilia calmodulin

<400> SEQUENCE: 90

Ala Asn His Met Glu Ser Gly Gly Glu Pro Gly Arg Val His Val Thr
1               5                   10                  15

Arg Ala Thr Asp Ser Leu Ser Gly Glu Tyr Glu Val Glu Ala Gly His
                20                  25                  30

Gly Asp Glu Arg Ser Ser Tyr Leu Arg Asp His Gly Val Asp Thr Phe
            35                  40                  45

Phe Ile Val Pro Pro His Arg Arg Lys Pro Leu Met Leu Asn Thr
        50                  55                  60

Leu Gly Val Arg Ser Ala Ile Gly Ser Arg Arg Lys Leu Ser Phe Arg
65                  70                  75                  80

Asn Val Ser Asn Val Val Met Gln Leu Leu His Thr Ile Lys Phe Ser
                85                  90                  95

Glu Pro Val Pro Phe
            100

<210> SEQ ID NO 91
<211> LENGTH: 109
<212> TYPE: PRT
<213> ORGANISM: Rat

<400> SEQUENCE: 91

Lys Trp Gln Phe Asp Val Trp Ser Asn Asp Val Thr Leu Ala Asn His
1               5                   10                  15

Met Glu Ala Gly Gly Lys Ala Gly Arg Ile His Ile Thr Lys Ala Thr
                20                  25                  30

Leu Asn Tyr Leu Asn Gly Asp Tyr Glu Val Glu Pro Gly Cys Gly Gly
            35                  40                  45

Glu Arg Asn Ala Tyr Leu Lys Glu His Ser Ile Glu Thr Phe Leu Ile
        50                  55                  60

Leu Arg Cys Thr Gln Lys Arg Lys Glu Gly Lys Ala Met Ile Ala Lys
65                  70                  75                  80

Met Asn Arg Gln Arg Thr Asn Ser Ile Gly His Asn Pro Pro His Trp
                85                  90                  95

Gly Ala Glu Arg Pro Phe Tyr Asn His Leu Gly Gly Asn
            100                 105

<210> SEQ ID NO 92
<211> LENGTH: 119
<212> TYPE: PRT
<213> ORGANISM: Dog

<400> SEQUENCE: 92

Gly Met Asp Met Ile Glu Ala Ile Ser Leu Val Arg Glu Val Thr Gly
1               5                   10                  15

-continued

Val Asn Val Asn Met Arg Val Gly Ile His Ser Gly Arg Val His Cys
                20                  25                  30

Gly Val Leu Gly Leu Arg Lys Trp Gln Phe Asp Val Trp Ser Asn Asp
            35                  40                  45

Val Thr Leu Ala Asn His Met Glu Ala Gly Gly Lys Ala Gly Arg Ile
        50                  55                  60

His Ile Thr Lys Ala Thr Leu Ser Tyr Leu Asn Gly Asp Tyr Glu Val
 65                  70                  75                  80

Glu Pro Gly Cys Gly Gly Glu Arg Asn Ala Tyr Leu Lys Glu His Ser
                85                  90                  95

Ile Glu Thr Phe Leu Ile Leu Arg Cys Thr Gln Lys Arg Val Arg Gly
            100                 105                 110

Gly Gly Gly Pro Arg Pro Gly
            115

<210> SEQ ID NO 93
<211> LENGTH: 113
<212> TYPE: PRT
<213> ORGANISM: Rat

<400> SEQUENCE: 93

Lys Trp Gln Phe Asp Val Trp Ser Asn Asp Val Thr Leu Ala Asn His
 1               5                  10                  15

Met Glu Ala Ala Arg Ala Gly Arg Ile His Ile Thr Arg Ala Thr Leu
                20                  25                  30

Gln Tyr Leu Asn Gly Asp Tyr Glu Val Glu Pro Gly Arg Gly Gly Glu
            35                  40                  45

Arg Asn Ala Tyr Leu Lys Glu Gln His Ile Glu Thr Phe Leu Ile Leu
 50                  55                  60

Gly Ala Ser Gln Lys Arg Lys Glu Glu Lys Ala Met Leu Ala Lys Leu
 65                  70                  75                  80

Gln Arg Thr Arg Ala Asn Ser Met Glu Gly Leu Met Pro Arg Trp Val
                85                  90                  95

Pro Asp Arg Ala Phe Ser Arg Thr Lys Asp Ser Lys Ala Phe Arg Gln
            100                 105                 110

Met

<210> SEQ ID NO 94
<211> LENGTH: 106
<212> TYPE: PRT
<213> ORGANISM: Mouse

<400> SEQUENCE: 94

Arg Phe Lys Phe Asp Val Trp Ser Asn Asp Val Asn Leu Ala Asn Leu
 1               5                  10                  15

Met Glu Gln Leu Gly Val Ala Gly Lys Val His Ile Ser Glu Ala Thr
                20                  25                  30

Ala Lys Tyr Leu Asp Asp Arg Tyr Glu Met Glu Asp Gly Arg Val Ile
            35                  40                  45

Glu Arg Leu Gly Gln Ser Val Val Ala Asp Gln Leu Lys Gly Leu Lys
 50                  55                  60

Thr Tyr Leu Ile Ser Gly Gln Arg Ala Lys Glu Ser His Cys Ser Cys
 65                  70                  75                  80

Ala Glu Ala Leu Leu Gly Phe Glu Val Ile Asp Asp Ser Arg Glu Ser
                85                  90                  95

Ser Gly Pro Arg Gly Gln Gly Thr Ala Ser

<210> SEQ ID NO 95
<211> LENGTH: 109
<212> TYPE: PRT
<213> ORGANISM: Rat

<400> SEQUENCE: 95

Lys Trp Gln Tyr Asp Val Trp Ser His Asp Val Thr Leu Ala Asn His
1               5                   10                  15

Met Glu Ala Gly Gly Val Pro Gly Arg Val His Ile Ser Ser Val Thr
            20                  25                  30

Leu Glu His Leu Asn Gly Ala Tyr Lys Val Glu Glu Gly Asp Gly Glu
        35                  40                  45

Ile Arg Asp Pro Tyr Leu Lys Gln His Leu Val Lys Thr Tyr Phe Val
    50                  55                  60

Ile Asn Pro Lys Gly Glu Arg Ser Pro Gln His Leu Phe Arg Pro
65                  70                  75                  80

Arg His Thr Leu Asp Gly Ala Lys Met Arg Ala Ser Val Arg Met Thr
                85                  90                  95

Arg Tyr Leu Glu Ser Trp Gly Ala Ala Lys Pro Phe Ala
            100                 105

<210> SEQ ID NO 96
<211> LENGTH: 109
<212> TYPE: PRT
<213> ORGANISM: Rat

<400> SEQUENCE: 96

Lys Trp Gln Tyr Asp Val Trp Ser His Asp Val Thr Leu Ala Asn His
1               5                   10                  15

Met Glu Ala Gly Gly Val Pro Gly Arg Val His Ile Thr Gly Ala Thr
            20                  25                  30

Leu Ala Leu Leu Ala Gly Ala Tyr Ala Val Glu Arg Ala Asp Met Glu
        35                  40                  45

His Arg Asp Pro Tyr Leu Arg Glu Leu Gly Glu Pro Thr Tyr Leu Val
    50                  55                  60

Ile Asp Pro Trp Ala Glu Glu Asp Glu Lys Gly Thr Glu Arg Gly
65                  70                  75                  80

Leu Leu Ser Ser Leu Glu Gly His Thr Met Arg Pro Ser Leu Leu Met
                85                  90                  95

Thr Arg Tyr Leu Glu Ser Trp Gly Ala Ala Lys Pro Phe
            100                 105

<210> SEQ ID NO 97
<211> LENGTH: 114
<212> TYPE: PRT
<213> ORGANISM: Rat

<400> SEQUENCE: 97

Lys Trp Gln Tyr Asp Val Trp Ser His Asp Val Ser Leu Ala Asn Arg
1               5                   10                  15

Met Glu Ala Ala Gly Val Pro Gly Arg Val His Ile Thr Glu Ala Thr
            20                  25                  30

Leu Asn His Leu Asp Lys Ala Tyr Glu Val Glu Asp Gly His Gly Glu
        35                  40                  45

Gln Arg Asp Pro Tyr Leu Lys Glu Met Asn Ile Arg Thr Tyr Leu Val
    50                  55                  60

```
Ile Asp Pro Arg Ser Gln Gln Pro Pro Pro Ser His His Leu Ser
 65                  70                  75                  80

Lys Pro Lys Gly Asp Lys Ala Thr Leu Lys Met Arg Ala Ser Val Arg
                 85                  90                  95

Val Thr Arg Tyr Leu Glu Ser Trp Gly Ala Ala Arg Pro Phe Ala His
                100                 105                 110

Leu Asn

<210> SEQ ID NO 98
<211> LENGTH: 5515
<212> TYPE: DNA
<213> ORGANISM: Human
<220> FEATURE:
<221> NAME/KEY: CDS
<222> LOCATION: (539)..(4600)

<400> SEQUENCE: 98
gcggccgcgg cgggagcggc ggcgcactcg gggggaagca ggccccacta gacgggccgc      60
gccgacgggc tccgcgcact cgcagcccgg ggcgccccca cccccagcgc cgccgccgc     120 gggcagggcc ggcccggagc gcgggggggcg gccggggagc gcgggccggg ggcgcccgcc    180
gaagctcgct gctccgggtc ggggtcgggg ccggggccgg ccgcgcgccg cctttgacgc    240
atcggagcgc ggctcctgca ggatggaggg ctccgcgccg ccagcggagt tgtttgtgcg    300
caggcggctc gcggggctgg gagcgctcaa ggtctgaact tccctccgga gccgcagctg    360
gaggaggcga gcgcgcgagg aggagaagcc gcgcggcgcg gaggccaccc tcggggcgag    420
aggcgcggaa ggcgagcgag caaagcggtc ccggagccac ggcggccacg cggcggggac    480
ccccgggcgt tctaggtact ggtgaccccg gccggggcag gccccgggac tcgacaac     538 atg gct tcc ccg ccc cac cag cag ctg ctg cat cac cac agc acc gag     586
Met Ala Ser Pro Pro His Gln Gln Leu Leu His His His Ser Thr Glu
  1               5                  10                  15 gtg agc tgc gac tcc agc ggg gac agc aac agc gtg cgc gtc aag atc     634
Val Ser Cys Asp Ser Ser Gly Asp Ser Asn Ser Val Arg Val Lys Ile
             20                  25                  30 aac ccc aag cag ctg tcc tcc aac agc cac ccc aag cac tgc aaa tac     682
Asn Pro Lys Gln Leu Ser Ser Asn Ser His Pro Lys His Cys Lys Tyr
         35                  40                  45 agc atc tcc tct agc tgc agc agc tct ggg gac tcc ggg ggc gtc ccc     730
Ser Ile Ser Ser Ser Cys Ser Ser Ser Gly Asp Ser Gly Gly Val Pro
     50                  55                  60 cgg cga gtg ggc ggc gga ggc cgg ctg cgc agg cag aag aag ctg ccc     778
Arg Arg Val Gly Gly Gly Gly Arg Leu Arg Arg Gln Lys Lys Leu Pro
 65                  70                  75                  80 cag ctg ttc gag agg gcc tcc agc cgc tgg tgg gac ccc aag ttc gac     826
Gln Leu Phe Glu Arg Ala Ser Ser Arg Trp Trp Asp Pro Lys Phe Asp
                 85                  90                  95 tcg gtg aac ctg gag gag gcc tgc ctg gag cgc tgc ttc ccg cag acc     874
Ser Val Asn Leu Glu Glu Ala Cys Leu Glu Arg Cys Phe Pro Gln Thr
                100                 105                 110 cag cgc cgg ttc cgg tat gcg ctc ttc tac atc ggc ttc gcc tgc ctt     922
Gln Arg Arg Phe Arg Tyr Ala Leu Phe Tyr Ile Gly Phe Ala Cys Leu
            115                 120                 125 ctg tgg agc atc tat ttt gcg gtc cac atg aga tcc aga ctg atc gtc     970
Leu Trp Ser Ile Tyr Phe Ala Val His Met Arg Ser Arg Leu Ile Val
        130                 135                 140 atg gtc gcc ccc gcg ctg tgc ttc ctc ctg gtg tgt gtg ggc ttc ttt    1018
Met Val Ala Pro Ala Leu Cys Phe Leu Leu Val Cys Val Gly Phe Phe
```

```
                145                 150                 155                 160
ctg ttt acc ttc acc aag ctg tac gcc cgg cat tac gcg tgg acc tcg        1066
Leu Phe Thr Phe Thr Lys Leu Tyr Ala Arg His Tyr Ala Trp Thr Ser
                    165                 170                 175 ctg gct ctc acc ctg ctg gtg ttc gcc ctg acc ctg gct gcg cag ttc        1114
Leu Ala Leu Thr Leu Leu Val Phe Ala Leu Thr Leu Ala Ala Gln Phe
                180                 185                 190 cag gtc ttg acg cct gtc tca gga cgc ggc gac agc tcc aac ctt acg        1162
Gln Val Leu Thr Pro Val Ser Gly Arg Gly Asp Ser Ser Asn Leu Thr
            195                 200                 205 gcc aca gcc cgg ccc aca gat act tgc tta tct caa gtg ggg agc ttc        1210
Ala Thr Ala Arg Pro Thr Asp Thr Cys Leu Ser Gln Val Gly Ser Phe
        210                 215                 220 tcc atg tgc atc gaa gtg ctc ttt ttg ctc tat acc gtc atg cac tta        1258
Ser Met Cys Ile Glu Val Leu Phe Leu Leu Tyr Thr Val Met His Leu
225                 230                 235                 240 cct ttg tac ctg agt ttg tgt ctg ggg gtg gcc tac tct gtc ctt ttc        1306
Pro Leu Tyr Leu Ser Leu Cys Leu Gly Val Ala Tyr Ser Val Leu Phe
                245                 250                 255 gag acc ttt ggc tac cat ttc cgg gat gaa gcc tgc ttc ccc tcg ccc        1354
Glu Thr Phe Gly Tyr His Phe Arg Asp Glu Ala Cys Phe Pro Ser Pro
            260                 265                 270 gga gcc ggg gcc ctg cac tgg gag ctg ctg agc agg ggg ctg ctc cac        1402
Gly Ala Gly Ala Leu His Trp Glu Leu Leu Ser Arg Gly Leu Leu His
        275                 280                 285 ggc tgc atc cac gcc atc ggg gtc cac ctg ttc gtc atg tcc cag gtg        1450
Gly Cys Ile His Ala Ile Gly Val His Leu Phe Val Met Ser Gln Val
290                 295                 300 agg tcc agg agc acc ttc ctc aag gtg ggg caa tcc att atg cac ggg        1498
Arg Ser Arg Ser Thr Phe Leu Lys Val Gly Gln Ser Ile Met His Gly
305                 310                 315                 320 aag gac ctg gaa gtg gaa aaa gcc ctc aaa gag agg atg att cat tcc        1546
Lys Asp Leu Glu Val Glu Lys Ala Leu Lys Glu Arg Met Ile His Ser
                325                 330                 335 gtg atg cca aga atc ata gcc gat gac tta atg aag cag gga gat gag        1594
Val Met Pro Arg Ile Ile Ala Asp Asp Leu Met Lys Gln Gly Asp Glu
            340                 345                 350 gag agt gag aat tct gtc aag aga cat gcc acc tcg agc ccc aag aac        1642
Glu Ser Glu Asn Ser Val Lys Arg His Ala Thr Ser Ser Pro Lys Asn
        355                 360                 365 agg aag aaa aag tct tcc atc caa aaa gct cct ata gcc ttc cgc cct        1690
Arg Lys Lys Lys Ser Ser Ile Gln Lys Ala Pro Ile Ala Phe Arg Pro
    370                 375                 380 ttt aag atg cag cag atc gaa gaa gtc agt att tta ttt gca gat atc        1738
Phe Lys Met Gln Gln Ile Glu Glu Val Ser Ile Leu Phe Ala Asp Ile
385                 390                 395                 400 gtg ggc ttc acc aag atg agt gcc aac aag tct gcc cac gcc ctg gtg        1786
Val Gly Phe Thr Lys Met Ser Ala Asn Lys Ser Ala His Ala Leu Val
                405                 410                 415 ggt ctc ctg aac gat ctg ttc ggt cgc ttc gac cgc ctg tgt gag gag        1834
Gly Leu Leu Asn Asp Leu Phe Gly Arg Phe Asp Arg Leu Cys Glu Glu
            420                 425                 430 acc aag tgt gag aaa atc agc acc ctg gga gac tgt tac tac tgc gtg        1882
Thr Lys Cys Glu Lys Ile Ser Thr Leu Gly Asp Cys Tyr Tyr Cys Val
        435                 440                 445 gcg ggc tgt ccc gag ccc cgg gcc gac cat gcc tac tgc tgc atc gag        1930
Ala Gly Cys Pro Glu Pro Arg Ala Asp His Ala Tyr Cys Cys Ile Glu
    450                 455                 460 atg ggc ctg ggc atg atc aag gcc atc gag cag ttc tgc cag gag aag        1978
```

```
                                                                           -continued Met Gly Leu Gly Met Ile Lys Ala Ile Glu Gln Phe Cys Gln Glu Lys
465                 470                 475                 480 aag gag atg gtg aac atg aga gtc ggg gtg cac acg cgc acc gtc ctt    2026
Lys Glu Met Val Asn Met Arg Val Gly Val His Thr Arg Thr Val Leu
                485                 490                 495 tgc ggc atc ctg ggc atg agg agg ttt aaa ttt gac gtg tgg tcc aac    2074
Cys Gly Ile Leu Gly Met Arg Arg Phe Lys Phe Asp Val Trp Ser Asn
            500                 505                 510 gat gtg aac ctg gcc aat ctc atg gag cag ctg gga gtg gcc ggc aaa    2122
Asp Val Asn Leu Ala Asn Leu Met Glu Gln Leu Gly Val Ala Gly Lys
        515                 520                 525 gtt cac att tct gag gcc acc gca aaa tac tta gat gac cgg tac gaa    2170
Val His Ile Ser Glu Ala Thr Ala Lys Tyr Leu Asp Asp Arg Tyr Glu
    530                 535                 540 atg gaa gat ggg aaa gtt att gaa cgg ctg ggc cag agc gtg gtt gct    2218
Met Glu Asp Gly Lys Val Ile Glu Arg Leu Gly Gln Ser Val Val Ala
545                 550                 555                 560 gac cag ttg aaa ggt ttg aag aca tac ctg ata tcg ggt cag aga gcc    2266
Asp Gln Leu Lys Gly Leu Lys Thr Tyr Leu Ile Ser Gly Gln Arg Ala
                565                 570                 575 aag gag tct cgc tgc agc tgt gca gag gcc ttg ctt tct ggc ttt gag    2314
Lys Glu Ser Arg Cys Ser Cys Ala Glu Ala Leu Leu Ser Gly Phe Glu
            580                 585                 590 gtc att gac ggc tca cag gtg tcc tca ggc cct agg gga cag ggg aca    2362
Val Ile Asp Gly Ser Gln Val Ser Ser Gly Pro Arg Gly Gln Gly Thr
        595                 600                 605 gcg tca tca ggg aat gtc agt gac ttg gcg cag act gtc aaa acc ttt    2410
Ala Ser Ser Gly Asn Val Ser Asp Leu Ala Gln Thr Val Lys Thr Phe
    610                 615                 620 gat aac ctt aag acc tgc cct tcg tgc gga atc aca ttt gct ccc aaa    2458
Asp Asn Leu Lys Thr Cys Pro Ser Cys Gly Ile Thr Phe Ala Pro Lys
625                 630                 635                 640 tct gaa gcc ggc gcc gag gga gga gca cct caa aac ggc tgc caa gac    2506
Ser Glu Ala Gly Ala Glu Gly Gly Ala Pro Gln Asn Gly Cys Gln Asp
                645                 650                 655 gag cat aaa aac agc acc aag gct tct gga gga cct aat ccc aaa act    2554
Glu His Lys Asn Ser Thr Lys Ala Ser Gly Gly Pro Asn Pro Lys Thr
            660                 665                 670 cag aac ggg ctc ctc agc cct ccc caa gag gag aag ctc acc aac agt    2602
Gln Asn Gly Leu Leu Ser Pro Pro Gln Glu Glu Lys Leu Thr Asn Ser
        675                 680                 685 cag act tct ctg tgt gag atc ttg cag gag aag gga agg tgg gca ggg    2650
Gln Thr Ser Leu Cys Glu Ile Leu Gln Glu Lys Gly Arg Trp Ala Gly
    690                 695                 700 gtg agc ctg gac cag tcg gct ctc ctt ccg ctg agg ttc aag aac atc    2698
Val Ser Leu Asp Gln Ser Ala Leu Leu Pro Leu Arg Phe Lys Asn Ile
705                 710                 715                 720 cgg gag aaa acg gac gcc cac ttt gtg gac gtt atc aaa gaa gac agc    2746
Arg Glu Lys Thr Asp Ala His Phe Val Asp Val Ile Lys Glu Asp Ser
                725                 730                 735 ctg atg aaa gat tac ttt ttt aag ccg ccc att aat cag ttc agc ctg    2794
Leu Met Lys Asp Tyr Phe Phe Lys Pro Pro Ile Asn Gln Phe Ser Leu
            740                 745                 750 aac ttc ctg gat cag gag ctg gag cga tcc tac agg acc agc tat cag    2842
Asn Phe Leu Asp Gln Glu Leu Glu Arg Ser Tyr Arg Thr Ser Tyr Gln
        755                 760                 765 gaa gag gtc ata aag aac tcc ccc gtg aag acg ttt gct agt ccc acc    2890
Glu Glu Val Ile Lys Asn Ser Pro Val Lys Thr Phe Ala Ser Pro Thr
    770                 775                 780
```

-continued

| | |
|---|---|
| ttc agc tcc ctc ctg gat gtg ttt ctg tcg acc aca gtg ttt ctg acg<br>Phe Ser Ser Leu Leu Asp Val Phe Leu Ser Thr Thr Val Phe Leu Thr<br>785                         790                     795                     800 | 2938 |
| ctg tcc acc acc tgc ttc ctg aag tac gag gcg gcc acc gtg cct ccc<br>Leu Ser Thr Thr Cys Phe Leu Lys Tyr Glu Ala Ala Thr Val Pro Pro<br>                805                     810                     815 | 2986 |
| ccg ccc gcc gcc ctg gcg gtc ttc agt gca gcc ctg ctg gag gtg<br>Pro Pro Ala Ala Leu Ala Val Phe Ser Ala Ala Leu Leu Leu Glu Val<br>820                                825                     830 | 3034 |
| ctg tcc ctc gcg gtg tcc atc agg atg gtg ttc ttc ctg gag gac gtc<br>Leu Ser Leu Ala Val Ser Ile Arg Met Val Phe Phe Leu Glu Asp Val<br>                835                     840                     845 | 3082 |
| atg gcc tgc acc aag cgc ctg ctg gag tgg atc gcc ggc tgg cta cca<br>Met Ala Cys Thr Lys Arg Leu Leu Glu Trp Ile Ala Gly Trp Leu Pro<br>850                         855                     860 | 3130 |
| cgt cac tgc atc ggg gcc atc ctg gtg tcg ctt ccc gca ctg gcc gtc<br>Arg His Cys Ile Gly Ala Ile Leu Val Ser Leu Pro Ala Leu Ala Val<br>865                         870                     875                     880 | 3178 |
| tac tcc cat gca acc tcc gaa tat gag acc aac ata cac ttc cca gtg<br>Tyr Ser His Ala Thr Ser Glu Tyr Glu Thr Asn Ile His Phe Pro Val<br>                885                     890                     895 | 3226 |
| ttc aca ggc tcg gcc gcg ctg att gcc gtc gtg cac tac tgt aac ttc<br>Phe Thr Gly Ser Ala Ala Leu Ile Ala Val Val His Tyr Cys Asn Phe<br>                 900                     905                     910 | 3274 |
| tgc cag ctc agc tcc tgg atg agg tcc tcc ctc gcc acc gtc gtg ggg<br>Cys Gln Leu Ser Ser Trp Met Arg Ser Ser Leu Ala Thr Val Val Gly<br>915                         920                     925 | 3322 |
| gcc ggg ccg ctg ctc ctg ctc tac gtc tcc ctg tgc cca gac agt tct<br>Ala Gly Pro Leu Leu Leu Leu Tyr Val Ser Leu Cys Pro Asp Ser Ser<br>930                         935                     940 | 3370 |
| gta tta act tcg ccc ctt gac gca gta cag aat ttc agt tcc gag agg<br>Val Leu Thr Ser Pro Leu Asp Ala Val Gln Asn Phe Ser Ser Glu Arg<br>945                         950                     955                     960 | 3418 |
| aac ccg tgc aat agt tcg gtg ccg cgt gac ctc cgg cgg ccc gcc agc<br>Asn Pro Cys Asn Ser Ser Val Pro Arg Asp Leu Arg Arg Pro Ala Ser<br>                965                     970                     975 | 3466 |
| ctc atc ggc cag gag gtg gtt ctc gtc ttc ttt ctc ctg ctc ttg ttg<br>Leu Ile Gly Gln Glu Val Val Leu Val Phe Phe Leu Leu Leu Leu Leu<br>                 980                     985                     990 | 3514 |
| gtc tgg ttc ctg aat cgc gaa ttt gaa gtc agc tac cgc ctc cac tac<br>Val Trp Phe Leu Asn Arg Glu Phe Glu Val Ser Tyr Arg Leu His Tyr<br>               995                    1000                  1005 | 3562 |
| cac gga gac gtg gaa gcg gat ctt cac cgc acc aag atc cag agc atg<br>His Gly Asp Val Glu Ala Asp Leu His Arg Thr Lys Ile Gln Ser Met<br>1010                     1015                  1020 | 3610 |
| cgg gac cag gca gac tgg ctg ctg agg aac atc atc ccc tac cac gtg<br>Arg Asp Gln Ala Asp Trp Leu Leu Arg Asn Ile Ile Pro Tyr His Val<br>1025                   1030                  1035                  1040 | 3658 |
| gct gag cag ctg aag gtg tcc cag acc tac tcc aag aac cac gac agc<br>Ala Glu Gln Leu Lys Val Ser Gln Thr Tyr Ser Lys Asn His Asp Ser<br>                1045                  1050                  1055 | 3706 |
| gga ggg gtg atc ttc gcc agc atc gtc aac ttc agc gag ttc tac gag<br>Gly Gly Val Ile Phe Ala Ser Ile Val Asn Phe Ser Glu Phe Tyr Glu<br>                1060                  1065                  1070 | 3754 |
| gag aac tac gag ggc ggc aag gag tgc tac cgg gtc ctc aac gag ctc<br>Glu Asn Tyr Glu Gly Gly Lys Glu Cys Tyr Arg Val Leu Asn Glu Leu<br>1075                     1080                  1085 | 3802 |
| atc ggg gac ttt gac gag ctc cta agc aag ccg gac tac agc agc atc<br>Ile Gly Asp Phe Asp Glu Leu Leu Ser Lys Pro Asp Tyr Ser Ser Ile<br>                1090                  1095                  1100 | 3850 |

```
gag aag atc aag acc atc gga gcc acg tac atg gcg gcg tca ggg ctg    3898
Glu Lys Ile Lys Thr Ile Gly Ala Thr Tyr Met Ala Ala Ser Gly Leu
1105            1110            1115            1120 aac acc gcg cag gcc cag gac ggc agc cac ccg cag gag cac ctg cag    3946
Asn Thr Ala Gln Ala Gln Asp Gly Ser His Pro Gln Glu His Leu Gln
        1125            1130            1135 atc ctg ttc gag ttc gcc aag gag atg atg cgc gtg gtg gac gac ttc    3994
Ile Leu Phe Glu Phe Ala Lys Glu Met Met Arg Val Val Asp Asp Phe
    1140            1145            1150 aac agc aac atg ctg tgg ttc aac ttc aag ctc cgc gtc ggc ttc aac    4042
Asn Ser Asn Met Leu Trp Phe Asn Phe Lys Leu Arg Val Gly Phe Asn
1155            1160            1165 cat ggg ccc ctc acg gcc ggg gtc atc ggc acc acc aag ctg ctg tac    4090
His Gly Pro Leu Thr Ala Gly Val Ile Gly Thr Thr Lys Leu Leu Tyr
        1170            1175            1180 gac atc tgg gga gac acc gtc aac atc gcc agc agg atg gac acc acc    4138
Asp Ile Trp Gly Asp Thr Val Asn Ile Ala Ser Arg Met Asp Thr Thr
1185            1190            1195            1200 ggc gtg gag tgc cgc atc cag gtg agc gaa gag agc tac cgc gtc ttg    4186
Gly Val Glu Cys Arg Ile Gln Val Ser Glu Glu Ser Tyr Arg Val Leu
        1205            1210            1215 agc aag atg ggc tat gac ttc gac tac aga ggg acc gtg aat gtc aag    4234
Ser Lys Met Gly Tyr Asp Phe Asp Tyr Arg Gly Thr Val Asn Val Lys
    1220            1225            1230 ggg aaa ggc cag atg aag acc tac ctg tac cca aag tgc acg gat cac    4282
Gly Lys Gly Gln Met Lys Thr Tyr Leu Tyr Pro Lys Cys Thr Asp His
1235            1240            1245 agg gtc atc cca cag cac cag ctg tcc atc tcc cca gac atc cgc gtc    4330
Arg Val Ile Pro Gln His Gln Leu Ser Ile Ser Pro Asp Ile Arg Val
        1250            1255            1260 cag gtg gat ggc agc atc gga cgg tct ccc aca gac gag att gcc aac    4378
Gln Val Asp Gly Ser Ile Gly Arg Ser Pro Thr Asp Glu Ile Ala Asn
1265            1270            1275            1280 ctg gtg cct tct gtc cag tat gtg gac aag aca tct ctg ggt tct gac    4426
Leu Val Pro Ser Val Gln Tyr Val Asp Lys Thr Ser Leu Gly Ser Asp
        1285            1290            1295 agc agc acg cag gcc aag gat gcc cac ctg tcc cgc aag aga ccg tgg    4474
Ser Ser Thr Gln Ala Lys Asp Ala His Leu Ser Arg Lys Arg Pro Trp
    1300            1305            1310 aag gag ccc gtc aaa gcc gaa gaa agg ggt cga ttt ggc aaa gcc ata    4522
Lys Glu Pro Val Lys Ala Glu Glu Arg Gly Arg Phe Gly Lys Ala Ile
1315            1320            1325 gag aaa gac gac tgt gac gaa aca gga ata gaa gaa gcc aac gaa ctc    4570
Glu Lys Asp Asp Cys Asp Glu Thr Gly Ile Glu Glu Ala Asn Glu Leu
        1330            1335            1340 acc aag ctc aac gtt tca aag agt gtg tga ggcggcgccc acccgctgcc     4620
Thr Lys Leu Asn Val Ser Lys Ser Val
1345            1350 cgaggtgctc tgtttgtcga aacacagtaa tatttgtatt tggctgttgt gctttccaag   4680
cgccacagtt gccctccccg gacgtggtgt tatgtggtca tttcagccct aacttctgtg   4740
tggatcacag ttattcaggg ttcatttttca tccattcttc cctttcgctc ccttccctgg  4800 aaacccgct gcctctgggt catccgttca gcacgtggtg gagaacaagt gccttcaggg    4860
ctggcctcgg cctcgagtct cgggacagag gccgccagtg gagatcatgg ctttgggtat   4920
tatttgactt ttagaacaaa agctgtggtt aagatctcat ttttattgct ttttcccacg   4980
tcccacgaga cactatttcc ggttctctgg ctaatacccc gtttttgagt ttattttgtt   5040
```

-continued

```
tctgtctatg tcacagtgtt cctctacgac ccgacctctc tatgtaagca cacatgcgca    5100
cacacacttg cattcatgaa tctgatataa agtgccagta atccgccaag agggggtgcg    5160
aagggggcat gtcacgacag ctccgccacc ccccattgcc cacccgcact ttcccgagca    5220
ccgcgccccg tgggctgtgg gtgagccgcg ctccctgcac tgagcgggtt tagggctcg     5280 cccacatgca tgcaggccaa gacagcaaat gccagccggg cacgacgccc gtgtgcccag    5340
gcctcggggg tctcagagcc gcctctcacc cccgaccctc cacccagggg tcttcccgtc    5400
gggagtggag gcgttggtcc tggaagctga ctcatcggag agggaaatac caaataaaca    5460
tccgaggttg caaaaaaaaa aaaaaaaaa aaaaaaaaaa aaaaagcgcg gccgc          5515
```

<210> SEQ ID NO 99
<211> LENGTH: 1353
<212> TYPE: PRT
<213> ORGANISM: Human

<400> SEQUENCE: 99

```
Met Ala Ser Pro Pro His Gln Gln Leu Leu His His Ser Thr Glu
  1               5                  10                  15

Val Ser Cys Asp Ser Ser Gly Asp Ser Asn Ser Val Arg Val Lys Ile
                 20                  25                  30

Asn Pro Lys Gln Leu Ser Ser Asn Ser His Pro Lys His Cys Lys Tyr
             35                  40                  45

Ser Ile Ser Ser Ser Cys Ser Ser Gly Asp Ser Gly Val Pro
         50                  55                  60

Arg Arg Val Gly Gly Gly Gly Arg Leu Arg Arg Gln Lys Lys Leu Pro
 65                  70                  75                  80

Gln Leu Phe Glu Arg Ala Ser Ser Arg Trp Trp Asp Pro Lys Phe Asp
                     85                  90                  95

Ser Val Asn Leu Glu Glu Ala Cys Leu Glu Arg Cys Phe Pro Gln Thr
                100                 105                 110

Gln Arg Arg Phe Arg Tyr Ala Leu Phe Tyr Ile Gly Phe Ala Cys Leu
             115                 120                 125

Leu Trp Ser Ile Tyr Phe Ala Val His Met Arg Ser Arg Leu Ile Val
130                 135                 140

Met Val Ala Pro Ala Leu Cys Phe Leu Val Cys Val Gly Phe Phe
145                 150                 155                 160

Leu Phe Thr Phe Thr Lys Leu Tyr Ala Arg His Tyr Ala Trp Thr Ser
                165                 170                 175

Leu Ala Leu Thr Leu Leu Val Phe Ala Leu Thr Leu Ala Ala Gln Phe
                180                 185                 190

Gln Val Leu Thr Pro Val Ser Gly Arg Gly Asp Ser Ser Asn Leu Thr
            195                 200                 205

Ala Thr Ala Arg Pro Thr Asp Thr Cys Leu Ser Gln Val Gly Ser Phe
        210                 215                 220

Ser Met Cys Ile Glu Val Leu Phe Leu Leu Tyr Thr Val Met His Leu
225                 230                 235                 240

Pro Leu Tyr Leu Ser Leu Cys Leu Gly Val Ala Tyr Ser Val Leu Phe
                245                 250                 255

Glu Thr Phe Gly Tyr His Phe Arg Asp Glu Ala Cys Phe Pro Ser Pro
                260                 265                 270

Gly Ala Gly Ala Leu His Trp Glu Leu Leu Ser Arg Gly Leu Leu His
            275                 280                 285

Gly Cys Ile His Ala Ile Gly Val His Leu Phe Val Met Ser Gln Val
```

-continued

```
                290                 295                 300
Arg Ser Arg Ser Thr Phe Leu Lys Val Gly Gln Ser Ile Met His Gly
305                 310                 315                 320
Lys Asp Leu Glu Val Glu Lys Ala Leu Lys Glu Arg Met Ile His Ser
                325                 330                 335
Val Met Pro Arg Ile Ile Ala Asp Asp Leu Met Lys Gln Gly Asp Glu
                340                 345                 350
Glu Ser Glu Asn Ser Val Lys Arg His Ala Thr Ser Ser Pro Lys Asn
                355                 360                 365
Arg Lys Lys Lys Ser Ser Ile Gln Lys Ala Pro Ile Ala Phe Arg Pro
370                 375                 380
Phe Lys Met Gln Gln Ile Glu Glu Val Ser Ile Leu Phe Ala Asp Ile
385                 390                 395                 400
Val Gly Phe Thr Lys Met Ser Ala Asn Lys Ser Ala His Ala Leu Val
                405                 410                 415
Gly Leu Leu Asn Asp Leu Phe Gly Arg Phe Asp Arg Leu Cys Glu Glu
                420                 425                 430
Thr Lys Cys Glu Lys Ile Ser Thr Leu Gly Asp Cys Tyr Tyr Cys Val
                435                 440                 445
Ala Gly Cys Pro Glu Pro Arg Ala Asp His Ala Tyr Cys Cys Ile Glu
450                 455                 460
Met Gly Leu Gly Met Ile Lys Ala Ile Glu Gln Phe Cys Gln Glu Lys
465                 470                 475                 480
Lys Glu Met Val Asn Met Arg Val Gly Val His Thr Arg Thr Val Leu
                485                 490                 495
Cys Gly Ile Leu Gly Met Arg Arg Phe Lys Phe Asp Val Trp Ser Asn
                500                 505                 510
Asp Val Asn Leu Ala Asn Leu Met Glu Gln Leu Gly Val Ala Gly Lys
                515                 520                 525
Val His Ile Ser Glu Ala Thr Ala Lys Tyr Leu Asp Asp Arg Tyr Glu
530                 535                 540
Met Glu Asp Gly Lys Val Ile Glu Arg Leu Gly Gln Ser Val Val Ala
545                 550                 555                 560
Asp Gln Leu Lys Gly Leu Lys Thr Tyr Leu Ile Ser Gly Gln Arg Ala
                565                 570                 575
Lys Glu Ser Arg Cys Ser Cys Ala Glu Ala Leu Leu Ser Gly Phe Glu
                580                 585                 590
Val Ile Asp Gly Ser Gln Val Ser Ser Gly Pro Arg Gly Gln Gly Thr
                595                 600                 605
Ala Ser Ser Gly Asn Val Ser Asp Leu Ala Gln Thr Val Lys Thr Phe
610                 615                 620
Asp Asn Leu Lys Thr Cys Pro Ser Cys Gly Ile Thr Phe Ala Pro Lys
625                 630                 635                 640
Ser Glu Ala Gly Ala Glu Gly Gly Ala Pro Gln Asn Gly Cys Gln Asp
                645                 650                 655
Glu His Lys Asn Ser Thr Lys Ala Ser Gly Gly Pro Asn Pro Lys Thr
                660                 665                 670
Gln Asn Gly Leu Leu Ser Pro Pro Gln Glu Glu Lys Leu Thr Asn Ser
                675                 680                 685
Gln Thr Ser Leu Cys Glu Ile Leu Gln Glu Lys Gly Arg Trp Ala Gly
                690                 695                 700
Val Ser Leu Asp Gln Ser Ala Leu Leu Pro Leu Arg Phe Lys Asn Ile
705                 710                 715                 720
```

-continued

```
Arg Glu Lys Thr Asp Ala His Phe Val Asp Val Ile Lys Glu Asp Ser
            725                 730                 735
Leu Met Lys Asp Tyr Phe Phe Lys Pro Pro Ile Asn Gln Phe Ser Leu
            740                 745                 750
Asn Phe Leu Asp Gln Glu Leu Glu Arg Ser Tyr Arg Thr Ser Tyr Gln
            755                 760                 765
Glu Glu Val Ile Lys Asn Ser Pro Val Lys Thr Phe Ala Ser Pro Thr
            770                 775                 780
Phe Ser Ser Leu Leu Asp Val Phe Leu Ser Thr Thr Val Phe Leu Thr
785                 790                 795                 800
Leu Ser Thr Thr Cys Phe Leu Lys Tyr Glu Ala Ala Thr Val Pro Pro
            805                 810                 815
Pro Pro Ala Ala Leu Ala Val Phe Ser Ala Ala Leu Leu Leu Glu Val
            820                 825                 830
Leu Ser Leu Ala Val Ser Ile Arg Met Val Phe Phe Leu Glu Asp Val
            835                 840                 845
Met Ala Cys Thr Lys Arg Leu Leu Glu Trp Ile Ala Gly Trp Leu Pro
            850                 855                 860
Arg His Cys Ile Gly Ala Ile Leu Val Ser Leu Pro Ala Leu Ala Val
865                 870                 875                 880
Tyr Ser His Ala Thr Ser Glu Tyr Glu Thr Asn Ile His Phe Pro Val
            885                 890                 895
Phe Thr Gly Ser Ala Ala Leu Ile Ala Val Val His Tyr Cys Asn Phe
            900                 905                 910
Cys Gln Leu Ser Ser Trp Met Arg Ser Ser Leu Ala Thr Val Val Gly
            915                 920                 925
Ala Gly Pro Leu Leu Leu Leu Tyr Val Ser Leu Cys Pro Asp Ser Ser
            930                 935                 940
Val Leu Thr Ser Pro Leu Asp Ala Val Gln Asn Phe Ser Ser Glu Arg
945                 950                 955                 960
Asn Pro Cys Asn Ser Ser Val Pro Arg Asp Leu Arg Arg Pro Ala Ser
            965                 970                 975
Leu Ile Gly Gln Glu Val Val Leu Val Phe Leu Leu Leu Leu Leu Leu
            980                 985                 990
Val Trp Phe Leu Asn Arg Glu Phe Glu Val Ser Tyr Arg Leu His Tyr
            995                1000                1005
His Gly Asp Val Glu Ala Asp Leu His Arg Thr Lys Ile Gln Ser Met
            1010                1015                1020
Arg Asp Gln Ala Asp Trp Leu Leu Arg Asn Ile Ile Pro Tyr His Val
025                 1030                1035                1040
Ala Glu Gln Leu Lys Val Ser Gln Thr Tyr Ser Lys Asn His Asp Ser
            1045                1050                1055
Gly Gly Val Ile Phe Ala Ser Ile Val Asn Phe Ser Glu Phe Tyr Glu
            1060                1065                1070
Glu Asn Tyr Glu Gly Gly Lys Glu Cys Tyr Arg Val Leu Asn Glu Leu
            1075                1080                1085
Ile Gly Asp Phe Asp Glu Leu Leu Ser Lys Pro Asp Tyr Ser Ser Ile
            1090                1095                1100
Glu Lys Ile Lys Thr Ile Gly Ala Thr Tyr Met Ala Ala Ser Gly Leu
105                 1110                1115                1120
Asn Thr Ala Gln Ala Gln Asp Gly Ser His Pro Gln Glu His Leu Gln
            1125                1130                1135
```

```
Ile Leu Phe Glu Phe Ala Lys Glu Met Met Arg Val Val Asp Asp Phe
        1140                1145                1150

Asn Ser Asn Met Leu Trp Phe Asn Phe Lys Leu Arg Val Gly Phe Asn
        1155                1160                1165

His Gly Pro Leu Thr Ala Gly Val Ile Gly Thr Thr Lys Leu Leu Tyr
    1170                1175                1180

Asp Ile Trp Gly Asp Thr Val Asn Ile Ala Ser Arg Met Asp Thr Thr
185                 1190                1195                1200

Gly Val Glu Cys Arg Ile Gln Val Ser Glu Glu Ser Tyr Arg Val Leu
            1205                1210                1215

Ser Lys Met Gly Tyr Asp Phe Asp Tyr Arg Gly Thr Val Asn Val Lys
        1220                1225                1230

Gly Lys Gly Gln Met Lys Thr Tyr Leu Tyr Pro Lys Cys Thr Asp His
    1235                1240                1245

Arg Val Ile Pro Gln His Gln Leu Ser Ile Ser Pro Asp Ile Arg Val
    1250                1255                1260

Gln Val Asp Gly Ser Ile Gly Arg Ser Pro Thr Asp Glu Ile Ala Asn
265                 1270                1275                1280

Leu Val Pro Ser Val Gln Tyr Val Asp Lys Thr Ser Leu Gly Ser Asp
            1285                1290                1295

Ser Ser Thr Gln Ala Lys Asp Ala His Leu Ser Arg Lys Arg Pro Trp
        1300                1305                1310

Lys Glu Pro Val Lys Ala Glu Glu Arg Gly Arg Phe Gly Lys Ala Ile
    1315                1320                1325

Glu Lys Asp Asp Cys Asp Glu Thr Gly Ile Glu Glu Ala Asn Glu Leu
    1330                1335                1340

Thr Lys Leu Asn Val Ser Lys Ser Val
345                 1350

<210> SEQ ID NO 100
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 100
gacctttggc taccatttcc gggatg                                    26

<210> SEQ ID NO 101
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 101
cttcgctcac ctggatgcgg cactc                                     25

<210> SEQ ID NO 102
<211> LENGTH: 19
<212> TYPE: DNA
<213> ORGANISM: Artificial Sequence
<220> FEATURE:
<223> OTHER INFORMATION: Description of Artificial Sequence: Primer
      based on mouse adenyl cyclase 9

<400> SEQUENCE: 102
ggagcgctgc tttccgcag                                            19
```

```
<210> SEQ ID NO 103
<211> LENGTH: 25
<212> TYPE: DNA
<213> ORGANISM: Artificial Sequence
<220> FEATURE:
<223> OTHER INFORMATION: Description of Artificial Sequence: Primer
      based on mouse adenyl cyclase 9

<400> SEQUENCE: 103
catgttcacc atctctttct tctcc                                       25

<210> SEQ ID NO 104
<211> LENGTH: 29
<212> TYPE: DNA
<213> ORGANISM: Artificial Sequence
<220> FEATURE:
<223> OTHER INFORMATION: Description of Artificial Sequence: Primer
      based on mouse adenyl cyclase 9

<400> SEQUENCE: 104
gtggccgtga gagtatgatt ggagctgtc                                   29
```

HUMAN ADENYLATE CYCLASE AND USE THEREFOR

CROSS-REFERENCE TO RELATED APPLICATION

This application is a continuation-in-part of U.S. Ser. No. 08/894,173, filed Aug. 13, 1997, now U.S. Pat. No. 6,090,612, which is a 371 of PCT/GB96/00312, the entire disclosure of which is incorporated by reference herein.

The present invention relates to the control of cellular metabolic process by human adenylate cyclase.

Cells of multi-cellular organisms may be metabolically affected by external factors, which are usually chemical. Hormones are a well-known example of such chemical factors. Generally the external chemical factors interact with a specific receptor located on the membrane of the targeted cell. The binding event of the factor to its receptor may induce alterations in cellular metabolism via a "secondary messenger" mediator.

One of the key "secondary messengers" is cyclic AMP (cAMP) (see Sutherland, Science 177:401–407 (1972)). Cyclic AMP is produced from ATP through the action of an enzyme, adenylate cyclase. It is now known that adenylate cyclase activity may be affected by a factor/receptor binding event transmitted through an associated G protein.

Alteration of the intracellular concentration of cAMP affects many cellular reactions. For example, an increase in cAMP intracellular concentration stimulates the activity of protein kinases (enzymes that transfer terminal phosphate groups from ATP to specific sites on targeted proteins). The action of the protein kinases changes the activity or function of its substrate.

For a general review of cAMP and secondary messenger systems reference is made to "Molecular Cell Biology", Darnell et al, 1986, Chapter 16, incorporated herein by reference.

Further investigations of cAMP as a secondary messenger revealed that an alteration in cAMP intracellular concentration was caused by the interaction of several different external factors with their distinct receptors. Further, it was found that different receptors were associated with their own particular G-protein intermediary which was itself associated with adenylate cyclase. More recent investigations have shown that there are in fact different types (isoenzymes) of adenylate cyclase, which display considerable regulatory diversity.

To date eight distinct isoenzymes of adenylate cyclase have been identified and described in the literature. The complete cDNA sequences are known for isoenzymes types 1 to 8. A review of the current understanding and knowledge of the known adenylate cyclase isoenzymes is set out in Pieroni et al, Current Opinion in Neurobiology 3:345–351 (1993); Kerwin Jr in Annual Reports in Medicinal Chemistry, Section VI, Chapter 29, Pages 287–295 (ed Venuti), (1994) and Premont, Methods in Enzymology 238:116–127 (1994).

A summary of the regulation of the known isoenzymes of adenylate cyclase is set out below in Table 1.

TABLE 1

| Isoenzyme | Regulated by | cAMP concentration |
|---|---|---|
| 1 | $Ca^{2+}$/CaM | ↑ |
|  | β γ dimer | ↓ |
| 2 | $G_{xi}$ + PKC | ↑ |
|  | β γ dimer | ↑ |
|  | PKC | ↑ |
| 3 | $Ca^{2+}$/CaM | ↑ |
| 4 | β γ dimer | ↑ |
| 5 | $Ca^{2+}$ | ↓ |
| 6 | $Ca^{2+}$ | ↓ |

CaM = calmodulin
PCK = protein Kinase C

It has now been found, for the first time, that the protein phosphatase calcineurin regulates an adenylate cyclase isoenzyme.

It has further now been found that the isoenzyme regulated by calcineurin is a novel previously uncharacterised adenylate cyclase isoenzyme. The novel isoenzyme of the present invention was originally referred to as adenylate cyclase 10 (AC10), but a review of nomenclature has now caused the novel adenylate cyclase to be referred to as adenylate cyclase 9 (AC9). To avoid confusion with the different isoenzyme known before the nomenclature revision as "adenylate cyclase 9", the novel adenylate cyclase of the present invention will herein simply be referred to as "AC".

The nucleotide sequence encoding for mouse AC has been identified, cloned and sequenced (see Example 2). The nucleotide sequence encoding for mouse AC is given in SEQ ID No 1. The sequence is also accessible in the Genbank™ database under accession No. MMU30602 and in the EMBL database under accession No. Z50190.

A nucleotide sequence purporting to be that for human AC is described in WO-A-99/01540. The nucleotide sequence presented in WO-A-99/01540 indicates that the C-terminal portion of the protein is truncated relative to that of the mouse. We have now conducted additional work in this area and, surprisingly, have cloned and sequenced a human AC construct which does not have the truncated C-terminal portion reported in WO-A-99/01540. The sequence obtained by us for human AC is set out in SEQ ID No 98.

The present invention therefore provides a polypeptide encoded by the nucleotide sequence of SEQ ID No 98 or as set out in SEQ ID No 99 (or functional equivalents or parts of those sequences).

The term "functional equivalents" is used herein to refer to any modified version of a nucleotide or polypeptide which retains the basic function of its unmodified form. As an example, it is well-known that certain alterations in amino acid or nucleic acid sequences may not affect the polypeptide encoded by that molecule or the function of the polypeptide. It is also possible for deleted versions of a molecule to perform a particular function as well as the original molecule. Even where an alteration does affect whether and to what degree a particular function is performed, such altered molecules are included within the term "functional equivalent" provided that the function of the molecule is not so deleteriously affected as to render the molecule useless for its intended purpose.

Whilst we do not wish to be bound to theoretical considerations, it is believed that calcineurin regulates AC by removal of phosphate group(s) required for the active form of the enzyme. Thus, the adenylate cyclase activity of AC is believed to decrease in the presence of calcineurin.

In a further aspect, therefore, the present invention provides the use of calcineurin in the regulation of adenylate cyclase activity, in particular in the regulation of AC.

The activity of calcineurin is itself enhanced by the presence of $Ca^{2+}$ ions and further enhanced by the additional presence of calmodulin.

In a further aspect, the present invention provides an adenylate cyclase isoenzyme, the activity of which can be regulated by calcineurin.

Desirably the calcineurin regulatable adenylate cyclase isoenzyme is encoded by the nucleotide sequence of SEQ ID No 98, functional equivalents or parts thereof.

In a yet further aspect, the present invention provides a polynucleotide comprising a sequence derived from the sequence set out in SEQ ID No 98 or a part thereof.

The phrase "derived from" includes identical and complementary copies of the sequence of SEQ ID No 1, whether of RNA or DNA and whether in single or double-stranded form. The phrase "derived from" further includes sequences with alterations which (due to the degeneracy of the genetic code) do not affect the amino acid sequence of the polypeptide expressed, as well as sequences modified by deletions, additions or replacements of nucleotide(s) which cause no substantial deleterious affection to function (including the function of the polypeptide expressed).

The polynucleotide of the present invention includes all recombinant constructs comprising a nucleotide sequence of the invention as defined above. Such recombinant constructs may be designed to express only part of AC. The constructs may include expression control sequence(s) which differ to the control sequence(s) naturally adjoining the AC gene. Optionally, the construct may include a non-AC protein encoding region. Thus the recombinant construct includes constructs encoding for chimeric proteins, which comprise at least part of AC or a functional equivalent thereof.

In a particular embodiment, the present invention provides a vector (such as a cloning or expression vector) which comprises a recombinant construct as defined above. Vectors include conventional cloning and expression plasmids for bacterial and yeast host cells as well as virus vectors such as vaccinia, which may be useful for expression in eukaryotic cell lines. Such a vector may be used to transform a suitable host cell (either for cloning or expression purposes) and the transformed host cell also forms a further aspect of the present invention. If the vector produced is comprised only in part of a nucleotide sequence derived from SEQ ID No 1 it may be appropriate to select a host cell type which is compatible with the vector. Mention may be made of prokaryotic host cells such as *E. coli* as well as eukaryotic host cells, including yeasts, algae and fish, insect or mammalian cells in culture. Insect cells may be especially useful where a baculovirus expression system is used. Suitable host cells will be known to those skilled in the art.

As a general reference to genetic engineering techniques, mention may be made of Sambrook, Fritsch, Maniatis, in "Molecular Cloning, a Laboratory Manual", Cold Spring Harbor Laboratory, Cold Spring Harbor, N.Y., 1989; and also to Old and Primrose "Principles of Genetic Manipulation", 5th edition, 1994.

In particular cell lines derived from the human embryonic kidney cell line 293 (HEK293) have been generated and stably express AC. Briefly, the cells were transfected with pcDNA3 containing the full length AC DNA (clone JP 173—see Example 3) and cells were selected on the basis of resistance to G418 antibiotic (0.8 mg/ml) for 4 weeks. Individual clones of resistant cells were expanded and tested for cAMP production in response to CRF and the effects of immunosuppressants were also examined. At least three cell lines exhibited cAMP production in response to CRF which was enhanced by both cyclosporin A and FK506. In the case of FK506, this effect is blocked by L-685,818. Furthermore, the accumulation of cAMP in the presence of inhibitors of phosphodiesterase is about 10-fold higher than in wild type HEK293 cells. This latter finding suggests that the transfected cyclase is constitutively active and thus may be a mutant of the wild type enzyme.

In a yet further aspect, the present invention provides regulators of AC. Such regulators may act directly on AC itself, and may include (but are not limited to) calcineurin and antibodies specific to AC, or may affect production of AC, including (for example) antisense oligonucleotides (which prevent expression of the AC gene by binding to a portion of DNA preventing transcription and/or by binding to the mRNA preventing translation), and agents which bind to receptors and thus affect the activity of AC, for example β-adrenergic agonists and β-adrenergic antagonists. As β-adrenergic agonists mention may be made of salbutamol, clenbuterol, fenoterol and the like, whereas suitable β-adrenergic antagonists include propranolol.

Antibodies (including monoclonal antibodies) specific to AC may be produced using conventional immunological techniques.

In a yet further aspect, the present invention provides a method of regulating cellular metabolism, wherein said method comprises altering the activity or amount of AC. For example, the activity or amount of AC may be influenced by the regulators described above. Alternatively, for example, the amount of AC could be controlled through genetic manipulation of the genome, by providing agents that affect transcription and/or translation of the AC gene.

The distribution of AC varies between different tissues or cell types and it is postulated that the intracellular concentration of AC may fluctuate as a result of expression control of the AC gene in response to particular stimuli.

Figure 17:
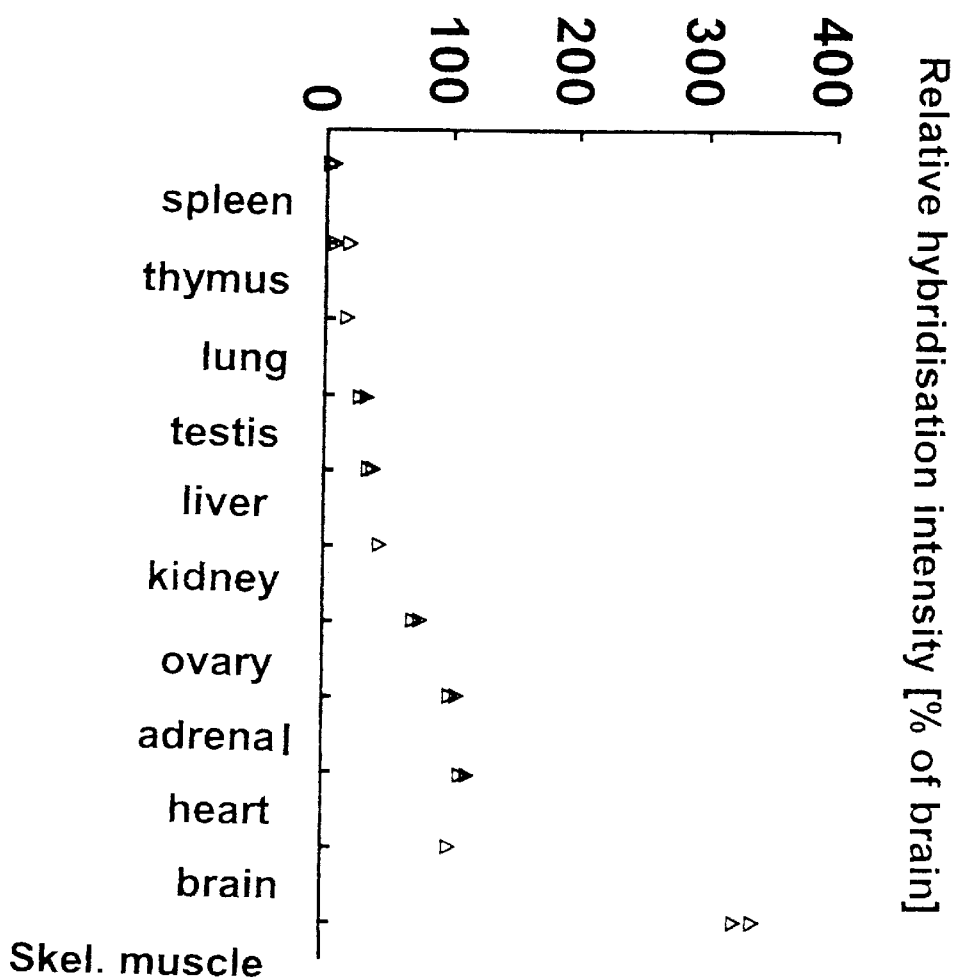

Studies of AC distribution in tissues suggest that it is prominently present in skeletal muscle and heart (FIG. 17). Its likely function in these tissues is the coordination between contraction and metabolic demand. Intracellular calcium ions promote contraction, and cAMP promotes glycogenolysis. Feedback of calcium ions on cAMP synthesis would delimit the accumulation of calcium and ensure that the contractions are no longer than what can be metabolically tolerated by the cells. In this respect it is plausible that the levels of cyclase will be regulated by the trophic state of the muscle such as that seen in the training of sportsmen and animals such as racing horses. Thus the measurement of AC levels by means of specific probes would constitute a means of predicting optimal regulation of contraction and metabolism of nutrients.

Thus for example AC may be present at abnormal levels in certain disease states or conditions. Mention may be made in this regard of neurological-based disorders (for example Parkinson's disease, epilepsy), psychiatrically-based disorders (for example, anxiety, major depression disorder, mania, schizophrenia, obsessive-compulsive disorder, Tourette's Syndrome and related tics) endocrine-based disorders (for example Cushing's Syndrome and disease, Nelson's Syndrome, Cohn's Syndrome, glucocorticoid resistance, Graves' disease (thyrotoxicosis) with or without exophthalmia, hyper and hypothyroidism; hyperprolactinaemia and its effects); hypertrophy of the prostate; cardiovascular-based disorders (for example, angina pectoris, cardiac infarction, hypertension (benign and malignant)), pregnancy-based disorders (for example, recurrent spontaneous abortion, pre-eclampsia and eclampsia) respiratory-based disorders (for example, asthma, bronchitis, chronic bronchitis emphysema and cor pulmonale), bone-based disorders (for example, hyperparathyroidism, osteomalacia, Paget's disease, osteoporosis), promotion of bone healing, kidney-based disorders (for example, acute and chronic glomerular nephritis, Albright's Syndrome—or the McCune Albright's Syndrome), gut-based disorders (for example, ulcerative colitis, irritable bowel, Crohn's disease, Hirschssprung's disease), tumours (benign and malignant), especially ovarian tumours and prostate tumours, and in the control or promotion of fertility. AC has been found to be of greater prevalence in the brain (in particular the cortex, striatum and hippocampus regions of the brain), in the ovaries and in the lungs.

Finally, substances developed to regulate the activity of this cyclase may be useful as improvers of metabolic balance in ischemic heart muscle and syndromes of skeletal muscle atrophy.

In a further aspect, therefore, the present invention provides a method of treating such conditions by control of AC activity. An example of such control could be the design of compounds that mimic the steric conformation of amino acids in positions 503 to 610, especially 503 to 570, of SEQ ID No 99 which may function as a calcineurin binding-site.

The amino acid sequence of human AC has been analysed (analogously to that of the mouse sequence in Example 3) and a domain corresponding to the immunophilin protein FKBP12 (which potently inhibits calcineurin) has been located in residues 594 to 611. The sequence similarity strongly suggests that this is the calcineurin binding site.

Figure 15A:
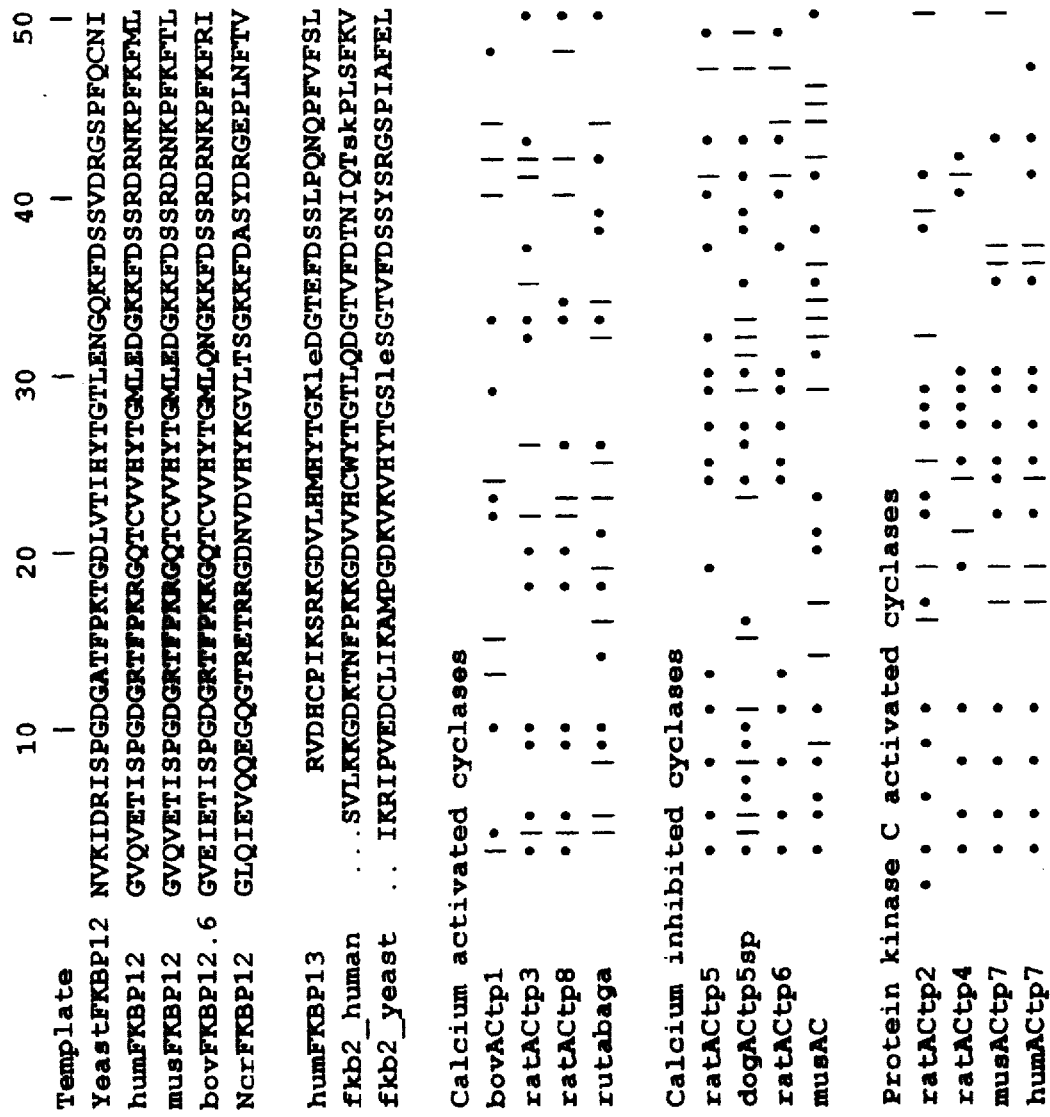
Figure 15B:
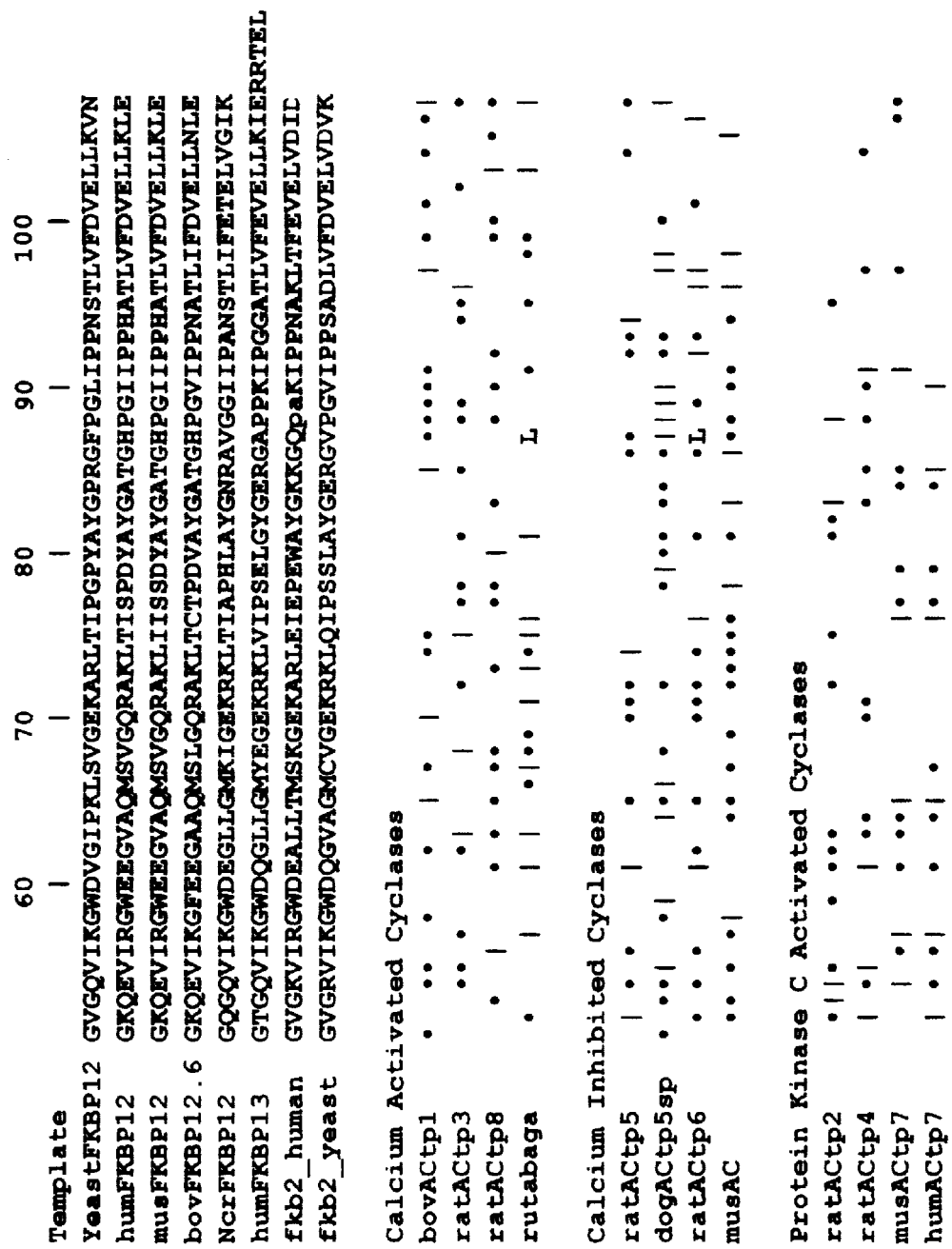

Other adenylyl cyclases were also examined for potential sequence similarities with the FKPB12 and 13 proteins as described in Example 3. A summary of the findings is shown in FIG. 15. Briefly, all of the known adenylyl cyclase sequences appear to show significant similarity with FKBPs in the area that corresponds to the junction of the C1α and C1β domains (see Example 3 for nomenclature). As shown in FIG. 16 the alignments of individual cyclases with FKBP12 are distinct i.e. different portions of the C1α high homology region are part of the FKBP like sequence. These alignments are possible because of modular repeats in the cyclase amino acid sequence in this region. The guiding motif for these alignments is the requirement of the presence of an "80s" loop of FKBP12 in a homologous position in the cyclase "FKBP like" sequence (Yang et al, (1993) Journal of the American Chemical Society 115:819–820). It is of note for instance, that ACtypel, a calcium activated adenylyl cyclase contains a significant portion (sequence: FGPLI) of the 80s loop of FKBP12 which is essential for the interaction with calcineurin (Yang et al, 1993 supra).

Taken together with the current knowledge on the regulation of ACtypel it appears that the C1α–C1β junction domain is an important regulatory site of adenylyl cyclase activity. It is proposed that all adenylyl cyclases are regulated by tightly associated calcineurin bound in this region. This association may eventually prove to be dependent on calcium ions. It is also of note that there are potential protein kinase A, CAM kinase II and casein kinase II phosphorylation sites in this area in most adenylyl cyclases, which could be substrates of calcineurin and/or may influence the avidity of association of calcineurin with the cyclases.

The FKBP12 like domain (residues 594–611) of mouse AC has been expressed as a Glutathione-S-transferase (GST) fusion protein in the expression vector pGEX-2T (Pharmacia). The cyclase portion of this fusion protein can be phosphorylated by cAMP dependent protein kinase and dephosphorylated in a calcium dependent manner by calcineurin. These data support the notion that the region of the cyclase described here is a clacineurin binding site and contains phosphorylated amino acids that are substrates for calcineurin.

Data recently published show a remarkable similarity between a phosphorylation site for myotonic dystrophy protein kinase on the β-subunit of the L type skeletal muscle calcium channel (Timchenko et al, (1995) Proceedings of the National Academy of Sciences of the United States of America 92:5366–5370) and the FKBP-like domain of AC as shown below (wherein • shows amino acid identity and | shows functionally conservative subsitutions):

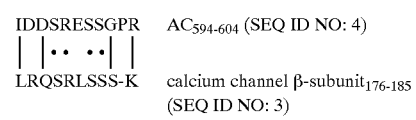

IDDSRESSGPR   $AC_{594-604}$ (SEQ ID NO: 4)

LRQSRLSSS-K   calcium channel β-subunit$_{176-185}$ (SEQ ID NO: 3)

In addition, it has been reported that the calcium β-subunit is selectively dephosphorylated by calcineurin (Lai et al. (1993) Journal of Neurochemistry 61:1333–1339). It is therefore likely that $Ser_{600}$ or $Ser_{601}$ in AC may be phosphorylated by myotonic dystrophy protein kinase and dephosphorylated by calcineurin. Abnormalities in this process may occur in myotonic dystrophy and contribute to the symptoms of this hereditary disorder, especially with respect to the pathological changes of brain, muscle, heart and anterior pituitary function.

In a yet further aspect, the present invention also provides a diagnostic assay, to determine the presence and/or the amount of AC within a sample, said method comprising contacting an agent specific to AC with said sample and determining the presence and/or amount of complex formed. The agent may be, for example, an anti-sense oligonucleotide which is complementary to the mRNA of AC. Alternatively, the agent may be an antibody specific to AC, or may be calcineurin.

In a preferred embodiment the diagnostic agent is immobilised on a support, for example a membrane. Further, it is also preferred that a labelling moiety is present in the assay, so that measurement of the agent/AC complex is simplified.

The present invention will now be further described with reference to the following examples and with references to the accompanying figures in which:

FIG. 1

Effect of FK506, cyclosporin A (CsA) and MeVal$^4$-cyclosporin A (MeVal$^4$CsA) (SDZ202-384) on cAMP accumulation induced by 10 nmol/l CRF in AtT20 cells in the presence of 0.5 mmol/l isobutylmethylxanthine. Basal cAMP production was 0.6±0.08 pmol/well. Data are means±SEM, expressed as percentage of the increment caused by 10 nmol/l CRF which was 6.1 pmol/well.

FIG. 2

A: Effect of cyclosporin A on the time-course of basal and CRF-induced cAMP formation. Data are from a representative of 2 experiments. Means±SEM, n=3 for CRF treated groups (○=10 nmol/l CRF+vehicle, ●=CRF+1 μmol/l cyclosporin A) and n=1 for basal (Δ=vehicle, ▲=cyclosporin A), 0.5 mmol/l IBM, 0.1 mM rolipram and cyclosporin A were given as pre-treatment for 30 minutes at 37° C. before the application of 3 nM CRF for 10 minutesat 24° C.

*P<0.05 compared with respective control group (one way ANOVA followed by orthogonal contrasts).

B: Dependence of the effect of 1 μmol/l FK506 on CRF-induced cAMP formation in the presence of 0.5 mM IBMX. FK506 and IBMX are given as for FIG. 2A. Data are means±SEM, n=4–6/group. (□=FK506 group, Δ=control group)*P<0.05 compared with respective vehicle treated group (one-way ANOVA followed by orthogonal contrasts).

FIG. 3

A: The effect of L685,818 on the enhancement of CRF-induced cAMP formation by FK506. Data are means±SEM, the cAMP level in the presence of 10 nmol/l CRF taken as 100% was 12 pmol/well*10 minutes, basal levels were 1.6 pmol/well*10 minutes.

B: The effect of L685,818 on the inhibition of calcineurin activity by 1 μmol/l FK506 in AtT20 cells. Calcineurin activity was measured by the phosphocasein method, the activity measured in the absence of FK506 was taken as 100%.

FIG. 4

Effects of various manipulations that reduce intracellular free calcium concentration on CRF-induced cAMP accumulation in AtT20 cells. IBMX 0.5 mmol/l present throughout. All data are expressed as the percentage of CRF-induced cAMP-formation, means±SEM, n=4/group.

EGTA: cells exposed to 2 mmol/l EGTA in calcium free medium during the preincubation period; nimodipine: cells exposed to 1 μmol/l nimodipine during preincubation period;

BAPTA-AM: cells incubated in 20 μmol/l [1,2-bis-(o-Aminophenoxy)-ethane-N,N,N',N'-tetraacetic acid tetra-(acetoxymethyl)-ester] during the preincubation period.

FIG. 5

Effect of FK506 on the inhibition of CRF-induced cAMP accumulation by extracellular calcium ions in AtT20 cells. Cells were depleted of calcium by preincubation in 2 mmol/l EGTA, calcium free medium, containing 5 μmol/l A23187 and 5 μmol/l nimodipine, and graded amounts of $CaCl_2$ were added with 10 nmol/l CRF. The values on the abscissa give the nominal free extracellular calcium ion concentration. Data are means±SEM, n=6/group.

FIG. 6

Effect of pertussis toxin (1 μg/ml for 18 hours) on the modulation of CRF-induced cAMP formation by FK506 and somatostatin. AtT20 cells were preincubated with FK506 or somatostatin for 30 minutes. IBMX (0.5 mmol/l) present throughout. Data are means±SEM, n=6/group.

FIG. 7

A: FK506 (0.5 μmol/l) on basal and CRF-induced ACTH secretion in AtT20 cells.

B: Antagonism of the effect of FK506 (0.5 μmol/l) on CRF-induced ACTH release by L685,818, which had no effect on basal ACTH secretion in this system even at 5 μmol/l. n=4/group, means±SEM.

In panel A the values for basal and CRF-stimulated ACTH release taken as 100% were 15±1 and 22±1 fmol/well*30 minutes, respectively.

FIG. 8

Comparison of the sequence (SEQ ID NO: 64) amplified from AtT20 cell RNA using primer set B, with the corresponding sequences with other adenylyl cyclases found in current databases (EMBL, GenBank, SwissProt (SEQ ID NOS: 48 to 64)). The numbers relate to the amino acid sequence of rabbit ACtype5 (ocmradcyv) (SEQ ID NO: 60).

The sequence is annotated by • showing amino acid identity of the novel sequence with at least one previously reported AC, ○ shows funtionally conservative substitutions, – denotes non-conservative subsitutions.

Abbreviations and Sequence Identification Numbers
hum7—Human ACtype7 (GenBank #D25538) (SEQ ID NO: 48);
mmu12919—mouse ACtype7 (SEQ ID NO: 49);
cya2_rat—rat ACtype2 (SEQ ID NO: 50);
cya4_rat—rat ACtype4 (SEQ ID NO: 51);
hsadencyr8—Human ACtype8 (SEQ ID NO: 52);
ratacviii—rat ACtype8 (SEQ ID NO: 53);
a46187—human ACtype5 (SEQ ID NO: 54);
cya6_mouse—mouse ACtype6 (SEQ ID NO: 55);
a49201—mouse ACtype5 (now renamed as mouse AC6) (SEQ ID NO: 56);
cya6_rat—rat ACtype6 (SEQ ID NO: 57);
cya6_canfa—dog ACtype6 (SEQ ID NO: 58);
s29717—rat ACtype5 (SEQ ID NO: 59);
ocmradcyv—rabbit ACtype5 (SEQ ID NO: 60);
cya5_canfa—dog ACtype5 (SEQ ID NO: 61);
cya1_bovin—bovine ACtype1 (SEQ ID NO: 62);
cya3_rat—rat ACtype3 (SEQ ID NO: 63);
AC—AtT20 derived new sequence, ie AC (SEQ ID NO: 64).

FIG. 9

Pileup analysis of adenylyl cyclase sequences found in the EMBL and GenBank data bases.

| legend on dendrogram | adenylyl cyclase isoform |
| --- | --- |
| hum7 | Human type 7 GenBank #D25538; |
| mmu12919 | Mouse type 7; |
| cya2_rat | Rat type 2; |
| cya4_rat | Rat type 4; |
| cya5_canfa | Dog type 5; |
| cya5_rabit | Rabbit type 5; |
| s29717 | Rat type 5; |
| cya6_mouse | Mouse type 6; |
| cya1_bovin | Bovine type 1; |
| ratacviii | Rat type 8; |
| cya3_rat | Rat type 3; |
| Ac | Mouse AC 9, ie AC.-- |

FIG. 10

Hydrophobicity plot of AC according to Kyte et al (1982) J Mol Biol 157:105. The numbers show predicted intramembrane domains.

FIG. 11

Functional Analysis of Cloned AC in Transfected Host Cells

Levels of cAMP in transiently transfected HEK293 (a–c) and COS7 (d) in the presence of phosphodiesterase inhibitors (1 mmol/l isobutylmethylxanthine) and 0.1 mmol/l rolipram). Data shown are means±SEM, n=4/group. Representative data from two similar series of experiments.

(a) HEK293 cells transfected with vector cDNA and pretreated with 0.2% (v/v) ethanol (empty columns) or 2 μmol/l FK506 (striped columns) before being challenged with 0.5 nmol/l CRF.

(b) as (a) except with cells transfected with AC (Data are means±SEM, n=4/group. *P<0.05 when compared with the respective vehicle-treated group, 1-way ANOVA, followed by Newman-Keuls test).

(c) The effect of FK506 on CRF-induced cAMP production was analysed further in (c). The enhancement of the CRF-induced cAMP response by FK506 was blocked by the FK506 antagonist drug L-685,818 (100 μmol/l) (Dumont et al, (1992) J. Exp. Med. 176:751–760), which had no effect on CRF-induced cAMP formation when given alone.

It did, however, similarly to FK506, increase the unstimulated levels of cAMP to 3-fold above basal (not shown). *P<0.05 when compared with the vehicle treated group, 1-way ANOVA, followed by Newman-Keuls test.

(d) Application of cyclosporin A, another calcineurin blocking immunosuppressant enhanced the cAMP response to 1 nmol/l CRF in COS7 cells transfected with AC (*P<0.05, when compared with the vehicle-treated group).

FIG. 12

An FKBP-Like Domain in AC (A) Schematic drawing of the predicted structure of AC, nomenclature as suggested by Gilman and coworkers (Taussig et al, (1995) J. Biol. Chem. 270:1–4). N=N-terminal intracellular loop; M1 and M2=membrane spanning segments; C1α and C2α (thick line)=the highly conserved, putative catalytic cyclase domains; C1β and C2β=the non-conserved, putative regulatory domains of the intracellular loops.

(B) $AC_{(503-610)}$ (SEQ ID NO: 65) shows approximately 40% overall sequence similarity with FK506 binding-protein 12 (FKBP12) (SEQ ID NOs: 66 to 69). Residue numbers in the top row correspond to AC, in the bottom row to mammalian FKBP12s. A dot indicates sequence identity between AC and at least one of the FKBPs. Vertical lines denote conserved substitutions which were defind as 1) C 2) S T P A G 3) N D E Q 4) H R K 5) M I L V 6) F Y W (see Krupinski et al, (1989) Science 244:1558–1564).

yst=Saccharomyces cerevisiae, hum=human, mus=mouse, ncr=Neurospora crassa.

(C) Alignment of the C1α and C1β junction region of known mammalian adenylyl cyclase isotypes (SEQ ID NOs: 70 to 78). The underlined region in bovACtp1 (SEQ ID NO: 70) corresponds to 24 residues of the 28 amino acid residue putative calmodulin binding site (495–522) (Vorherr et al, (1993) Biochemistry (U.S.A.) 32:6081–6088; and Wu et al, (1993) J. Biol. Chem. 286:23766–23768), bov=bovine. Abbreviations as for FIG. 15.

FIG. 13

Northern Analysis of AtT20-Cell, HEK293-Cell and Mouse Striatal RNA $^{32}$P-labelled cDNA probes derived from the AC sequence were used. Note approximately 9 kb band in AtT20 cells that hybridizes with both probes. A similar size RNA species is also intensively hybridizing in mouse striatal RNA and a weak, barely discernible band is found in HEK293 cells. The relative hybridisation intensities (average of the two lanes) with probe jp 164 were: AtT20 2.1; HEK293 0.3; mouse striatum 1.4.

FIG. 14

Localisation of AC mRNA in Mouse Brain

AC mRNA detected by a $^{35}$S-CTP labelled antisense ribonucleic acid probe derived from plasmid JP142 in (A) the hippocampus (pyramidal cell layer of CA1–CA4 (a) and of the subiculum (b), granule cells in dentate gyrus (c) and in various parts of the cereral cortex (posterior cingulate cortex indicated by (d)). (B) $^{35}$S-CTP-sense RNA probe control.

Magnification: 25×.

FIG. 15

An alignment of adenylyl cyclases with FKBPs (SEQ ID NOs: 79 to 86).

• indicates identity; | indicates conserved substitution in at least one of the FKBPs. Conserved substitutions are defined as

1) C
2) STPAG
3) NDEQ
4) HRK
5) MILV
6) FYW

Abbreviations and Sequence Identifiers

| YeastFKBP12 | Yeast FKPB12 (SEQ ID NO: 79) |
| humFKBP12 | human FKBP12 (SEQ ID NO: 80) |
| musFKBP12 | mouse FKBP12 (SEQ ID NO: 81) |
| NcrFKBP12 | Neurospora crassa FKBP 12 (SEQ ID NO: 83) |
| humFKBP13 | human FKBP13 (SEQ ID NO: 84) |
| fkb2__hum | human FKBP13 precursor (SEQ ID NO: 85) |
| fkb2__yeast | yeast FKBP13 (SEQ ID NO: 86) |
| bovACtp1 | bovine adenylyl cyclase type 1 |
| ratACtp3 | rat adenylyl cyclase type 3 |
| ratACtp8 | rat adenylyl cyclase type 8 |
| rutabaga | drosophila calmodulin activated adenylyl cyclase |
| ratACtp5 | rat adenylyl cyclase type 5 |
| ACtp5sp1 | dog adenylyl cyclase type 5 splice variant |
| ratACtp6 | rat adenylyl cyclase type 6 |
| musAC | mouse adenylyl cyclase type 9 (AC) |
| ratACtp2 | rat adenylyl cyclase type 2 |
| ratACtp4 | rat adenylyl cyclase type 4 |
| musACtp7 | mouse adenylyl cyclase type 7 |
| humACtp7 | human adenylyl cyclase type 7 |

FIG. 16

Illustrates cyclases extracted from their alignments with FKBPs.

Abbreviations and Sequence Identifiers 1. bovine adenylyl cyclase type 1 (SEQ ID NO: 87)
2. rat adenylyl cyclase type 3 (SEQ ID NO: 88)
3. rat adenylyl cyclase type 8 (SEQ ID NO: 89)
4. drosophila calmodulin activated adenylyl cyclase (SEQ ID NO: 90)
5. rat adenylyl cyclase type 5 (SEQ ID NO: 91)
6. dog adenylyl cyclase type 5 splice variant (SEQ ID NO: 92)
7. rat adenylyl cyclase type 6 (SEQ ID NO: 93)
8. mouse adenylyl cyclase type 9 ie AC (SEQ ID NO: 94)
9. rat adenylyl cyclase type 2 (SEQ ID NO: 95)
10. rat adenylyl cyclase type 4 (SEQ ID NO: 96)
11. mouse adenylyl cyclase type 7 (SEQ ID NO: 97)

FIG. 17

Illustrates the relative hybridisation intensity in different tissues, showing the distribution of AC mRNA in mouse, as measured by RNase protection assay.

FIG. 18

Construction of Complete Human AC9 cDNA

Scheme showing relationship of overlapping human AC9 cDNA clones used in construction of the complete hAC9 cDNA (GenBank/EMBL Accession Number AJ133123) by joining clones HiBBC33, pJP192, pJP230 and 166657 at the Mlu I, Eco RV and Nco I sites indicated as described in materials and methods. The relationship of these clones to human AC9 cDNA clones isolated by other groups (GenBank/EMBL Accession Numbers AF036927 and AB011092) identified in subsequent searches of the GenBank/EMBL DNA sequence database is also represented.

FIG. 19

Immunocytochemical Detection of Human AC9 Protein

Cells cultured on coverslips were briefly fixed with 3% paraformaldehyde and reacted with affinity purified chicken antibodies directed against residues 1340–1353 of the mouse AC9 protein, with a tyrosine added at the N-terminus. Subsequently, rabbit anti-chicken IgG coupled to FITC was applied, and the cells were viewed under a Leica TCS-NT confocal microscope system. Note (a) preferential localisation of immunoreactivity in the vicinity of the plasma membrane and (b) dividing cell with membrane localisation of AC9. (c) Specificity control with antibody preincubated with 10 μM of peptide antigen. The bar represents 10 μm.

FIG. 20

Detection of Multiple Human AC9 Polypeptides by Immunoblotting

Protein extracts from membranes of HEK 293 cells, either untransfected (a & b, lane 3) or stably transfected with human AC9 cDNA (a & b, lanes 1,2,4&5) separated by SDS-PAGE and electroblotted onto PVDF membrane were incubated with antisera directed against mouse AC9 N-terminus (a) or C-terminus (b). Positions of molecular weight markers (KDa) are indicated. A major polypeptide of 175 KDa was detected in two independent stable human AC9 transfectants (a & b, lanes 1 & 2). In addition, a faster migrating polypeptide was also detected. Specificity was confirmed by competition with peptide antigen (a & b, lanes 4 & 5). Increased background staining was apparent when C-terminal peptide was included (b, lanes 4 & 5).

FIG. 21

Analysis of cAMP Synthesis by HEK293 Cells Overexpressing Human AC9 a) Time-course of cAMP accumulation. Blockers of cyclic nucleotide degrading phosphodiesterases (PDE) (isobutylmethylxanthine 1 mM, and rolipram 0.1 mM) and various amounts of $Ca^{2+}$/EGTA were applied at time 0 to cells previously depleted of $Ca^{2+}$ in HBSS/EGTA medium containing no added $Ca^{2+}$, 1 μM thapsigargin and 10 μM ryanodine. The final extracellular levels of $Ca^{2+}$ were (Δ) nominally 0, (○) 2 mM, (n) 5 mM. Data are means±S.E.M. n=4 representative of 2 similar experiments. *P<0.05 when compared with the zero $Ca^{2+}$ group, 1-way ANOVA followed by Dunnett's test. b) Effect of FK506 on the inhibitory effect of $Ca^{2+}$ in cells pretreated with $Ca^{2+}$ free medium containing 5 μM 4-Br-A23187. Blockers of PDE were added in $Ca^{2+}$/EGTA to achive 0.25 and 0.5 mM extracellular $Ca^{2+}$. Data are expressed as multiples of the cAMP content measured in the absence of PDE blockers, means±S.E.M. n=4 representative of 3 similar experiments. * P<0.05 when compared with respective vehicle treated controls, +P<0.05 when compared with respective 0 $Ca^{2+}$ group. c) Pharmacological analysis of the effect of various immunosuppressant compounds on $Ca^{2+}$ inhibition of cAMP production. FK506, cyclosporin A (CsA), and rapamycin were used at 10 μM, L865,818 was present at 50 μM 20 min before the application of PDE blockers and $Ca^{2+}$/EGTA. Data are expressed as multiples of the cAMP content measured in the absence of PDE blockers, means±S.E.M. n=4 representative of 2 similar experiments. * P<0.05 when compared with respective vehicle treated controls.

FIG. 22

Differential Expression of Human AC9 mRNA a) A probe derived from 5' end of human AC9 cDNA (see materials and methods) detected an 8.5 kb transcript in all tissues represented on a northern blot of mRNAs from human heart (H), brain (B), placenta (Pl), lung (Lg), liver (Lv), skeletal muscle (M), kidney (K) and pancreas (Pn) as well as a 6.3 kb mRNA in heart and skeletal muscle. The control probe (b) confirmed expression of a 2 kb β-actin mRNA in all tissues as well as a 1.8 kb mRNA in heart and skeletal muscle. c) The same northern blot re-probed with a cDNA fragment derived from the extended 3' UTR of human AC9 clone KIAA0520 (see materials and methods) shows exclusive detection of an 8.5 kb MRNA. Positions of molecular weight markers (kb) are indicated.

FIG. 23

Localisation of Human AC9 mRNA in Human Forebrain a) Autoradiogram showing protection of 314 bases of the single-stranded human AC9 riboprobe derived from clone pJP195 in samples of total RNA from post-mortem human cortex, hippocampus and striatum as well as in the HEK 293 cell positive control (as indicated by the arrow). No protection of probe by yeast RNA (Y) was observed. Probe present prior to single-strand specific nuclease digestion is shown in the first lane (pr). b) In situ hybridisation using $^{35}S$ UTP-labelled anti-sense (i) and sense (ii) riboprobes derived from clone pJP195 incubated with 15 μm sections from normal adult post-mortem human brain showing detection of human AC9 mRNA by the anti-sense probe in hippocampal neurones of the CA1–CA3 regions (upper arrow) and dentate gyrus (lower arrow).

EXAMPLE 1

Calcineurin Feedback Inhibition of Agonist Evoked cAMP Formation

Introduction

The major immunosuppressant compounds cyclosporin A and FK506 are potent blockers of the $Ca^{2+}$/calmodulin-regulated protein phosphatase calcineurin (protein phosphatase 2B) in leukocytes (Liu et al, (1991) Cell 66:807–815). This observation has led to the discovery that calcineurin is an essential element of the signal transduction pathway activated by the T-cell receptor (Schreiber (1992) Cell 70:365–368 and Sigal et al, (1992) Ann. Rev. Immunol. 10:519–560). Immunophilins, which are proteins that mediate the effects of immunosuppressants on calcineurin activity in lymphocytes (Schreiber (1992) Cell 70:365–368) have been identified in the brain (Steiner et al, (1992) Nature 358:584–586) providing the plausible molecular targets of the prominent neurological side-effects of FK506 and cyclosporin A (Frank et al, (1993) Transplantation Proceeding 25:1887–1888 and Reyes et al, (1990) Transplantation 50:10434–1081).

While calcineurin is highly abundant in the brain (0.5–1% of total protein) (Klee et al, (1988) Advances in Enzymology 61:149–200) its functions in excitable cells remain to be defined. Calcineurin has been implicated in the control of voltage regulated ion channel activity (Armstrong, (1989) Trends in Neurosciences 12:117–122), particularly with respect to L-type calcium channels (Lai et al, (1993) J. Neurochem. 61:1333–1339). More recent studies have shown that the synaptic vesicular protein dynamin, which is thought to participate in synaptic vesicle recycling in nerve endings, is a prominent substrate for calcineurin (Liu et al, (1994) Science 265:970–973). Furthermore, blockage of calcineurin by immunosuppressants enhanced glutamate release by synaptosomes prepared from rat brain and this appeared to correlate with the state of phosphorylation of dynamin (Nichols et al, (1994) J. Biol. Chem. 269:23817–23823).

With respect to secretory function in other systems, it has been reported (Antoni et al, (1993) Biochem. Biophys. Res. Commun. 194:226–233) that immunosuppressants block calcineurin activity in pituitary corticotrope tumour (AtT20) cells and stimulate $Ca^{2+}$-dependent hormone release in correlation with their calcineurin blocking activity. Cyclic AMP (cAMP) is a cardinal signalling molecule in pituitary corticotrophs that causes an increase of intracellular free $Ca^{2+}$ ($[Ca^{2+}]_i$) and triggers the release of adrenocorticotrophic hormone (ACTH) (Antoni, (1986) Endocr. Rev. 7:351–378). Because $[Ca^{2+}]_i$ is known to inhibit cAMP formation in a variety of systems (Cooper et al, (1993) Trends Pharm. Sci. 14:34–36) we have analyzed in AtT20 cells the effects of FK506 and cyclosporin A on cAMP production induced by the hypothalamic neuropeptide corticotropin-releasing factor (CRF) and beta-adrenergic stimulation.

Experimental Procedures

AtT20 D16:16 mouse anterior pituitary tumour cells were maintained in culture as previously described (Woods et al, (1992) Endocrinology 131:2873–2880). For measurements of ACTH release, cAMP production or calcineurin activity the cells were plated on 24-well tissue culture plates ($5 \times 10^4$ cells/well), used 4–6 days afterwards. ACTH (Woods et al, (1992) Endocrinology 131:2873–2880) and cAMP (Dufau et al, (1973) Endocrinology 92:6–11) were measured by specific radioimmunoassays. Calcineurin protein phosphatase activity was determined by the $^{32}$P-labelled casein assay (Tallant et al, (1984) Arch. Biochem. Biophys. 232:269–279) or by using the $^{32}$P-labelled RII peptide substrate (Blumenthal et al, (1986) J. Biol. Chem. 261:8140–8145) adapted to measure calcineurin phosphatase activity in AtT20 cell extracts as previously described (Antoni et al, (1993) Biochem. Biophys. Res. Commun. 194:226–233).

Experiments for cAMP were all carried out in Hanks balanced salt solution containing 2 mM $CaCl_2$ and 1 mM $MgSO_4$ buffered with 25 mM HEPES pH 7.4 and supplemented with 0.25% (w/v) of bovine serum albumin. The cells were preincubated in serum free medium for 1 hour, after which blockers of phosphodiesterase (isobutylmethylxanthine 0.5 mM (IBMX) and/or rolipram 0.1 mM) along with various other treatments were applied for 30 minutes at 37° C. Subsequently the cells were cooled to 220° C. for 5 minutes in a water bath and agonists were added for 10 minutes. The reaction was stopped by the addition of 0.2 mol/l HCl to achieve a final concentration of 0.1 mol/l (Brooker et al, (1979) Adv. in Cyclic Nucl. Res. Vol. 10, G. Brooker, P. Greengard and G. A. Robinson, Raven Press, New York, 2–34). In the absence of phosphodiesterase blockers agonist-induced changes of total cAMP content (cells+medium) were small (2–3 fold of basal) and no increment of intracellular cAMP could be detected (Woods et al, (1992) Endocrinology 131:2873–2880). In the presence of IBMX total cAMP content increased linearly with time up to 10 minutes after the addition of CRF and remained constant for up to 20 minutes. In contrast, cellular cAMP content peaked between 2–5 minutes and subsequently declined to basal levels even in the presence of the phosphodiesterase blockers. Hence, after establishing that immunosuppressant drugs had the same effect on peak cellular and total cAMP content under these conditions, all experiments shown here report total cAMP content.

In some experiments cells were preincubated for 30 minutes in medium containing 2 mmol/l EGTA and no added $Ca^{2+}$, supplemented with 5 $\mu$mol/l A23187 and 2.5 $\mu$mol/l nifedipine in order to deplete rapidly mobilized cellular stores of $Ca^{2+}$. This treatment also ensured that L-type $Ca^{2+}$ channels, the principal avenue of voltage-regulated $Ca^{2+}$ influx in AtT20 cells (Luini et al, (1985) Proc. Natl. Acad. Sci. U.S.A. 82:8034–8038; Reisine et al, (1987) Mol. Pharmacol. 32:488–496 and Antoni et al, (1992) J. Endocrinol. 133:R13-R16) were fully blocked and $Ca^{2+}$ subsequently added to the extracellular fluid would enter largely through the pores made by the ionophore A23187. The rationale for this pretreatment is that calcineurin reportedly influences L-channel activity (Lai et al, (1993) J. Neurochem. 61:1333–1339; and Armstrong et al, (1987) Proc. Natl. Acad. Sci. U.S.A. 84:2518–2522), whereas the treatment regimen used here would make $Ca^{2+}$ entry independent of this regulation.

Immunosuppressant analogues (FK506, courtesy of Fujisawa Ltd, Osaka, Japan; cyclosporin A and SDZ 220–384 (MeVal$^4$-cyclosporin A) (Fliri, H. (1993) Antibiotics and antiviral compounds, Chemical synthesis and modification K. Krohn, H. Kirst And H. Maasg, VCN Verlagsgesellschaft mbH, Weinheim, 229–240), courtesy of Sandoz Pharma, Basel, Switzerland, L685,818 (Dumont et al, (1992) J. Exp. Med. 176:751–760) courtesy of Merck&Co, Rahway, N.J.) were also applied during the preincubation period. These compounds were made up in ethanol at $10^{-3}$ mol/l and diluted with the incubation medium to the desired final concentrations. In some cases cells were preincubated with L685,818 the structural analogue of FK506 that binds to FKBP-12 and inhibits prolyl-isomerase activity but is devoid of immunosuppressant activity (Dumont et al, (1992) J. Exp. Med. 176:751–760) for 10 minutes before the addition of FK506 for 30 minutes at 37° C.

Incubations for ACTH secretion were carried out as previously described (Woods et al, (1992) Endocrinology 131:2873–2880) except that the test incubation with CRF was at 22° C.

Amplification and DNA Sequence Analysis of Adenylyl Cyclases cDNAs in AtT20 Cells Total RNA was prepared from approximately $10^7$ cells using Trizol reagent (GIBCO, Paisley, UK) according to the manufacturer's instructions. RT-PCR was carried out using an RNA PCR kit (Perkin Elmer, Warrington, Cheshire, U.K.). Briefly, 0.8 $\mu$g of total RNA was denatured at 95° C. for 5 minutes then annealed with 2.5 $\mu$M random hexanucleotide primers for first-strand cDNA synthesis which was carried out for 15 minutes at 42° C. in a 20 $\mu$l reaction mixture containing 10 mM Tris.HCl, pH8.3, 50 mM KCl, 5 mM $MgCl_2$, 1 mM each dNTP, 20U RNase inhibitor and 50U MMLV reverse transcriptase. The reaction was terminated at 99° C. for 5 minutes then cooled to 4° C. and stored on ice. PCR was performed using degenerate oligonucleotides, either pair A or pair B corresponding to highly conserved regions within the first (pair A: 5'CTCATCGATGGIGAYTGYTAYTAYTG3' (SEQ ID NO: 5); 3'GGCTCGAGCCAIACRTCRTAYTGCCA5' (SEQ ID NO: 6) expected product size 220 bp) and second (pair B: 5'GAAGCTTAARATIAARACIATIGGI$^T/_A$$^C/_G$ IACI-TAYATGGC3' (SEQ ID NO: 7); 3'GGGATCCACRTTI-ACIGTRTTICCCCAIATRTCRTA5' (SEQ ID NO: 8) expected product size 180 bp) cytoplasmic domains of previously cloned mammalian adenylyl cyclases (Yoshimura et al, (1992) Proc. Natl. Acad. Sci. U.S.A. 89:6716–6720; Krupinski et al, (1992) J. Biol. Chem. 267:24859–24862; and Gao et al, (1991) Proc. Natl. Acad. Sci. U.S.A. 88:10178–10182). For PCR the reverse transcription reaction (20 $\mu$l) was expanded to 100 $\mu$l and contained 10 $\mu$M Tris.HCl, pH 8.3, 50 mM KCl, 2 mM $MgCl_2$, 200 $\mu$M each dNTP, 35 pmol of each primer and 2.5U Amplitaq DNA polymerase. PCR reactions were overlaid with mineral oil (Sigma, Poole, Dorset, U.K.) and denatured at 95° C. for 3 minutes followed by 5 cycles (60 seconds denaturation at 94° C., 60 seconds annealing/extension at 45° C.) then a further 35 cycles (60 seconds denaturation at 94° C., 60 seconds annealing/extension at 55° C.) and finally 7 minutes annealing/extension at 55° C. An aliquot (5%) of each reaction was analysed by agarose gel electrophoresis (3% FMC, Flowgen Instruments Ltd, Sittingbourne, Kent, U.K.). Products within the expected size range for each primer pair were excised from the gel, purified using a Wizard™ PCR Prep kit (Promega, Madison, Wis., U.S.A.) and ligated into the vector pGEM-T (Promega). Clones containing an insert of the expected size were identified and their DNA sequence determined by the dideoxynucleotide method (Sequenase 2.0 kit, USB, Amersham International, Aylesbury, U.K.).

Detection of mRNA Expression

Northern analysis was performed using standard procedures. Briefly, 10 µg of total RNA was separated by formaldehyde gel electrophoresis and transferred by blotting onto positively charged nylon membrane (Appligene,) then fixed by baking at 80° C. and prehybridised at 42° C. for 2 hours in 50% deionised formamide, 5×SSPE, 0.5×Denhardt's, 0.1% w/v SDS, 0.2 mg/ml denatured salmon sperm carrier DNA and 10% Dextran sulphate. Random-primed labelled DNA probe (50 ng; >$10^9$ cpm/µg) was then added and hybridisation continued overnight at 42° C. The membrane was washed twice for 20 minutes in 2×SSC/0.1% SDS, followed by 20 minutes in 1×SSC/0.1% SDS at 42° C. and finally 20 minutes in 0.5×SSC/0.1% SDS at 50° C. before wrapping in cling-film an exposing to autoradiographic film at −70° C. Ribonuclease protection assays were performed using an RPA II kit (Ambion, AMS Biotechnology, Witney, Oxon, U.K.) according to the manufacturer's instructions. Briefly, 10 µg of total RNA was hybridised overnight at 45° C. to $10^5$ cpm of radiolabelled anti-sense riboprobe. Following hybridisation reactions were digested with single-strand-specific RNase and protected fragments resolved on a 6% denaturing polyacrylamide gel which was fixed for 30 minutes in 15% methanol/5% acetic acid, dried and exposed to autoradiographic film at −70° C.

Results

Enhancement of CRF-Stimulated cAMP Production by Immunosuppressants

Immunosuppressant blockers of calcineurin activity, FK506, cyclosporin A and MeVal$^4$-cyclosporin A enhanced CRF-induced cAMP production in a concentration dependent manner (FIG. 1). The effect of cyclosporin A (FIG. 2) was statistically significant (P<0.05 or less) at 2, 5 and 10 minutes after the addition of CRF, similar data were also obtained with FK506. Enhancement of cAMP formation by FK506 was apparent at lower concentrations (0.1–10 nmol/l) of CRF, while the maximal response appeared unchanged (FIG. 2B).

Figure 3:
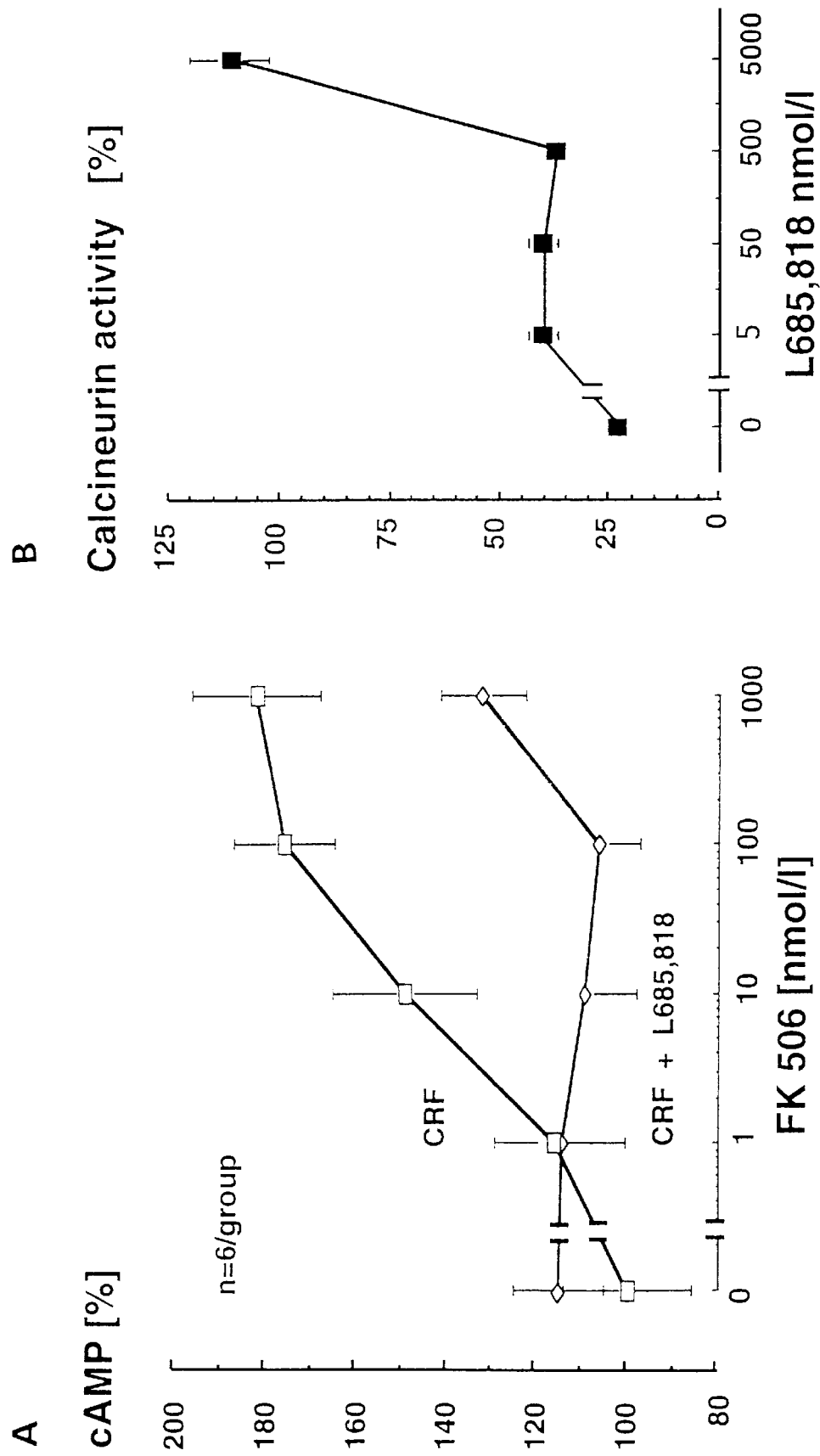

The effect of FK506 on CRF-induced cAMP production (FIG. 3) could be antagonized by the FK506 analog L685, 818, a potent inhibitor FKBP-12 prolyl isomerase activity which has no immunosuppressant activity and does not block calcineurin (Dumont et al, (1992) J. Exp. Med. 176:751–760) and hence, is a specific antagonist of the calcineurin inhibitory action of FK506. Importantly, this compound also blocked the inhibitory effect of FK506 on calcineurin-mediated dephosphorylation of phosphocasein (FIG. 3) in AtT20 cells.

Figure 4:
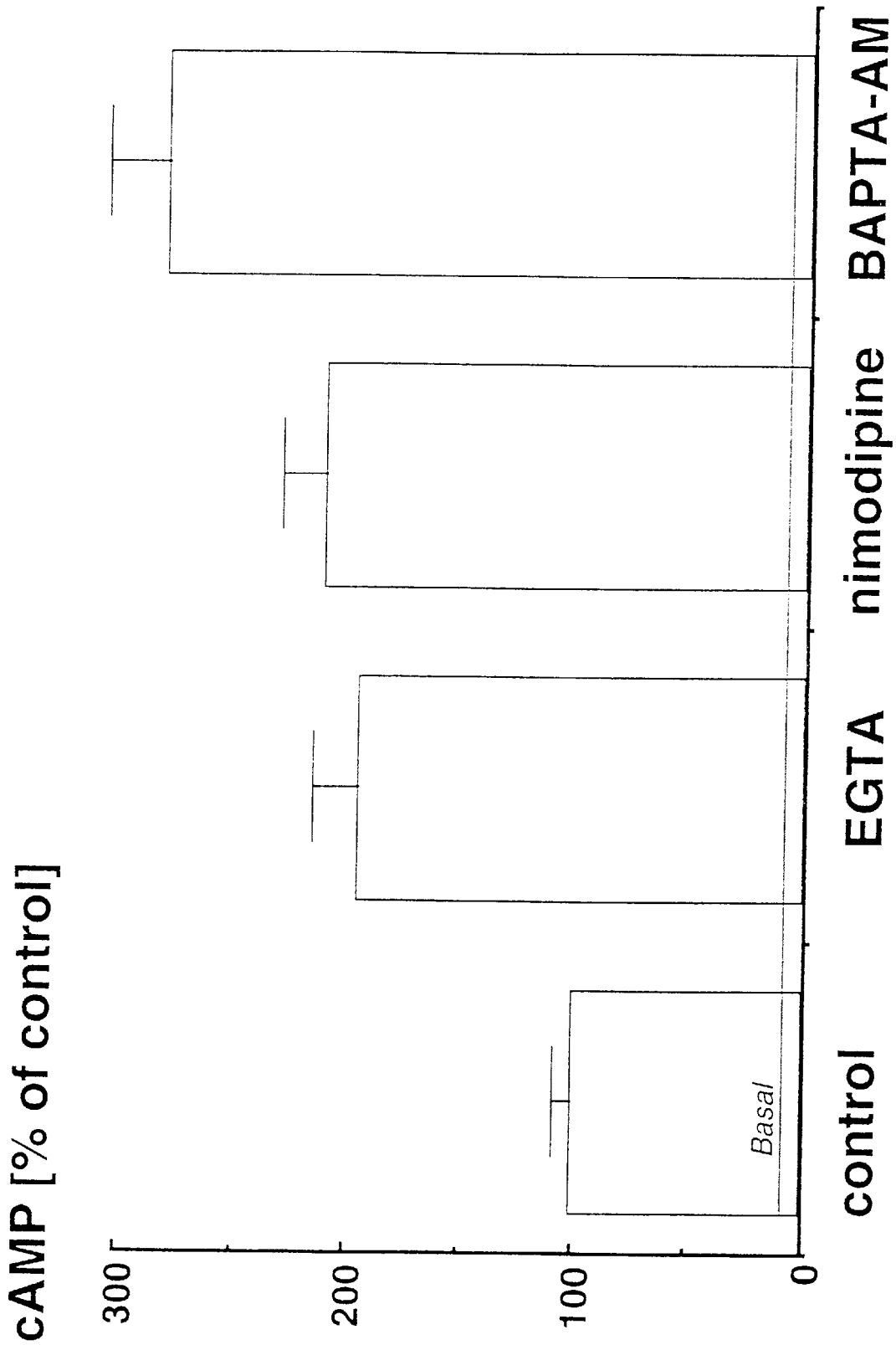

Receptor-Evoked Synthesis of cAMP is Under Inhibitory Control by Intracellular Ca$^{2+}$ and Calcineurin Lowering of intracellular free Ca$^{2+}$ by a variety of methods, such as depletion by EGTA and the calcium ionophore A23187, loading of the cells with the intracellular calcium chelator BAPTA-AM and blockage of calcium channels with the dihydropyridine channel blocker nimodipine, all markedly increased the cAMP response to CRF (FIG. 4). The effect of BAPTA-AM on CRF-induced cAMP formation was statistically significant (P<0.05) by 2 minutes after the addition of CRF and at all subsequent time-points studied up to 20 minutes (not shown).

Figure 5:
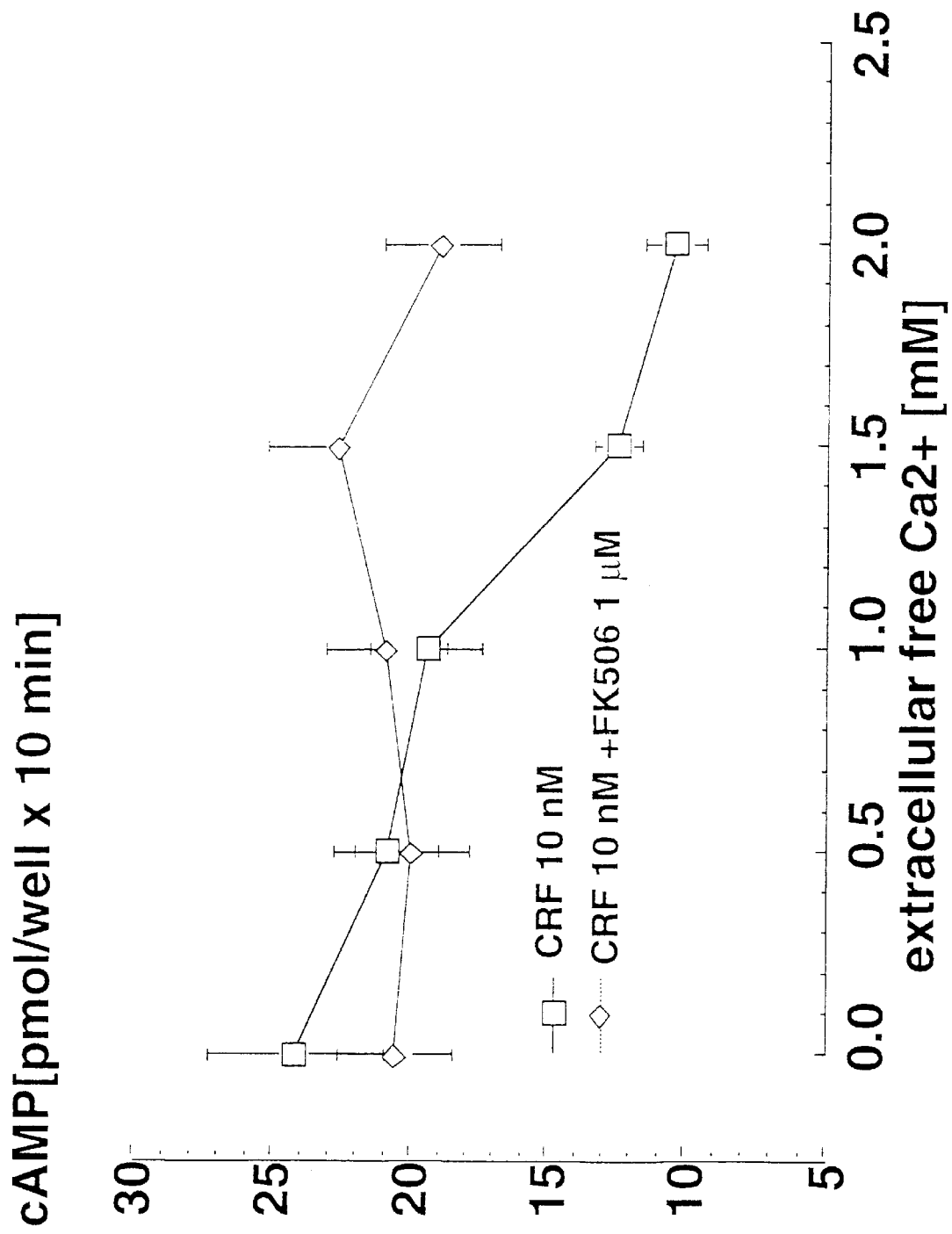

Addition of graded amounts of Ca$^{2+}$ with CRF to cells depleted of Ca$^{2+}$ and pretreated with the ionophore A23187 produced a concentration-dependent inhibition of CRF-induced cAMP production to levels seen in non-depleted cells incubated in medium containing 2 mmol/l Ca$^{2+}$. The effect of exogenous Ca$^{2+}$ could be inhibited by FK506, which, in fact failed to alter cAMP accumulation in the absence of Ca$^{2+}$ (FIG. 5).

Site and Specificity of Immunosuppressant Action

Figure 6:
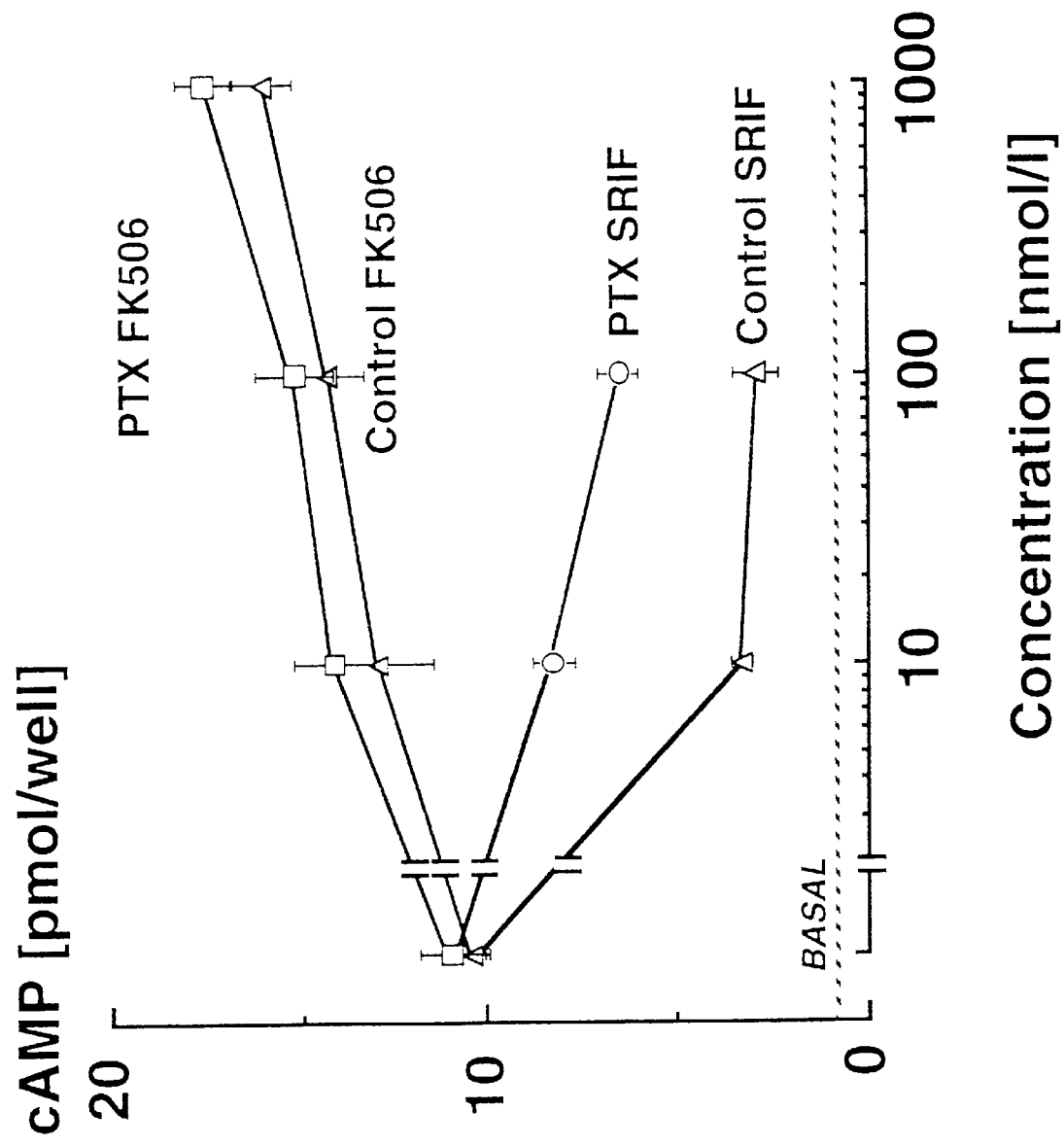

The effect of FK506 on CRF-induced cAMP formation was also evident after a 16 hours pretreatment of the cells with pertussis toxin (1 µg/ml) (FIG. 6) which strongly suppressed inhibitory G-protein function as assessed by the attenuation of somatostatin-mediated inhibition of cAMP formation. Pertussis toxin treatment also had no effect on the suppression of CRF-induced cAMP formation by extracelluar Ca$^{2+}$ in Ca$^{2+}$-depleted cells (not shown).

FK506 had no significant effect on cAMP accumulation evoked by 10 or 30 µM forskolin, a drug that activates adenylyl cyclase independently of Gs. Loading of the cells with BAPTA-AM caused a small (15%), but statistically significant (P<0.05) enhancement of forskolin-evoked cAMP accumulation (not shown).

Finally, in contrast to the effects of FK506 and cyclosporin A, pretreatment with other blockers of protein phosphatases such as calyculi A (1–30 nmol/l) okadaic acid (0.2–5 µmol/l), caused a concentration-dependent inhibition (up to 80%) of CRF-induced cAMP accumulation (not shown and Koch et al, (1994) Cellular Signalling 6:467–473).

Enhancement of CRF Stimulated ACTH Release by FK506

Figure 7:
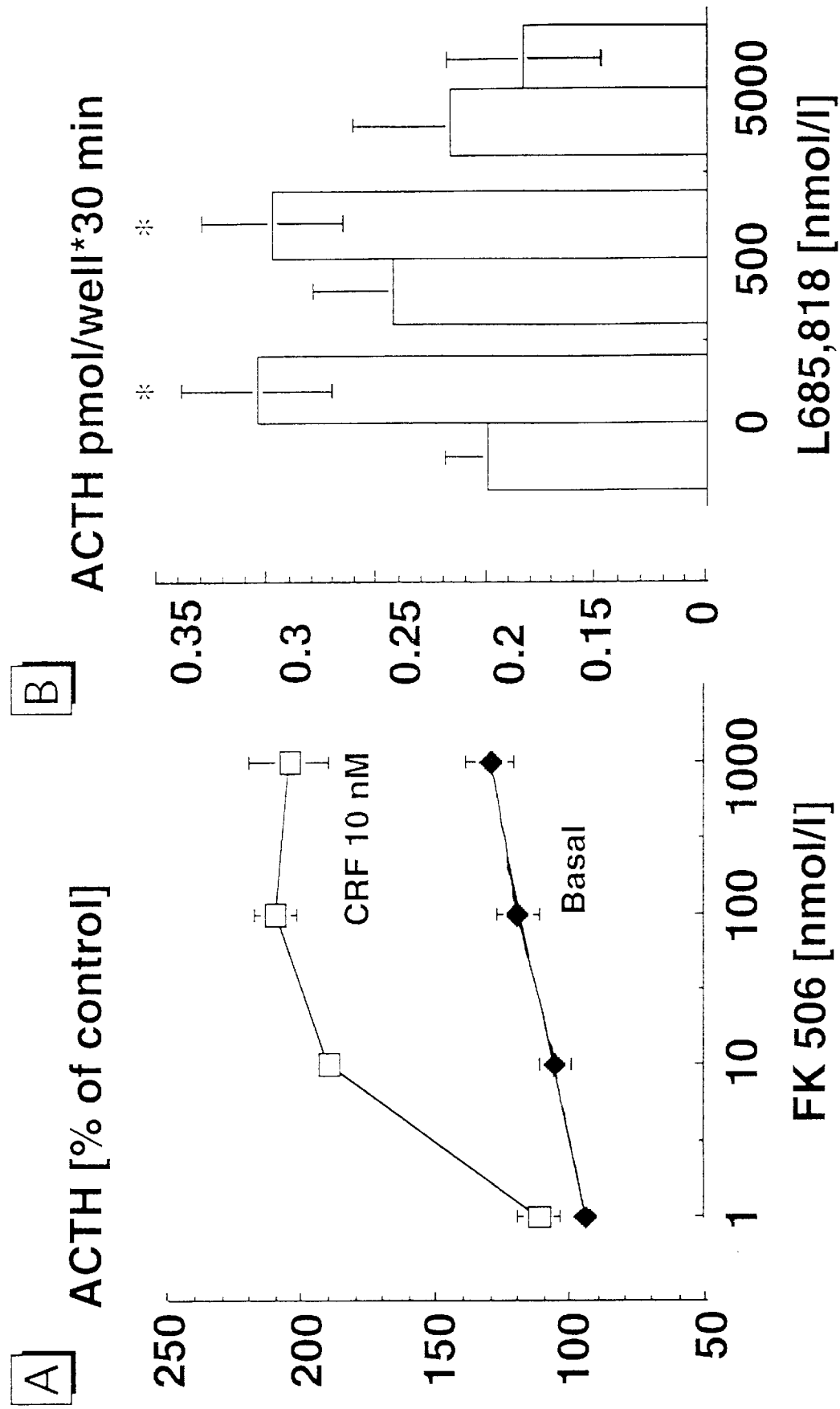

Blockage of calcineurin activity by FK506 enhanced the release of ACTH evoked by CRF (FIG. 7A), and this action was prevented by L685,818 (FIG. 7B). Note, that the apparent EC$_{50}$s of FK506 to inhibit calcineurin activity in AtT20 cells (Antoni, (1986) Endocr. Rev. 7:351–378), to stimulate ACTH release and to augment cAMP accumulation induced by CRF are all approximately 10 nM.

β-adrenergic Stimulation is Under Similar Regulation by Calcineurin

Isoproterenol induces cAMP accumulation through β$_2$ adrenergic receptors in AtT20 cells (Heisler et al, (1983) Biochemical And Biophysical Research Communications 111:112–119). Isoproterenol induced cAMP formation was also enhanced by BAPTA-AM, FK506 and Ca$^{2+}$-depletion in AtT20 cells (Table 1).

Effect of Immunosuppressants on cAMP Accumulation in AtT20 Cells Correlates With the Expression of a Novel Adenylyl Cyclase mRNA In order to determine the profile of adenylyl cyclase isoforms present in AtT20 cells two sets of degenerate oligonucleotide primers were used to analyze AtT20 cell total RNA for adenylyl cyclase related sequences by means of RT-PCR. Using primer set B a PCR product of approximately 180 bp was obtained. DNA sequence analysis revealed that approximately 8% of the subcloned 180 bp cDNA fragments amplified proved to be identical to Type 6 adenylyl cyclase. The majority (>90%), however, gave a novel sequence exhibiting a high level of homology with the amino acid sequences of known mammalian adenylyl cyclases present within current databases but which was not identical to any previously reported sequence (FIG. 8). Type 1 adenylyl cyclase was detected in AtT20 cells using primer set A.

Northern blot analysis of total RNA using the novel adenylyl cyclase 180 bp cDNA fragment as a probe indicated hybridisation to an approximately 9 kb mRNA expressed in AtT20 cells. Expression of this message was not detected in NCB20 or HEK293 cell RNA.

As a more sensitive alternative mRNA expression was also assayed by ribonuclease protection of the message using a radiolabelled anti-sense riboprobe transcribed from the novel adenylyl cyclase 180 bp cDNA. The presence of a ribonuclease-protected fragment migrating as a distinct, approximately 155 bp band on a denaturing polyacrylamide gel indicates that the novel adenylyl cyclase mRNA is highly abundant in AtT20 cells whereas only very low levels are present in NCB20 cells and in HEK293 cells the message remains undetected.

Measurements of calcineurin activity in cell extracts from all three cell lines revealed a similar sensitivity of calcineurin protein phosphatase activity (substrate RII subunit peptide Fruman et al, (1992) Proc. Natl. Acad. Sci. U.S.A. 89:3686–3690) towards inhibition by FK506 and cyclosporin A. Furthermore, all three cell lines responded to stimulation by CRF which was enhanced by depletion of intracellular free calcium. FK506 and cyclosporin A enhanced CRF-induced cAMP formation consistently in AtT20 cells; in NCB20 cells only one out of 4 experiments gave a statistically significant effect of cyclosporin A on CRF-induced cAMP accumulation and no effects were observed in HEK293 cells.

Discussion

These data show that receptor-stimulated cAMP formation may be regulated by calcineurin, and that this regulation is associated with the expression of a novel adenylyl cyclase mRNA.

All studies of cAMP formation reported here were carried out in the presence of blocker(s) of phosphodiesterase (IBMX and/or rolipram), and hence the effects observed relate to the synthesis of cAMP rather than its degradation.

Evidence for the involvement of calcineurin in the control of cAMP accumulation is provided by the use of immunosuppressant analogs previously (Antoni et al, (1993) Biochem. Biophys. Res. Commun. 194:226–233; and Fliri (1993) Antibiotics and antiviral compounds, Chemical synthesis and modification K. Krohn, H. Kirst And H. Maasg, VCN Verlagsgesellschaft mbH, Weinheim, 229–240) shown to block calcineurin activity in AtT20 cells and T lymphocytes cells with the same order of potency that they influenced cAMP accumulation (present study). Furthermore, L685,818 an analogue of FK506 (Dumont et al, (1992) J. Exp. Med. 176:751–760) that binds to the prolyl-isomerase FKBP-12 in a manner similar to FK506, but does not give rise to a drug protein complex that inhibits the activity of calcineurin, reversed the effects of FK506 on calcineurin activity, cAMP formation as well as ACTH release. Importantly, when given alone L685,818 had no discernible effect on cAMP formation or ACTH secretion further suggesting that the changes observed upon treatment with FK506 are due to the inhibition of calcineurin. Finally, neither FK506 nor cyclosporin A were effective in cells depleted of $Ca^{2+}$.

Taken together, these characteristics justify the conclusion that the effects of immunosuppressants described here are attributable to the inhibition of calcineurin.

The production of cAMP in AtT20 cells is under inhibitory control by $[Ca^{2+}]_i$. Stimulation with cAMP is known to elicit a rise of $[Ca^{2+}]_i$ in these cells which is largely derived from the extracellular pool by influx through dihydropyridine sensitive $Ca^{2+}$-channels (Luini et al, (1985) Proc. Natl. Acad. Sci. U.S.A. 82:8034–8038; Reisine et al, (1987) Mol. Pharmacol. 32:488–496 and Antoni et al, (1992) J. Endocrinol. 133:R13–R16), as intracellular pools of $Ca^{2+}$ are sparse (Fiekers (1993) Abstracts of the 23rd Annual Meeting of the Society for Neuroscience 1186 Abst 488.3). Thus the $[Ca^{2+}]_i$ signal is a measure of electrical activity of the cell and in addition to triggering hormone release provides feedback inhibition to the chemical messenger system that generates it. In the case of CRF-induced cAMP formation this feedback is largely mediated by calcineurin.

Several possibilities have to be considered with respect to the site of action of $Ca^{2+}$/calcineurin in the signal transduction cascade.

An action of calcineurin at the receptor level is conceivable, however, the prevailing concept of G-protein coupled receptors (Sibley et al, (1987) Cell 48:913–922) dictates that receptor-down regulation or uncoupling is largely due to the action of protein kinases while protein phosphatases reverse this process. In contrast, the present data implicate calcineurin as an inhibitor of receptor stimulated cAMP production.

Dephosphorylation of the coupling protein Gs is also a possible site of regulation by calcineurin (Houslay (1994) GTPases in Biology B. F. Dickey and L. Birnbaumer, Springer Verlag, Berlin, Vol 108 Pt2, 147–165). Once more, current evidence in the literature associates protein phosphorylation with down-regulation of G-protein function and implicates protein phosphatases in the restoration of the cellular response (Pyne et al, (1992) Biochem. Biophys. Res. Commun. 186:1081–1086; and Strassheim et al, (1994) J. Biol. Chem. 269:14307–14313).

With respect to the effector adenylyl cyclase, these proteins have lately emerged as dynamic sites of signal integration (Taussig et al, (1995) J. Biol. Chem. 270:1–4). At least two types of cyclase, Types 5 & 6 (Iyengar (1993) Advances in Second Messenger and Phosphoprotein Research B. L. Brown and P. R. M. Dobson, Raven Press Ltd, New York, 28:27–36), are inhibited by $Ca^{2+}$ but the mechanism of this effect has not been elucidated (Yoshimura et al, (1992) Proc. Natl. Acad. Sci. U.S.A. 89:6716–6720). The inhibition of Type 5 and 6 cyclase by $Ca^{2+}$ is most marked after stimulation by agonists such as isoproterenol in chick heart cells (Yu et al, (1993) Mol. Pharmacol. 44:689–693), or VIP in $GH_4C_1$ pituitary tumour cells (Boyajian et al, (1990) Cell Calcium 11:299–307), but much less prominent after activation with forskolin in $GH_4C_1$ cells (Boyajian et al, (1990) Cell Calcium 11:299–307). Overall this is analogous to the observations made here, which in the first instance suggest a prominent action of calcineurin at or before the level of G-protein effector coupling. However, multiple types of adenylyl cyclase coexist in all cell types analyzed to date (Yoshimura et al, (1992) Proc. Natl. Acad. Sci. U.S.A. 89:6716–6720; DeBernardini et al, (1993) Biochem. J. 293:325–328 and Hellevuo et al, (1993) Biochem. Biophys. Res. Commun. 192:311–318) and this applies to AtT20 cells as RT-PCR analysis and sequencing of the amplified cDNAs clearly showed coexpression of at least three types of adenylyl cyclase mRNA (type 1 and 6 as well as a novel isotype). Forskolin appears to activate adenylyl cyclase isotypes by different efficacies and mechanisms (Iyengar (1993) Advances in Second Messenger and Phosphoprotein Research B. L. Brown and P. R. M. Dobson, Raven Press Ltd, New York, 28:27–36), hence the relative contribution of individual cyclase isotypes to forskolin-induced cAMP may be different from receptor activated cAMP formation, and as a result forskolin-induced cAMP synthesis and receptor activated synthesis may have different pharmcological profiles.

It is unlikely that type 1 cyclase is involved in the effects of $Ca^{2+}$ and calcineurin reported here as it is invariably stimulated by $Ca^{2+}$, whereas the predominant effect on CRF and β-adrenergic stimulation was an inhibition by $Ca^{2+}$. Type 6 adenylyl cyclase could be implicated because it is strongly inhibited by $Ca^{2+}$, however, although the Type 6 isozyme is abundant in NCB20 (Yoshimura et al, (1992) Proc. Natl. Acad. Sci. U.S.A. 89:6716–6720) as well as HEK293 cells (Hellevuo et al, (1993) Biochem. Biophys. Res. Commun. 192:311–318) the stimulation of cAMP accumulation in these cells through endogenously expressed receptors for CRF was not altered upon blockage of calcineurin protein phosphatase activity. Importantly, the novel adenylyl cyclase homologue mRNA was undetectable in HEK293 cells and was found in very low amounts in NCB20 cells, whereas it appears to be the predominant adenylyl cyclase isotype mRNA in AtT20 cells. Work reported elsewhere (Paterson et al, (1995) Biochem. Biophys. Res. Commun. 214:1000–1008) reports isolation of a 4473 bp cDNA from AtT20 cells which contains the complete coding sequence of this novel mouse adenylyl cyclase.

Taken together, these data suggest that the effects of calcineurin inhibitors are associated with specific adenylyl cyclase isotype previously not characterized.

The potential functional significance of calcineurin negative feedback on cAMP formation in pituitary cells is highlighted by previous findings, showing that adrenal corticosteroid inhibition of CRF-induced ACTH release involves the de novo synthesis of calmodulin, the calcium sensor regulatory protein of calcineurin (Shipston et al, (1992) Biochem. Biophys. Res. Commun. 189:1382–1388). Furthermore, the efficiency of corticosteroid inhibition is reduced by approximately 10-fold by immunosuppressant blockers of calcineurin (Shipston et al, (1994) Ann. N. Y. Acad. Sci. 746:453–456; and Antoni et al, (1994) J. Physiol-London 475:137–138).

In summary, calcineurin is a $Ca^{2+}$-operated feedback inhibitor of cAMP production activated by CRF or β-adrenergic receptors in pituitary corticrope tumour cells. As $[Ca^{2+}]_i$ is largely derived through voltage-regulated $Ca^{2+}$ channels in AtT20 cells, these cells exemplify a case where calcineurin functions as a link between the chemical and electrical signalling systems of the cell. These findings conform with previous reports (Armstrong (1989) Trends in Neurosciences 12:117–122; and Nichols et al, (1994) J. Biol. Chem. 269:23817–23823) suggesting that in excitable cells calcineurin is a fundamental negative feedback regulator of cellular responses as opposed to its role as a stimulatory element in non-excitable systems (Kincaid et al, (1993) Adv. Prot. Phosphatases 7:543–583). Furthermore, our findings extend the involvement of calcineurin from calcium channels and synaptic vesicle recycling to the adenylyl cyclase signalling pathway that is fundamental for intracellular signalling throughout the CNS.

Summary

The $Ca^{2+}$- and calmodulin-activated protein phosphatase calcineurin is highly abundant in the brain. While a physiological role for calcineurin has been delineated in T lymphocyte activation, little is known about its role in excitable cells. The present study investigated the effects of immunosuppressant blockers of calcineurin on agonist-induced cAMP formation and hormone release by mouse pituitary tumour (AtT20) cells. Inhibition of calcineurin with FK506 or cyclosporin A enhanced cAMP formation and adrenocorticotropin secretion induced by corticotropin releasing-factor (CRF). Further analysis of cAMP production revealed that intracellular $Ca^{2+}$ derived through voltage-regulated calcium channels reduces cAMP formation induced by corticotropin releasing-factor or $β_2$-adrenergic stimulation, and that this effect of $Ca^{2+}$ is mediated by calcineurin. Analysis of AtT20 cell RNA indicated the co-expression of at least three species of adenylyl cyclase mRNA encoding types 1 and 6 as well as a novel isotype, which appeared to be the predominant species. In two cell lines expressing very low or undetectable levels of the novel cyclase mRNA (NCB20 and HEK293 respectively), CRF-induced cAMP formation was not altered by FK506 or cyclosporin A. In summary, these data identify calcineurin as a $Ca^{2+}$ sensor that mediates a negative feedback effect of intracellular $Ca^{2+}$ on receptor-stimulated cAMP production thereby regulating the cellular response to cAMP generating agonists. Furthermore, the effect of calcineurin on cAMP synthesis appears to be associated with the expression of a novel adenylyl cyclase isoform, which is highly abundant in AtT20 cells.

EXAMPLE 2

DNA Cloning and Tissue Distribution of AC

Introduction

Adenylyl cyclases convert ATP to cAMP, one of the earliest recognized intracellular messenger molecules. The family of previously known adenylyl cyclases consists of eight members (Premont (1994) Meth. Enzymol. 238:116–127). Some of these enzymes have been analyzed functionally, and appear to confer unique signal processing capacities to cells (Taussig et al, (1995) J. Biol. Chem. 270:1–4). In particular isotype specific regulation of enzymatic activity by calmodulin, calcium (through as well as independently of calmodulin), protein kinase C as well as G-protein subunits has been demonstrated (for review see Taussig et al, (1995) J. Biol. Chem. 270:1–4). In addition to functional diversity adenylyl cyclase isotypes have distinct tissue distribution profiles (Krupinski et al, (1992) J. Biol. Chem. 267:24859–24862) and particularly marked regional differences of cyclase distribution have been observed in the brain (Xia et al, (1994) Mol. Brain Res. 22:236–244; and Glatt et al, (1993) Nature 361:536–538). Collectively, these observations indicate that the particular adenylyl cyclase isotype profile of a cell is fundamentally important with respect to cellular function.

Pharmacological analysis of the cAMP response to agonist stimulation in mouse corticotroph tumor (AtT20) cells (Antoni et al, (1994) Journal Of Physiology-London 475p:137–138) has shown that calcium inhibition of cAMP accumulation in these cells is mediated by the $Ca^{2+}$/calmodulin activated protein phosphatase calcineurin (protein phosphatase 2B). This novel feature of the cAMP response has led to the examination of the adenylyl cyclase isotype profile of AtT20 cells (Antoni et al, (1995) EMBO Journal submitted), which, amongst two known sequences (types 1 and 6), revealed the presence of a novel isotype. The present study reports the full cDNA sequence and tissue distribution of this novel adenylyl cyclase which is the predominant species of the enzyme expressed in AtT20 cells. The enzyme mRNA is also relatively abundant in the brain as well as certain peripheral endocrine organs, including the ovary and the adrenal gland.

Materials and Methods

Isolation of a cDNA Containing the Complete Coding Sequence of a Novel Mouse Adenylyl Cyclase Identified in AtT20 Cells AtT20 cells were grown to sub-confluency in DMEM supplemented with 10% foetal calf serum (Woods et al, (1992) Endocrinology 131:2873–2880) and total RNA was isolated from approximately $10^7$ cells using Trizol reagent (GIBCO, Paisley, U.K.) according to the manufacturer's instructions. RT-PCR was carried out using an RNA PCR kit (Perkin Elmer, Warrington, Cheshire, U.K.) as previously described (Antoni et al, (1995) EMBO Journal submitted), using degenerate oligonucleotides corresponding to a highly conserved region within the second cytoplasmic domain of previously cloned mammalian adenylyl cyclases (Krupinski et al, (1992) J. Biol. Chem. 267:24859–24862; Yoshimura et al, (1992) Proc. Natl. Acad. Sci. U.S.A. 89:6716–6720; and Gao et al, (1991) Proc. Natl. Acad. Sci. U.S.A. 88:10178–10182) A 180 bp cDNA fragment of a novel adenylyl cyclase amplified from AtT20 cells (Antoni et al, (1995) EMBO Journal submitted) was used as a probe to obtain a cDNA containing the complete coding sequence by screening an oligo dT-primed cDNA library prepared from AtT20 cells and constructed in the vector ZAP II (a generous gift of Dr. M J Shipston, Edinburgh (see Shipston (1992) PhD Thesis, University of Edinburgh)) together with 5' RACE PCR. Screening of approximately $5 \times 10^5$ clones was carried out according to standard procedures (Sambrook et al, (1989) Cold Spring Harbor Press, U.S.A.). Plaque-purified positive clones were recovered as pBluescript phagemids by excision using the helper phage ExAssist (Stratagene, Cambridge, U.K.). The insert size of these clones ranged from 1–3 kb. DNA sequence was determined from several independent isolates of each clone using Exo III/Mung Bean nuclease digestion and/or clone-specific primers with the Sequenase 2.0 kit (USB, Amersham International, Aylesbury, U.K.). Analysis of the DNA sequence data generated revealed the presence of an open frame which lacked a suitable initiator codon.

Two rounds of 5' RACE-PCR were performed to obtain the remaining of the open reading frame using a 5' RACE System kit (GIBCO, Paisley, U.K.) according to the manufacturer's instructions and summarised in brief as follows. Based on the DNA sequence at the 5' end of the largest cDNA clone isolated by library screening (jp134) a set of three nested anti-sense oligonucleotides were designed. The first of these (most proximal to the 3' end of the cDNA isolated; primer 1: CGTCAATGACCTCAAAGCC (SEQ ID NO: 9)) was used to prime synthesis of first strand cDNA by reverse transcription of 0.8 μg of total RNA isolated from AtT20 cells in a 25 μl reaction containing 20 mM Tris.HCl (pH 8.4), 50 mM KCl, 3 mM $MgCl_2$, 10 mM DTT, 100 nM primer 1, 400 μM each dNTP and 200U Superscript II Reverse Transcriptase at 42° C. for 30 minutes. First strand cDNA was purified away from this primer using the Glass-Max purification system (GIBCO) and one-fifth of the purified cDNA 3'-tailed with dCTP using 10U terminal deoxynucleotide transferase (TdT) in a 25 μl reaction containing 20 mM Tris.HCl (pH 8.4), 50 mM KCl, 1.5 mM $MgCl_2$, 200 μM dCTP at 37° C. for 15 minutes. Following heat inactivation of the TdT a second strand cDNA synthesis reaction was primed by the anchor primer supplied with the 5' RACE system kit present at 200 nM and carried out as for first strand synthesis. Double-stranded cDNA was subsequently purified using the GlassMax system and one-fifth of this preparation used as a template in PCR containing 20 mM Tris.HCl (pH 8.4), 50 mM KCl, 1.5 mM $MgCl_2$, 200 mM each dNTP, 200nM each of universal amplification primer (UAP; supplied with the kit) and jp134-specific nested anti-sense primer 2 (SEQ ID NO: 10) (GCCTCTGCACAGCTGCAGTGGGACTCC) and 0.03U/μl Amplitaq DNA polymerase (Perkin Elmer) (parameters for all the PCR reactions can be found in Table II). A second round of PCR using 0.05% of the primary PCR reaction (or 0.05% of size-selected primary PCR products) as a template was performed as described above except jp134-specific nested anti-sense primer 3 (SEQ ID NO: 11) (CCTGGCAGAACTGCTCGATGGCTTTTATCATGC) was substituted for primer 2. This first round of 5' RACE-PCR yielded a product of approximately 1 kb which was purified from an agarose gel and ligated into the plasmid vector pGEM-T (Promega, Madison, Wis., U.S.A.). Although DNA sequence analysis of this fragment (from both strands of two independent clones) extended the open reading frame observed in jp134 by 842 bp no suitable initiator codon was yet apparent. Another set of three anti-sense primers was designed on the basis of sequence data from the 5' end of the 1 kb fragment obtained from the first round and used in a second round of 5' RACE-PCR performed as described above except that 1) the first strand cDNA was synthesized at 50° C. for 30 minutes and 2) substitution of primers 1, 2 and 3 with 4 (SEQ ID NO: 12) (GGAGAAGCTTCCTACTTG), 5 (SEQ ID NO: 13) (GTGGCCGTGAGAGTATGATTGGAGCTGTC) and 6 (SEQ ID NO: 14) (GTCCAAACCTGAAACTGCGC ACGCAG), respectively. This yielded a product of approximately 650 bp which, when cloned into pGEM-T and several independent isolates sequenced, completed the open reading frame encoding the novel mouse adenylyl cyclase.

Detection of mRNA Expression

Northern analysis was performed using standard procedures. Briefly, 20 μg of total RNA was separated by formaldehyde gel electrophoresis and transferred by blotting onto positively charged nylon membrane (Appligene, Ullkirch, France) then fixed by baking at 80° C. and prehybridised at 42° C. for 2 hours in 50% deionised formamide, 5×SSPE, 0.5×Denhardt's, 0.1% w/v SDS, 0.2 mg/ml denatured salmon sperm carrier DNA and 10% Dextran sulphate. Random-primed labelled DNA probe (50 ng; >$10^9$ cpm/μg) was then added and hybridisation continued overnight at 42° C. The membrane was washed twice for 20 minutes in 2×SSC/0.1% SDS, followed by 20 minutes in 1×SSC/0.1% SDS at 42° C. and finally 20 minutes in 0.5×SSC/0.1% SDS at 50° C. before wrapping in plastic an exposing to autoradiographic film at −70° C. Ribonuclease protection assays were performed using an RPA II kit (Ambion, AMS Biotechnology, Witney, Oxon, U.K.) according to the manufacturer's instructions. Briefly, 10 μg of total RNA was hybridised overnight at 45° C. to $10^5$ cpm of radiolabelled anti-sense riboprobe. Following hybridisation, reactions were digested with single-strand-specific RNase and protected fragments resolved on a 6% denaturing polyacrylamide gel which was fixed for 30 minutes in 15% methanol/5% acetic acid, dried and exposed to autoradiographic film at −70° C.

Results and Discussion

Analysis of the cDNA and Amino Acid Sequence

The sequence of the full length cDNA isolated from AtT20 cells (sense strand on top) and the deduced primary structure of AC are shown in SEQ ID No 1. A 4473 bp cDNA containing a 4062 bp open reading frame which encodes a 1352 amino acid protein. A stretch of 10 amino acids near the 5' end of the cDNA strongly resembles the Kozak consensus sequence for initiation of translation and contains the presumed initiator codon of the novel adenylyl cyclase protein. The presence of a translational stop codon upstream of this methionine residue suggests that the complete open reading frame encoding this protein has been cloned. The deduced amino acid sequence between residues 1105 and 1192 appears to be identical (except for a single asparagine to aspartic acid switch at 1191) to a short sequence derived from mouse brain RNA reported in preliminary form (Premont (1994) Meth. Enzymol. 238:116–127) and designated as AC. Although this region of the enzyme contains at least two highly preserved stretches of amino acid sequence common to all cyclases, on the basis of the abundance of AC mRNA in the brain (see below) it seems plausible that the full sequence reported here corresponds to the same enzyme and will subsequently referred to as AC.

Figure 9:
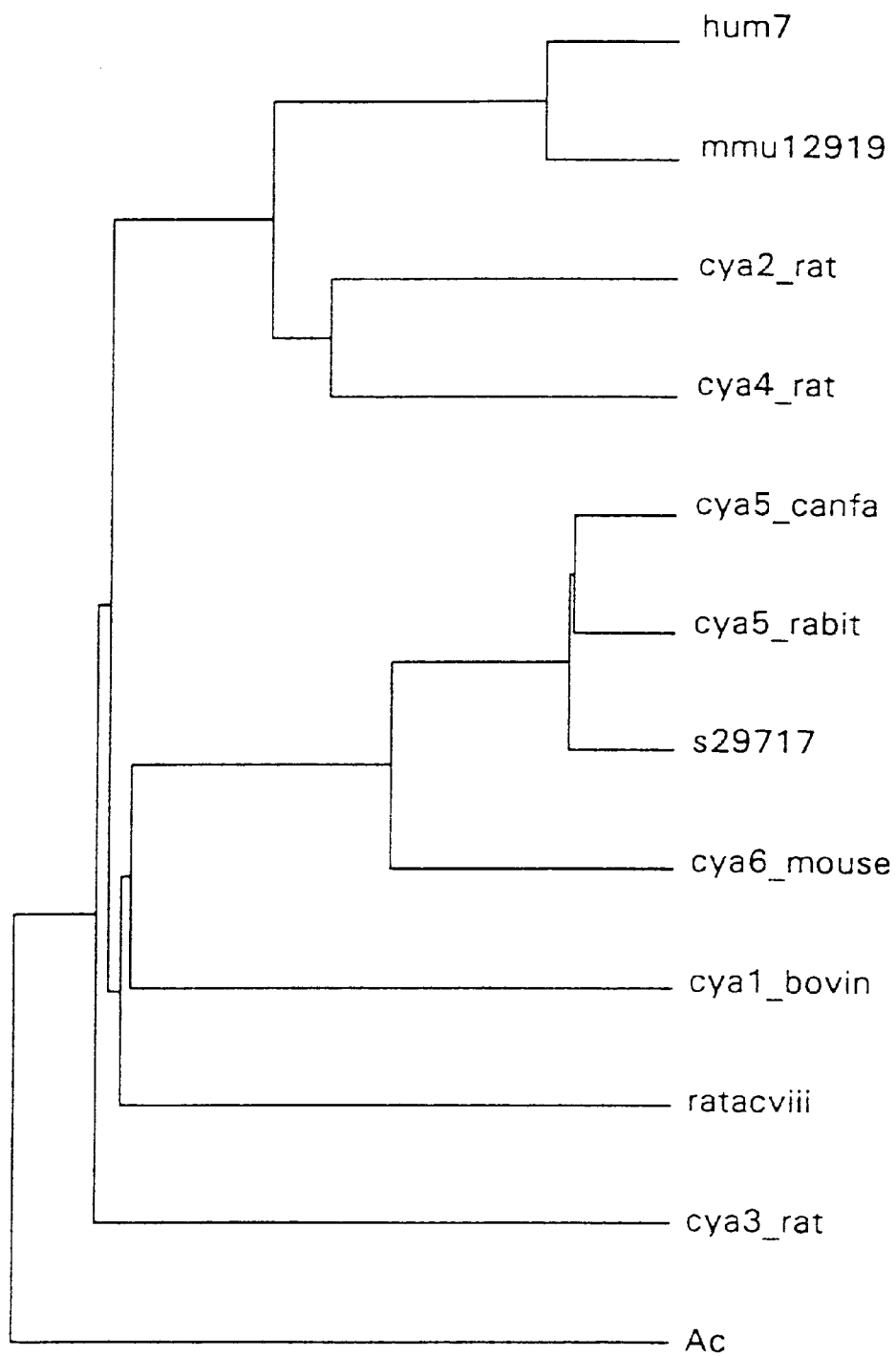

While the key adenylyl cyclase consensus sequences thought to be involved in catalytic activity (Taussig et al, (1995) J. Biol. Chem. 270:1–4) are well conserved in AC, overall amino acid sequence homology comparisons indicate that AC is not sufficiently similar to currently known cyclases to be placed within one of the previously suggested subfamilies as illustrated by FIG. 9. Therefore AC represents a sixth adenylyl cyclase subfamily. It cannot be excluded at present that perhaps other members of this subfamily exist.

Figure 10:
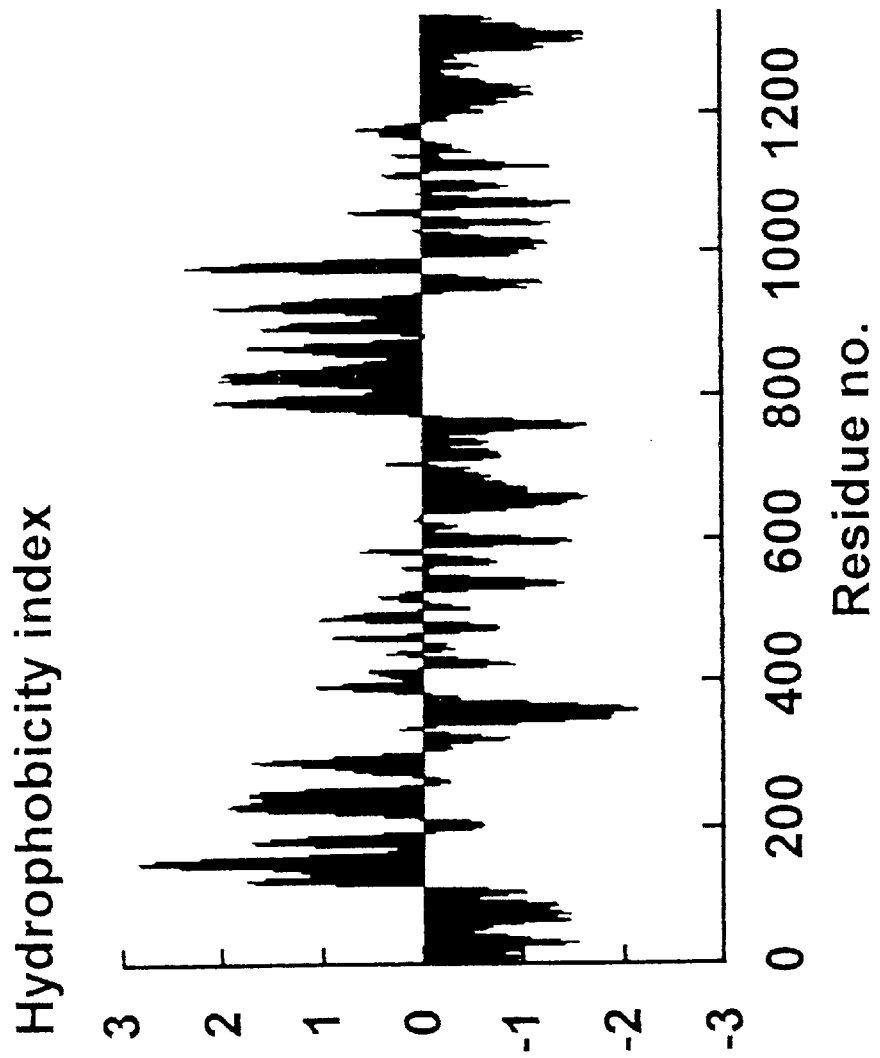

Hydrophobicity plots (Kyte et al, (1982) J. Mol. Biol. 157:105) return the previously reported adenylyl cyclase structure (FIG. 10) a short N-terminal loop followed by two homologous segments each consisting of a hydrophobic chain with 6 intermembrane helices and a large hydrophilic (putative cytoplasmic) loop. The first cytoplasmic loop appears considerably longer (by about 130 amino acids) in AC than previously reported for other isotypes.

Analysis of putative phosphorylation sites (Pearson et al, (1991) Meth. Enzymol. 200:61–81) indicates several strong consensus protein kinase A and protein kinase C sites as well as two casein kinase phosphorylation sites (Table 3). Elements of the functionally relevant calmodulin binding site identified in ACtypeI (Wu et al, (1993) J. Biol. Chem. 286:23766–23768 and Vorherr et al, (1993) Biochemistry (U.S.A.) 32:6081–6088) can be discerned on the basis of conserved amino acid residues at positions 504–505 in the first cytoplasmic domain. However, two important basic residues Lys500 and Lys497 which are part of the calmodulin binding site in ACtypeI are substituted by Gly in AC making calmodulin binding unlikely in this region of the enzyme.

Distribution of mRNA for AC in Rat Tissues and Mouse Brain

Ribonuclease protection analysis of rat tissues showed hybridizion of total RNA with probe JP114 gave a 125 bp double stranded product that was most abundant in brain, with significant hybridizing activity in the anterior pituitary gland, the ovary, the adrenal gland, the lung and the kidney. Liver, pancreas,spleen, thymus, heart gave no detectable signal, suggesting that the distribution of the enzyme is highly tissue specific.

Gross dissection of the mouse brain suggests that AC mRNA is most abundant in the cortex, striatum and the hippocampus, with lower levels in the cerebellum and much lower but detectable concentrations in the olfactory bulb, the diencephalon, the brain stem and the pituitary gland. It is of note that the RNAse resistant hybrid in mouse tissues and AtT20 cells is larger, about 155 bp, than in rat tissues indicating interspecies sequence variation(s) in this region of the enzyme.

Northern mRNA analysis showed an approximately 9 kb size RNA in AtT20 cells that hybridizes with a JP114 antisense $^{32}$P-DNA probe.

In summary, the present results show the existence of a further member of the adenylyl cyclase family of proteins, which has a restricted tissue distribution and a distinct regional pattern in the brain. The functional properties of this cyclase have yet to be explored in detail. Pharmacological analysis (Antoni et al, (1994) Journal Of Physiology-London 475p:137–138 and Antoni et al, (1995) EMBO Journal submitted) indicates that AC is inhibited by $Ca^{2+}$ through calcineurin and that this may be relevant for corticosteroid inhibition of corticotropin secretion in anterior pituitary cells (Shipston et al, (1994) Ann. N.Y. Acad. Sci. 746:453–456). Furthermore, the abundance of AC mRNA in the striatum and hippocampus, where calcineurin is particularly abundant relative to other regions of the brain (Kuno et al, (1992) J. Neurochem. 58:1643–1651) is of interest with respect to synaptic function.

Summary

The cDNA of a novel adenylyl cyclase isotype (AC) has been cloned and sequenced from the mouse pituitary corticotrope tumour cell line AtT20. Adenylyl cyclase cDNA sequences were amplified from AtT20 cells using degenerate primers bracketing a highly conserved motif near the carboxyl terminus region of the protein. The majority of the sublcloned amplified cDNA products revealed a novel sequence which was utilized to screen an AtT20 cell cDNA library, from which a 3120 bp clone was isolated and sequenced. The full length coding sequence was obtained upon two rounds of 5' RACE-PCR, yielding a 4473 bp long cDNA containing an open reading frame of 4062 bp which encodes a protein of 1352 amino acids. The hydrophobicity profile of this protein resembles that of other members of the adenylyl cyclase family in that two sets of six hydrophobic, putatively membrane-spanning regions are predicted as well as a large central cytoplasmic loop and long C-terminal cytoplasmic tail. Amino acid sequence comparisons suggest that this novel enzyme is quite distinct from other known mammalian adenylyl cyclases and cannot be easily assigned to any of the previously observed subfamilies. Tissue distribution of mRNA was examined by RNAse protection assay and indicated the highest abundance of this novel adenylyl cyclase to be in the brain followed by anterior pituitary gland, ovary and adrenal gland, which appeared to express approximately equal levels. Low level expression of this mRNA was detected in lung and kidney while in the heart, liver and pancreas none was apparent. Within the brain, relatively high levels of novel adenylyl cyclase mRNA were detected in cortex, hippocampus, striatum, cerebellum, with much less in diencephalon, olfactory bulb and the brain stem.

EXAMPLE 3

Functional Properties of AC

Method

The complete coding sequence of AC was subcloned into the eukaryotic expression vector pcDNA3 (Invitrogen). The cDNA clone for the $CRF_1$ receptor cloned into the vector pcDNAI (Chang et al, (1993) Neuron 11:1187–1195) was a gift of Drs. R. V. Pearse II and M. G. Rosenfeld (University of California, San Diego). Both expression plasmids (10 µg) were transfected into SV40-transformed monkey embryonic kidney (COS-7) cells grown in DMEM and 10% fetal bovine serum to 70% confluency in 75 cm² flasks following the double DEAE-dextran transfection protocol (Ishikawa et al, (1992) Nucl. Acids Res. 20:4367), while only AC cDNA was transfected into adenovirus-transformed human embryonic kidney (HEK293) cells as these express endogenous receptors for CRF (F. A. Antoni, unpublished data). In control transfections pcDNA3 vector DNA replaced the AC expression construct. Forty-eight hours after the second transfection the cells were harvested in Hank's $Ca^{2+}$ and $Mg^{2+}$free balanced salt solution containing 0.1% EDTA and centrifuged at 200×g, for 10 minutes. Following resuspension the cells were centrifuged again to remove serum proteins and resuspended in 1 ml of HEPES (25 mmol/l, pH 7.4) buffered Hank's balanced salt solution and a 50 µl aliquot was removed for the measurement of protein content. The cells were then diluted further with 4ml of HEPES buffered Hank's solution containing 0.25% BSA, and pre-incubated for 1 hour at 37° C. under air. Subsequently the cells were pelleted again and distributed (final concentration $3 \times 10^5$ cells/ml) into polypropylene vials and processed as AtT20 cells except that 1 mmol IBMX and 0.1 mmol/l rolipram were used as inhibitors of cAMP-degrading phosphodiesterases (see Example 1).

Figure 11:
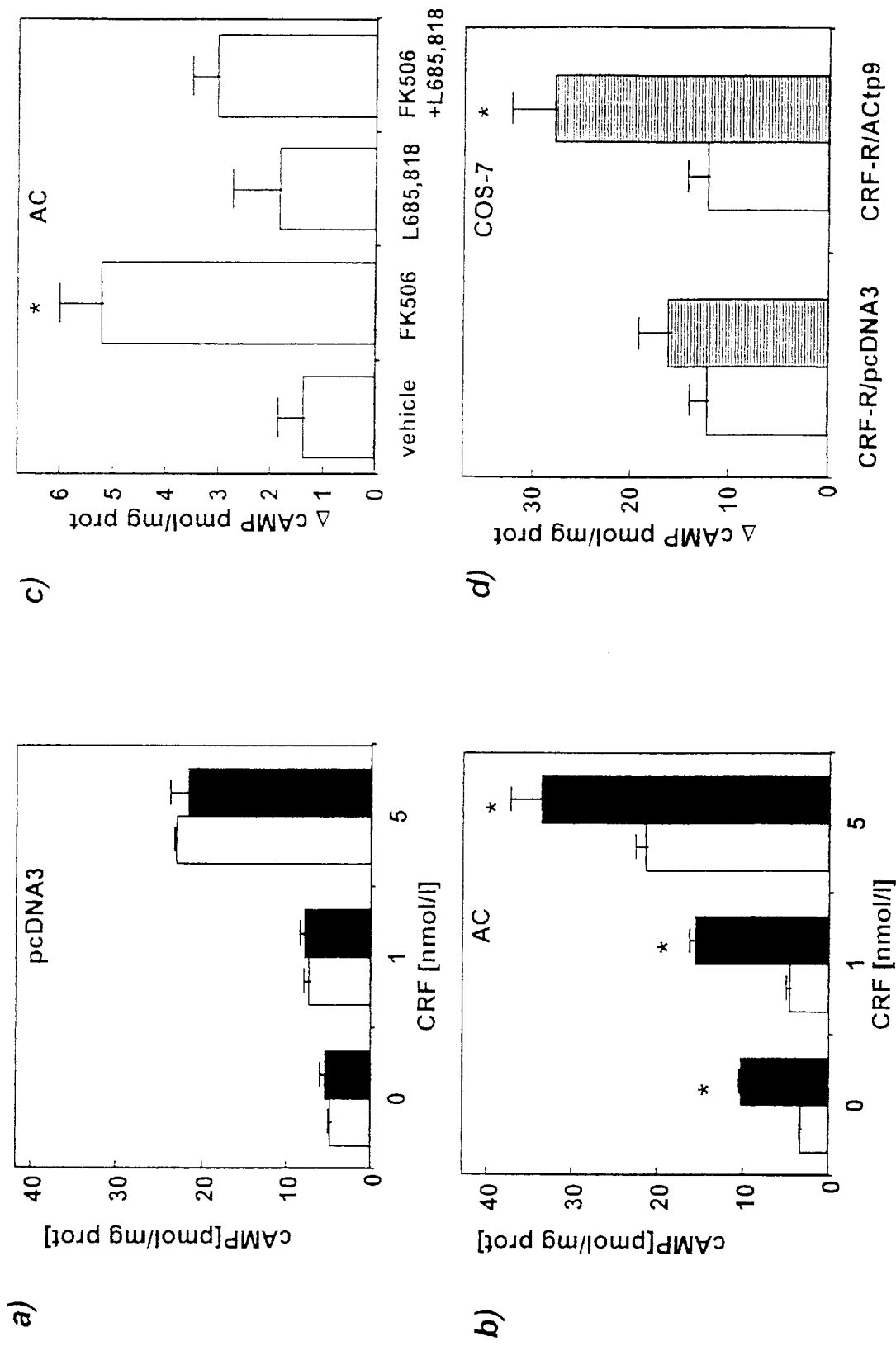

The functional properties of the cloned AC10 were investigated in transiently transfected HEK293 and COS7 cells (FIG. 11). In HEK293 cells which have endogenous receptors for CRF, unstimulated levels of cAMP and the cAMP response to CRF were unchanged upon transfection with AC (FIGS. 11a and b). However, preincubation with FK506 increased unstimulated cAMP levels 3-fold and significantly enhanced the cAMP response to 1 but not to 5 (FIG. 11b) or 25 nmol/l CRF (not shown). These effects were specific to cells transfected with AC (FIGS. 11a and b). Surprisingly, in cells transfected with AC 100 µmol/l L-685,818 increased unstimulated cAMP levels to the same extent as 2 µmol/l FK506, while having no effect in sham-transfected or pcDNA3-transfected cells (not shown). Importantly, L-685,818 had no significant effect on CRF-induced cAMP production but blocked the enhancement of the response to 1 nmol/l CRF by FK506 in cells transfected with AC (FIG. 11c). Slightly different results were obtained in COS7 cells. In this system unstimulated cAMP production in cells transfected with AC cDNA (without or in combination with the CRF receptor) was 1.9-fold higher than in controls receiving vector DNA (unstimulated cAMP [pmol/mg protein] in COS7 cells transfected with CRF receptor and pcDNA3:20.9±0.2; with CRF receptor and AC cDNA: 38.2±3.4; mean±SEM, n=4/group P<0.001, Student's t-test, representative of 4 separate experiments) whereas the increment produced by CRF (1–25 nmol/l) was not consistently altered (FIG. 11d and data not shown). Preincubation with cyclosporin A significantly and selectively enhanced the cAMP response to 1 nmol/l CRF in cells transfected with AC (FIG. 11d).

These data confirm that the cDNA for AC encodes a cAMP generating enzyme. At this point the cause of the differences in unstimulated cAMP production between COS7 cells and HEK293 cells is unknown, however, such discrepancies are not unprecedented in eukaryotic expression systems (Premont (1994) Meth. Enzymol. 238:116–127; and Adie et al, (1994) Biochem. J. 303:803–808). With respect to the paradoxical effect of L-685,818 on unstimulated cAMP levels, it is likely that it has some calcineurin inhibiting activity at a high concentration (100 µmol/l) which may be sufficient to enhance basal cAMP production. However, this small inhibitory effect is not enough to cause a functionally relevant reduction of activity when calcineurin is activated by the cAMP-induced increase of intracellular free $Ca^{2+}$ that is known to occur upon a cAMP stimulation in both HEK293 and COS7 (Lin et al, (1995) Mol. Pharmacol. 47:131–139; and Widman et al, (1994) Mol. Pharmacol. 45:1029–1035 (1994)) cells. The consistent finding of the transient transfection experiments is that cAMP production in response to low CRF concentrations is enhanced by immunosuppressant blockers of calcineurin and, in the case of FK506, this is blocked by the antagonist L-685,818. In this respect the findings with cloned and transiently transfected AC are in good agreement with the findings in AtT20 cells and with pilot studies in HEK293 cells stably transfected with AC (Antoni et al, unpublished data).

Sequence Comparison
Method

Comparisons with other adenylyl cylases were made using the GCG package available from the Human Genome Mapping Programme, Cambridge U.K. Initial alignments with FKBP12 were made using GeneJockeyII (Biosoft, Cambridge U.K.), and adjusted visually by the aid of the programme.

Figure 12:
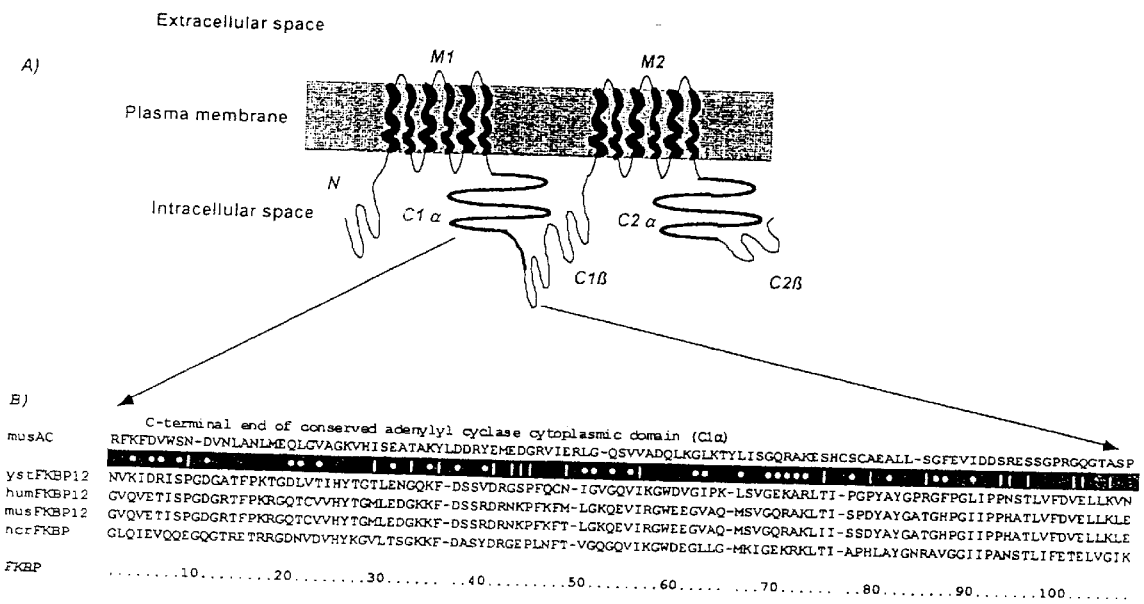

Closer examination of the primary sequence of AC revealed that residues 503 to 610 in the first cytoplasmic loop show approximately 40% similarity with FKBP12 (FIGS. 12a and b). The first part of this FKBP12-like segment consists of the C-terminal segment of the C1α domain which is highly conserved in all adenylyl cyclases (residues 503–570 in FIG. 12c) (Taussig et al, (1995) J. Biol. Chem. 270:1–4). The second part is the beginning of the long non-conserved segment (C1β domain). Importantly, some of the sequence identities correspond to Asp37, Gly86, Phe87, Ile90 in FKBP12 (FIG. 12b) and are amino acid residues of key importance for the high-affinity interaction of the FK506/FKBP12 complex with calcineurin (Aldape et al, (1992) J. Biol. Chem. 267:16029–16032; Yang et al, (1993) J. Am. Chem. Soc. 115:819–820; and Braun et al, (1995) FASEB J. 9:63–72). The best overall sequence similarity is observed with yeast FKBP12, which in fact has been shown to bind calcineurin in the absence of FK506 (Cardenas et al, (1994) EMBO J. 13:5944–5957). Given the prominent actions of calcineurin blocker immunosuppressants on cAMP formation in systems expressing AC it seems reasonable to suggest that $AC_{(503-610)}$ may be a physiologically relevant docking site for calcineurin.

Adenylyl cyclase type 1 (ACtp1) is also thought to interact directly with a protein co-factor distinct from G-protein subunits as this cyclase is markedly stimulated by $Ca^{2+}$/calmodulin (for review see Taussig et al, (1995) J. Biol. Chem. 270:1–4). Residues 495–522 of ACtp1 (495–518 shown underlined in FIG. 12c) bind calmodulin with nanomolar affinity (Vorherr et al, (1993) Biochemistry (U.S.A.) 32:6081–6088). Moreover, point mutations of $Phe_{503}$ and $Lys_{504}$ virtually abolish the stimulatory effect of $Ca^{2+}$/calmodulin on this cyclase (Wu et al, (1993) J. Biol. Chem. 286:23766–23768). Intriguingly, the position of residues 495–522 along the cytoplasmic loop of AC corresponds to the C-terminal part of the FKBP12-like sequence in AC (FIG. 12c). It seems therefore that the junction between the C1α and C1β domains in adenylyl cyclase 1 and in AC is a site of allosteric regulation by calcium binding proteins. In the case of AC a strong candidate for such a regulatory protein is calcineurin.

AC is Enriched in Nerve Cells
Method

Northern analysis of total RNA (20 µg per lane) was performed by transfer onto positively charged nylon membrane (Appligene, Ullkirch, France) then hybridized to radio-labelled probe in 50% formamide and washed according to standard procedures (Sambrook et al, Molecular Cloning: a Laboratory Manual Ed. 2 (Cold Spring Harbor Press, U.S.A., 1989)). The cDNA probes used correspond to amino acid residues 1–195 (JP164) and 1105–1165 (JP114).

Ribonuclease protection assays were performed using an RPA II kit (Ambion, AMS Biotechnology, Witney, Oxon, U.K.) according to the manufacturer's instructions using radio-labelled anti-sense riboprobe derived from JP114 or JP142 (corresponding to amino acids 320–478). The AC probes showed no significant cross hybridisation in Southern analysis with adenylyl cyclase isotype cDNAs 1, 2, 3, 5 or 6. A 250 bp probe hybridising with β-actin was used as the internal standard to correct for differences in RNA loading. Blots and gels were exposed to X-ray film as well as to Molecular Dynamics Phosphorimager casettes and quantified with the ImageQuant software using the 28S RNA band and the β-actin band as standards for RNA loading in Northern and RNase protection analysis, respectively. Division of the integrated volume of pixels of the selected radiolabelled band with the integrated volume of the internal standard band yields the relative hybridisation intensity, which was used to compare the intensity of labelled RNA bands within blots. The relative abundance of the protected RNA species in a given tissue is expressed as the percentage of the relative hybridisation intensity of the whole brain RNA band run in the same assay.

Importantly, we have discovered that AC mRNA is present in relatively high levels in the hypothalamic paraventricular nucleus that contains the major contingent of CRF41 and vasopressin producing neuroendocrine motoneurones and controls the secretion of ACTH by the anterior pituitary gland. In addition, the levels of mRNA are apparently controlled by adrenal corticosteroids, so that lowering of adrenocortical steroid levels causes an increased expression of AC mRNA. This reinforces the notion that AC is expressed in areas of the brain important for the negative feedback action of adrenal corticosteroids, in the hypothalamic-pituitary-adrenocortical axis. This system is a servomechanism where, when corticosteroid feedback is detected as inadequate by the relevant as yet unidentified components of the system, the levels of AC mRNA are increased.

Results

Figure 13:
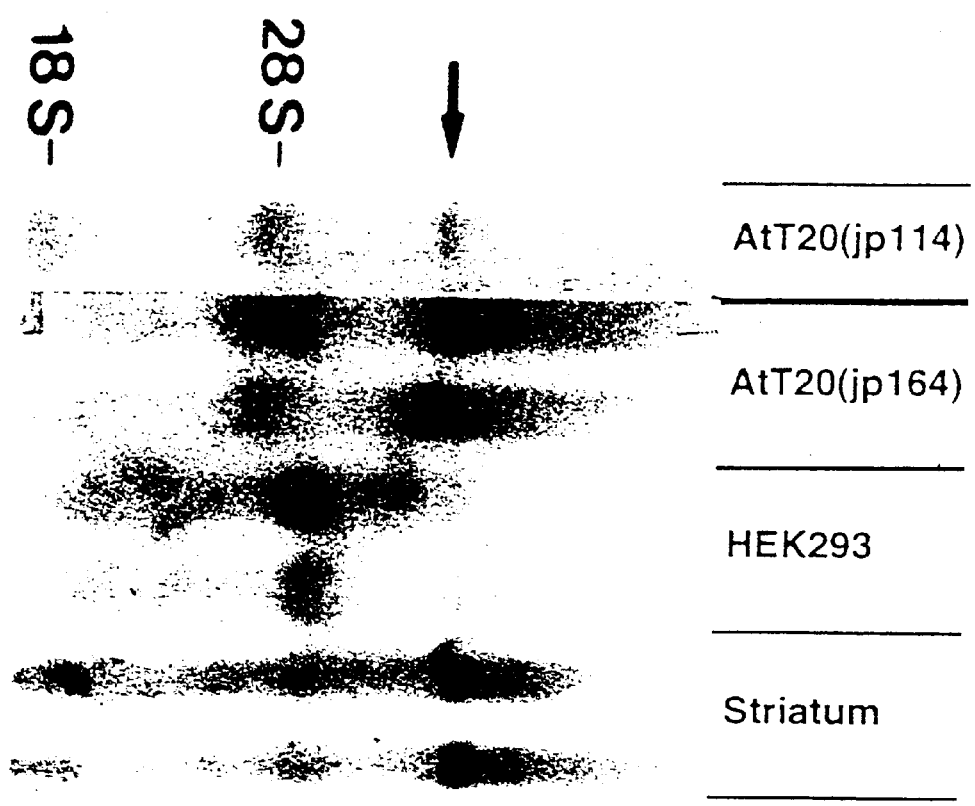
Figure 14:

Existence of a calcineurin-regulated adenylyl cyclase is of great potential significance for brain function as calcineurin constitutes about 1% of total brain protein (Klee et al, (1988) Adv. Enzymol. 61:149–200). AC is in fact highly abundant in the brain: Northern blot analysis shows the presence of a 9 kb mRNA in mouse striatum and AtT20 cells (FIG. 13). RNAse protection anaylsis of dissected regions of the mouse brain suggest the relative abundance of AC mRNA to be hippocampus≧striatum≧cortex≧cerebellum≧olfactory bulb>brain stem>diencephalon≧anterior pituitary gland (range 3-fold, see FIG. 13 for methods). These findings indicated a primarily neuronal localisation which was confirmed by in situ hybridisation histochemistry, showing robust AC mRNA hybridisation in hippocampal neurons (FIG. 14).

RNAse protection assay also shows the presence of AC10 mRNA, amongst other tissues, in mouse kidney, thymus and spleen (relative abundance 50, 10 and 8%, respectively if brain=100%, see FIG. 13 for methods) all of which are important targets of immunosuppressants (Schreier et al, (1993) Transplant. Proc. 25:502–507; and Dumont et al, (1992) J. Exp. Med. 176:751–760).

Functional Implications of Calcineurin Regulated Adenylyl Cyclase

In summary, the present results show the existence of a new member of the adenylyl cyclase family of proteins that is abundant in the brain and is inhibited by calcineurin. The intricate control of calcineurin activity by its EF-hand protein β-subunit as well as additional regulation by calmodulin (Schreier et al, (1993) Transplant. Proc. 25:502–507) suggest a potentially fundamental role for AC in situations where fine interplay between intracellular $Ca^{2+}$ and cAMP determines cellular function (Cooper et al, (1995) Nature 374:421–424). Furthermore, the abundance of AC mRNA in the striatum and hippocampus, where calcineurin is particularly enriched relative to other regions of the brain (Kuno et al, (1992) J. Neurochem. 58:1643–1651) is of major interest with respect to synaptic function. Finally, it remains to be explored whether or not the currently known $Ca^{2+}$ regulated cyclases are also subject to control by calcineurin. A recent study has in fact reported the facilitation of cAMP formation by $Ca^{2+}$/calcineurin suggestive of calcineurin control of a $Ca^{2+}$-stimulated adenylyl cyclase (Baukal et al, (1994) J. Biol. Chem. 269:24546–24549).

EXAMPLE 4

Human AC9

Isolation of a Complete Human AC9 cDNA Clone

Figure 18:
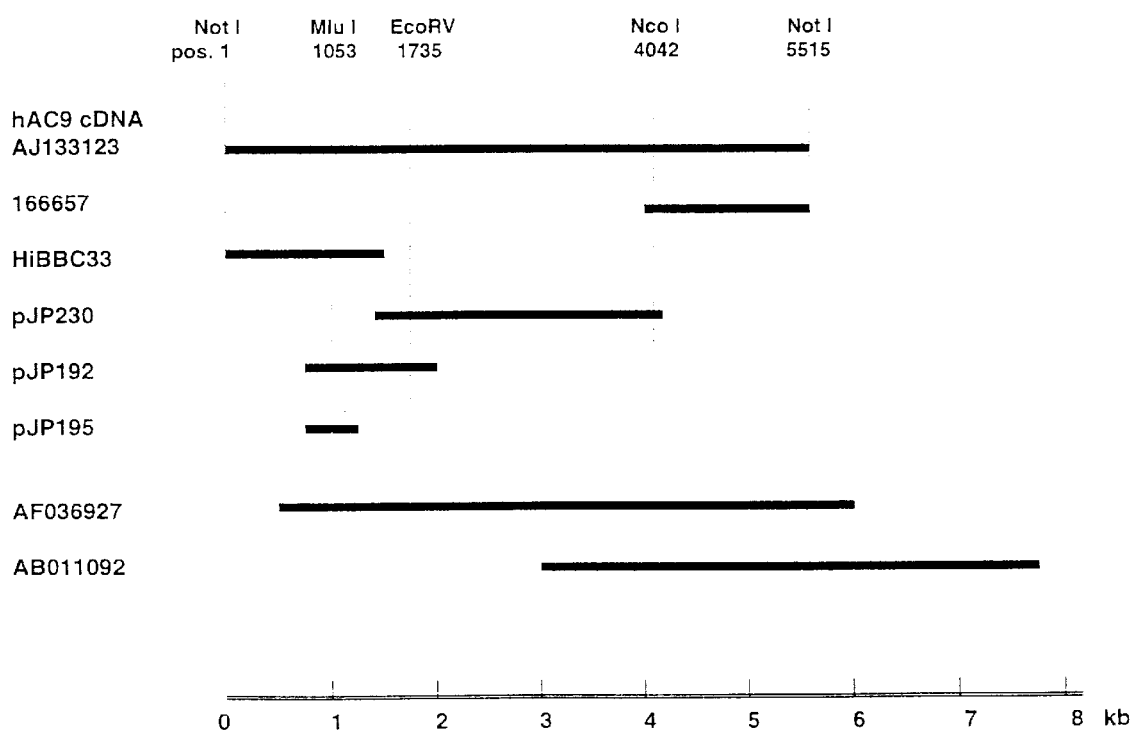

The assembly of a full length human AC9 cDNA clone is represented in FIG. 18. The NCBI BLAST computer program (http://www.ncbi.nlm.nih.gov/BLAST/) was used to search the GenBank/EMBL and dbEST (expressed sequence tag) DNA sequence databases for human EST clones exhibiting similarity to mouse AC9 cDNA sequence Z50190. Two entries of interest were initially identified under GenBank/ EMBL Accession Numbers R88632 and T08314. The EST cDNA clones, IMAGE 166657 (from adult human brain) and HIBBC33 (from infant human brain), from which these sequences were derived, were respectively obtained from the MRC Human Genome Mapping Project Resource Centre (MRC HGMP-RC, Cambridge, UK) and The Institute for Genome Research (TIGR, Gathersburg, Md., U.S.A., distributed by ATCC, Rockville, Md., U.S.A.). Due to the directed nature of cDNA cloning (Adams et al, (1993) Nat. Genet. 4: 373–80) the database sequence entries for these clones was presumed to represent part of the sense strand of the cDNA. This holds true for sequence R88632 (258 bp) which exhibits 77% sequence identity with nucleotides 3855 to 4113 of mouse AC9 sequence Z50190. However, sequence T08314 (228 bp) exhibited 82% identity with residues 682–909 on the anti-sense strand of mouse AC9 sequence Z50190 suggesting that this cDNA was cloned randomly rather than directionally. This insert may have arisen due to fragmentation of cDNA prior to vector ligation or as a result of mis-priming of cDNA synthesis from a source other than the polyadenylated 3' end of mRNA although a complete sequence representing the primer of cDNA synthesis (Adams et al, (1993) supra) was not found. The inserts of both EST clones were completely sequenced by the dideoxynucleotide method using universal and sequence-specific primers using an ABI Prism dye terminator DNA cycle sequencing kit (Perkin Elmer), resolved on a 4.75% acrylamide denaturing gel and data collected on an Applied Biosystems/Perkin Elmer 373 Stretch automated sequencer. Sequences were analyzed independently using Gene Jockey II program (Biosoft, Cambridge, U.K.) for the assessment of errors and visual confirmation of base calling. IMAGE clone 166657 was found to contain the 3' part of an open reading frame (ORF) encoding human AC9 followed by an untranslated region (UTR) and polyadenylated tail. Clone HIBBC33 contained 5' UTR sequence and the 5' part of the ORF encoding human AC9. To complete cloning of the human AC9 cDNA, the gap between these EST cDNA clones containing the 5' and 3' parts of the ORF were isolated by polymerase chain reaction (PCR) amplification using the High Fidelity Expand PCR system (Boehringer Mannheim/ Roche) with sequence-specific primers. A PCR product of 2860 bp (1309–4169; pJP230) was amplified from a denatured human skeletal muscle cDNA library (Clontech) using primers 5'-GAC CTT TGG CTA CCA TTT CCG GGA TG-3' (SEQ ID NO: 100) and 5'-CTT CGC TCA CCT GGA TGC GGC ACT C-3' (SEQ ID NO: 101) respectively. The ends of this PCR product were blunt ended with T4 DNA polymerase (Boehringer Mannheim/Roche) prior to ligation into the SmaI site of plasmid vector pUC9 and subsequently sequenced as above. Additional overlapping clones of PCR products derived from human AC9 cDNA (853–1196; pJP 192 and 853–1167; pJP195), amplified as above or from a pool of denatured human cDNA libraries (Clontech) using primers based on mouse AC9 cDNA (upstream primer 5'-GGA GCG CTG CTT TCC GCA G-3' (SEQ ID NO: 102) with downstream primers 5'-CAT GTT CAC CAT CTC TTT CTT CTC C-3' (SEQ ID NO: 103) and 5'-GTG GCC GTG AGA GTA TGA TTG GAG CTG TC-3' (SEQ ID NO: 104) respectively), were propagated in the TA cloning vector pCRII (Invitrogen) and sequenced as above. The complete human AC9 cDNA (5515 bp, including 5' and 3' Not I cloning sites) was assembled from the above clones using recombinant DNA techniques. Internal PCR products pJP192 and pJP230 were joined at EcoRV site; 1735. The resulting clone was joined to the 5'UTR, initiation codon and 5' part of the ORF in clone HIBBC33 at MluI site; 1053. Finally the insert from clone IMAGE 166657 containing the 3' ORF and UTR was joined to the above clone at NcoI site; 4042 and the complete cDNA cloned as a NotI fragment into pBluescript (Stratagene) and the expression vector pcDNA3 (Invitrogen) for use in subsequent experiments.

Functional Expression of Human AC9

The complete coding sequence of human AC9 was cloned into the expression vector pcDNA3. This constuct and pcDNA3 (10 µg) were each linearised by PvuI digestion prior to electroporation into HEK293 cells. Stably transfected clones were selected for resistance to G418 (Gibco) at 0.6 µg/ml in Dulbecco's modified Eagle's medium (DMEM) supplemented with 10% foetal calf serum. A total of 12 clones were expanded and over-expression of human AC9 confirmed in 9 cell lines by immunoblotting using antisera raised against a pentadecapeptide derived from the N-terminus of mouse AC9 (Paterson et al, (1995) Biochem. Biophys. Res. Commun. 214:1000–8). All but one of these 9 clones showed the inhibitory effects of $Ca^{2+}$ on cAMP accumulation assayed in the presence of cyclic nucleotide phosphdiesterase (PDE) blockers (Antoni et al, (1998) J. Neurosci. 18:9650–61). Analysis of clone 7 is reported here.

HEK-293 cells display complex intracellular $Ca^{2+}$ handling mechanisms that may be controlled by cAMP and calcineurin (Lin et al, (1995) Mol. Pharmacol. 47:131–9; Gromada et al, (1995) FEBS Letts. 373:182–6; Querfurth et al, (1998) Biochem J. 334:79–86), and thus complicate the interpretation of the data. Therefore, intracellular stores of $Ca^{2+}$ were depleted to reduce the contribution of intracellular $Ca^{2+}$ pools to the intracellular free $Ca^{2+}$ signal. All procedures were carried out at 37° C., where required, immunosuppressant drugs FK506 (courtesy of Fujisawa GmbH, Munich, Germany) cyclosporin A (courtesy of Novartis Ltd, U.K.) and L685,818 (Courtesy of Merck & Co, Rahway, N.J.) rapamycin (courtesy of Dr Hans Fliri, Sandoz Pharma, Basel, Switzerland) or ethanol vehicle (0.1% v/v) were added to the medium at the onset of the $Ca^{2+}$ depletion period. Two different $Ca^{2+}$ depletion protocols were used (Antoni et al, (1998) supra). In the first, cells were incubated in a balanced salt solution containing (mM) 133 NaCl, 5.4 KCl, 0.25 $Na_2HPO_4$, 0.44 $KH_2PO_4$, 1 $MgSO_4$, 2 EGTA, 5.6 D-glucose, 25 Hepes pH7.40 and 0.1% (w/v) bovine serum albumin (HBSS/EGTA) with 10 µM ryanodine and 1 µM thapsigargin (both from LC Labs, Boston, Mass.). These conditions deplete rapidly exchangeable $Ca^{2+}$ pools and activate capacitative $Ca^{2+}$ entry mechanisms (Cooper et al, (1994) Cellular Signalling 6:823–40). In the second protocol 5 µM 4-Br-A23187 was used instead of ryanodine and thapsigargin, and Ca/EGTA was added to obtain similar initial levels of $[Ca^{2+}]_i$ as in the studies with ryanodine and thapsigargin. Under these conditions intracellular $Ca^{2+}$ pools are depleted and, in addition to capacitative $Ca^{2+}$ entry, $Ca^{2+}$ influx may take place through the pores formed by the ionophore. The cells were incubated in $Ca^{2+}$-depleting medium for 20 min. Subsequently HBSS/EGTA containing various amounts of $CaCl_2$ (Ca/EGTA) was added to achieve extracellular concentrations of $Ca^{2+}$ ranging between 0.125–2 mM. The pH of this solution was 7.65 in order to minimize the change of pH due to the displacement of protons from EGTA—a pH shift from 7.40 to 7.29 occurred upon achieving a free $Ca^{2+}$ concentration of 2 mM. After Ca/EGTA was added, the cells were incubated for 5 min after which the cyclic nucleotide PDE inhibitors isobutylmethylxanthine (IBMX, Aldrich, Gillingham, Dorset, U.K.) and rolipram (courtesy of Dr H Wachtel, Schering AG, Berlin Germany), 1 mM and 0.1 mM respectively, were introduced. Unless indicated otherwise, the cells were incubated for a further 10 min and the incubation was then terminated by the addition of 0.2M HCl. The total cAMP content of the cells and the medium was determined after freeze-thawing and acetylation by radioimmunoassay (Antoni et al, (1995) J. Biol. Chem. 270:28055–61).

Analysis of Human AC9 mRNA Expression Northern Blotting

A multiple tissue northern blot (MTN; Clontech) of poly $A^+$RNA from human heart, brain, placenta, lung, liver, skeletal muscle, kidney and pancreas (2 µg per lane) was probed with a 528 bp SmaI-MluI fragment from the 5' end of the human AC9 cDNA and subsequently with a human β-actin cDNA control probe supplied with the blot (each labelled with 32P-dCTP by random priming; Pharmacia "Ready-to-Go" system). Hybridization was carried out in Express Hyb solution (Clontech) according to the manufacturers instructions at 68° C. for 1 hour, washed in 2×SSC/0.1% SDS at room temperature followed by 0.1×SSC/0.1% SDS at 50° C. then wrapped in plastic and exposed to Fuji X-ray film for autoradiography. Following removal of previous probes the filter was hybridised as above with a cDNA fragment derived by PCR amplification from a human skeletal muscle cDNA library (Clontech) corresponding to nucleotides 3816–4487 of clone KIAA0520 (GenBank/EMBL Accession Number AB011092) (26).

Ribonuclease protection assays were performed using a $^{32}$P-CTP labelled riboprobe synthesised by in vitro transcription (T7 RNA polymerase Riboprobe System, Promega) from a HindIII-linearised plasmid (pJP195; FIG. 1) partial human AC9 cDNA clone representing nucleotides 853–1167 according to the kit manufacturer (Ambion). Probe fragments protected from nuclease digestion following incubation with 5 µg total RNA samples from normal adult human brain obtained 4 h after death (JEB; Custodian, MRC Brain Bank, Western General Hospital, Edinburgh) or HEK293 cells (control) were resolved on a 6% denaturing acrylamide gel (8M Urea) and visualised by autoradiography.

In situ hybridisation was performed on 15 µm frozen sections from normal post mortem adult human brain obtained from the MRC Alzheimer Disease Brain Bank, Western General Hospital, Edinburgh—Professor Jeane E Bell, Custodian. Prepared sections were courtesy of Dr Celia Yates and Professor George Fink. $^{35}$S-labelled riboprobes were prepared by in vitro transcription from the human AC9 partial cDNA clone pJP195 (FIG. 18) using T7 (anti-sense) or SP6 (sense) RNA polymerase and used as previously described for mouse AC9 (Paterson et al, (1995) Biochem.

Biophys. Res. Commun. 214:1000–8; Rosie et al, (1990) J. Endocrinol. 124:285–9). Following hybridisation, brain sections were exposed to β-max autoradiogaphy film (Amersham-Pharmacia) for 2 weeks. The autoradiogram was developed and photographed under white light illumination.

Immunocytochemistry

HEK293 cells were plated on poly-D-lysine-coated coverslips and cultured as described above. Two to four days after plating, cells were washed in phosphate buffered saline (PBS) and fixed in 3% paraformaldehyde in PBS, pH 7.4, for 20 min at 4° C., treated with chilled (−20° C.) absolute methanol for 10 min (4° C.) and washed in 0.3 M glycine (3 times for 5 min) and 0.2% Triton X-100 (15 min) both in PBS at room temperature. Fixed cells were incubated for 18–24 h at 4° C. with affinity purified chick antibodies (1:400–1:500) raised against the C-terminus of mouse AC9 (Antoni et al, (1998) J. Neurosci. 18:9650–61). FITC-conjugated anti-chicken IgG (Jackson ImmunoRes.Lab.) was applied at 1:400 dilution for 1 hr at RT. After several washes in PBS specimens were mounted in CitiFluor (Sigma) and examined using a Leica TCS-NT confocal microscope. Specificity controls involved preincubation of the antibody with 10 μM antigen overnight at 4° C., after which immunocytochemistry was carried out as above.

Detection of Human AC9 by Immunoblotting

Membrane proteins were prepared from HEK293-derived cell lines as described previously (Antoni et al, (1998) supra). Approximately 10 μg membrane protein per lane were separated by SDS-PAGE and transferred by electroblotting on to PVDF membrane (Bio-Rad) at 220V in tank buffer (25 mMTris, 192 mM glycine, 0.036% SDS, 20% methanol) for 3 hrs at room temperature. PVDF membranes were blocked at room temperature by shaking in PBS containing 5% (w/v) skimmed milk powder and 0.1% Tween 20 for 2 hrs at room temperature, then washed 5×5 mins in PBS/0.1% Tween 20 before shaking incubation in PBS/0.1% Tween 20 containing primary antibody (rabbit anti-mouse AC9 N-terminus at 1:4,000 dilution or chicken anti-mouse AC9 C-terminus at 1:10,000 dilution) for 1 hr at room temperature. PVDF membranes were then washed as before and incubated in PBS/0.1% Tween 20 containing sheep anti-rabbit IgG-Horseradish peroxidase (HRP) conjugate (kindly provided by the Scottish Antibody Production Unit) at 1:8,000 dilution or goat anti-chicken IgY-HRP conjugate (Promega) at 1:10,000 dilution respectively) for 1 hour at room temperature then finally washed as above, exposed to reagents for development of chemiluminescence and visualised by exposure to Hyperfilm (ECL system, Amersham-Pharmacia, Aylesbury, UK). To confirm specificity, primary antisera were pre-incubated with mouse AC9-derived pentadeca-peptide antigens at final concentrations 1 μg/ml (C-terminal) and 0.1 μg/ml (N-terminal) for 20 & 45 mins respectively prior to probing of the PVDF membranes.

Results

Cloning and Sequencing of Human AC9 cDNA

Searching of human EST databases for similarity to mouse AC9 identifed two cDNA clones: IMAGE clone 166657 and HIBBC33, which were obtained as described in materials and methods. Oligonucleotide primers based on the DNA sequence of the inserts of these were used to construct a complete cDNA by PCR amplification from human cDNA libraries as described in materials and methods and outlined in FIG. 18. In the cDNA we describe (GenBank/EMBL Accession Number AJ133123) a short open reading frame (ORF) of 72 bp exists near the 5' end (263–334). However, the initiation codon of this ORF does not form part of a Kozak consensus sequence suggesting that translation may not be initiated although this remains to be confirmed. Downstream, a large ORF of 4059 bp is apparent, from 539–4597. This encodes a putative protein of 1353 amino acids, identical in length to the mouse AC9 protein. The deduced amino acid sequence of hAC9 reported here exhibits 92% sequence identity with the mouse AC9 protein and 86.7% identity at the nucleotide level. Structural features predicted from the amino acid sequence using the computer program TopPred 2 (von Heijne (1992) J. Mol. Biol. 225:487–494) are typical of membrane-associated mammalian adenylyl cyclases cloned to date, namely, two sets of six transmembrane regions (M1 and M2), each followed by a large cytoplasmic region (C1 and C2 respectively). These domains are conserved between the human and mouse AC9 proteins along with many motifs for potential post-translational modifications. With N and C termini localised intracellularly, the predicted topology of membrane-bound AC9 indicates conserved sites which may be suitable for modification include those for N-linked glycosylation, located extracellularly (residues 206, 955, 964), as well as intracellular sites suitable for tyrosine phosphorylation (residues 543, 1004, 1225) and serine/threonine phosphorylation by cAMP-dependent protein kinase (residues 373, 374), calmodulin-dependent protein kinase II (residues 1217), casein kinase II (residues 433, 582, 589, 691, 766, 1200) and protein kinase C (residues 27, 87, 112, 357, 365, 535, 620, 661, 762, 838, 1003, 1023, 1179, 1212, 1307).

Expression of Human AC9 Protein Detected by Immunocytochemical Analysis

Figure 19:
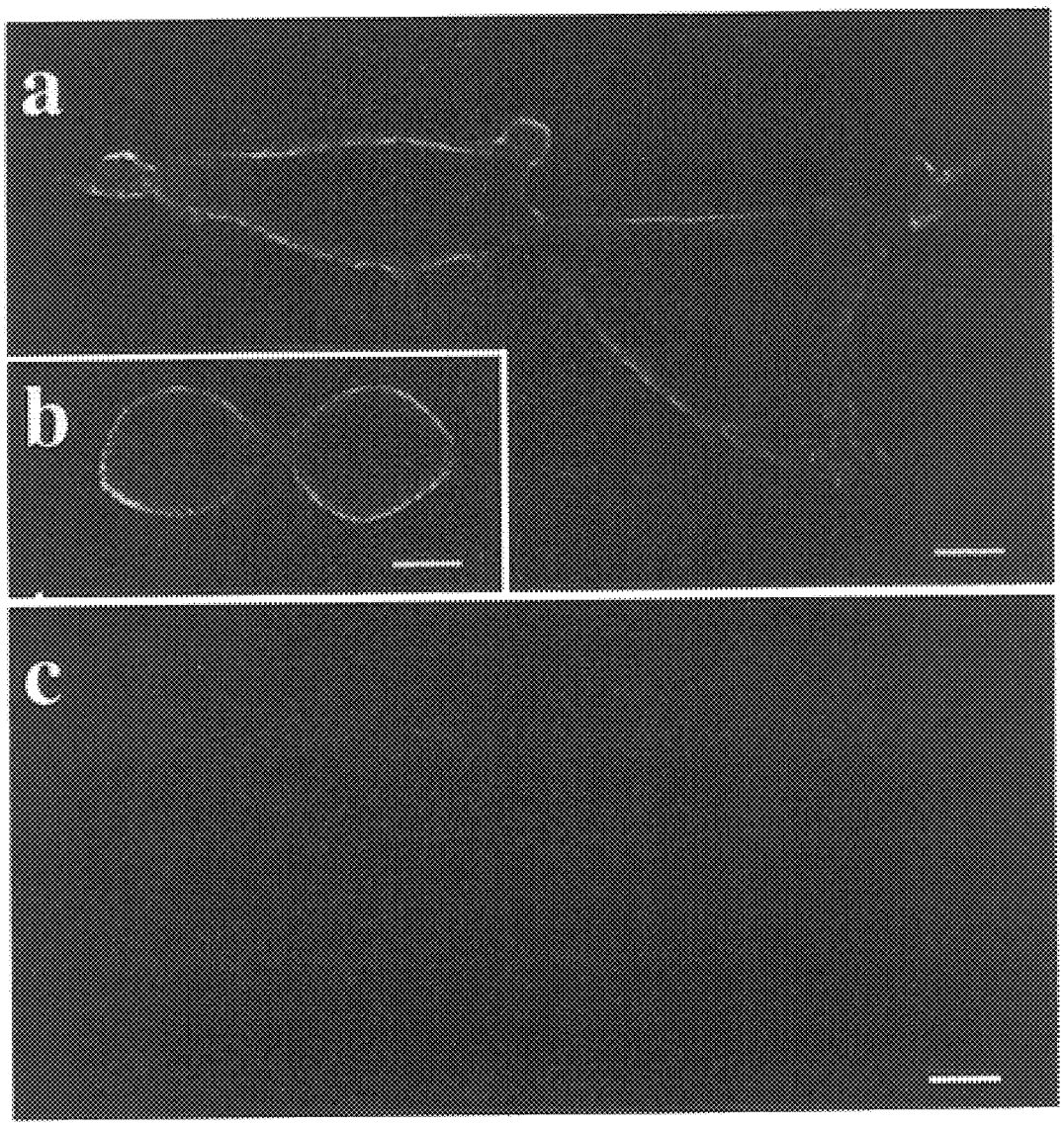

Immunocytochemical analysis using antisera raised against the C-terminus of the mouse AC9 protein revealed fluorescent labelling in HEK 293 cells stably transfected with cDNA encoding human AC9 (FIGS. 19a & b). No labelling was observed when the antiserum was pre-incubated with peptide antigen (FIG. 19c) indicating specific detection of human AC9 protein. A large majority of human AC9 expressed in HEK 293 cells appeared to be localised to the plasma membrane.

Detection of Multiple Human AC9 Polypeptides by Immunoblotting

Figure 20:
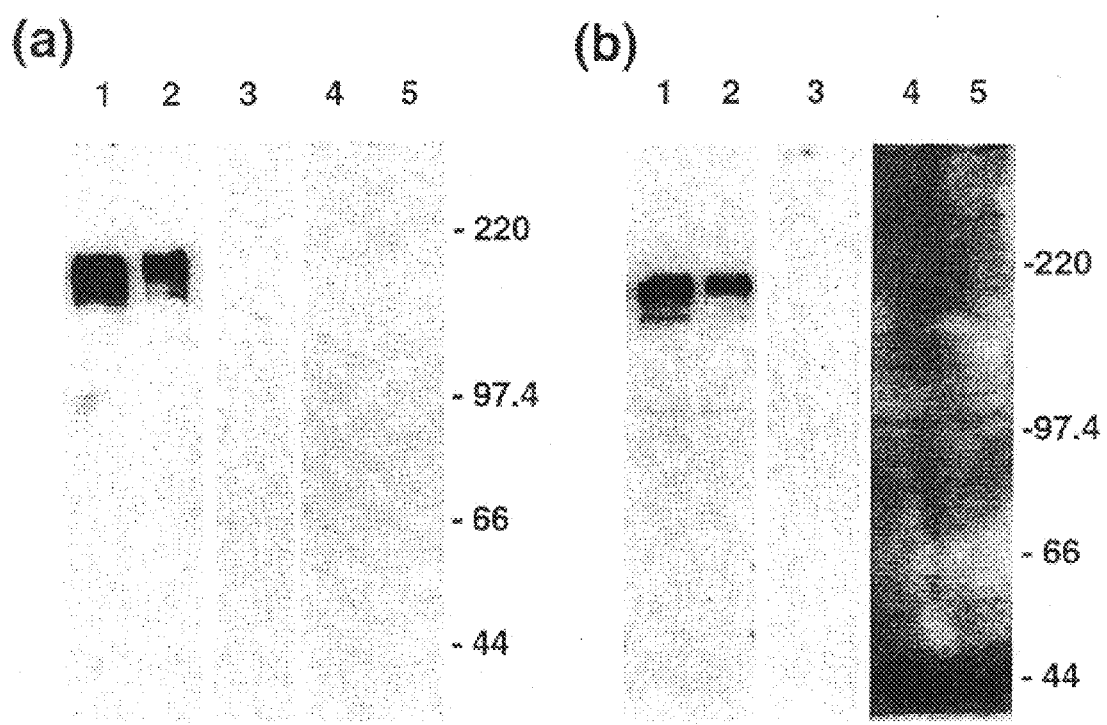

Immunoblotting of extracts from pcDNA3 and hAC9 stably transfected HEK293 cells resolved by SDS-polyacrylamide gel electrophoresis (PAGE) showed that hAC9 protein was expressed and specifically recognised by polyclonal antisera raised against peptides derived from the N- or the C-termini of mouse AC9 (FIG. 20). In each case, a broad immunoreactive band migrating between 160–180 kDa was detected, most probably attributable to post-translational modification by phosphorylation and/or N-glycosylation of the human AC9 protein in HEK 293. These observations confirm the predicted conservation of the sequences of the human and mouse AC9 at the N- and C-termini.

$Ca^{2+}$/Calcineurin Inhibition of cAMP Production by Human AC9

In the presence of phosphodiesterase inhibitors, the cAMP content of stably transfected HEK293 cell lines expressing human AC9 increased with time and this was reduced by the presence of $Ca^{2+}$ in the medium (FIG. 21a). No statistically significant increase of cAMP was observed in wild type HEK293 cells or HEK293 cell lines transfected with pcDNA3 vector alone. Similar data were obtained in cells treated in 5 μM 4-Br-A23187 containing medium (FIG. 21b) moreover, the inhibitory effect of $Ca^{2+}$ was blocked by FK506. L-685,818 and rapamycin, which both interact with FK506-binding-protein-12, but do not inhibit calcineurin (29), failed to block the inhibitory action of $Ca^{2+}$ on cAMP production (FIG. 21c). By contrast, cyclosporin A, which blocks calcineurin through a complex formed with cyclophilin A (Schreiber (1992) Cell 70:365–8) also abolished the effect of $Ca^{2+}$. These data indicate that the human AC9 expressed in HEK293 cells is able to synthesize cAMP and its activity is inhibited by $Ca^{2+}$ via calcineurin.

Tissue Distribution of Two Forms of Human AC9 mRNA

Figure 22:
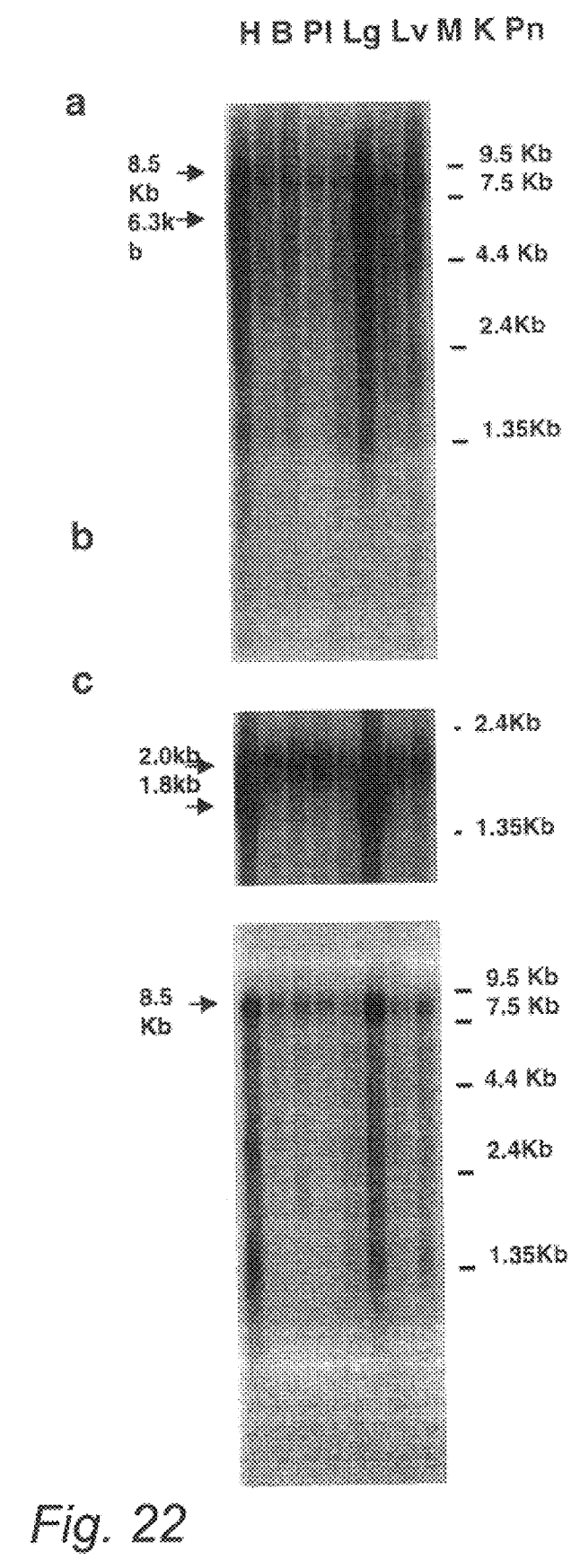

Analysis of hAC9 mRNA by Northern blotting (FIG. 22a) using a radio-labelled probe derived from the 5' end of the hAC9 cDNA (SmaI-MluI fragment; 528 bp) revealed hybridisation to a transcript of approximately 8.5 kb in all tissues represented, including brain, heart, skeletal muscle and pancreas. In addition, an approximately 6.3 kb mRNA was detected which appeared to be restricted to heart and skeletal muscle and gave a more intense signal than the 8.5 kb species. A human cDNA sequence (GenBank/EMBL Accession Number AB011092), described as part of a study reporting the predicted coding sequences of 100 cDNA clones isolated from human brain (Nagase et al, (1998) DNA Research 5:31–9), was retrieved by database searching and found to be identical to nucleotides 2900–5472 of the human AC9 cDNA sequence reported here but continues with a 3' untranslated region extended by 2234 bp. A cDNA fragment derived from this region used in hybridisation with the same MTN Northern blot detected the 8.5 kb human AC9 mRNA exclusively (FIG. 22c). These data are consistent with tissue-specific differential use of alternative polyadenylation signals on completion of mRNA transcription from the human AC9 gene. Subsequent searching of the GenBank/EMBL DNA sequence database for comparison of human AC9 cDNA 3'UTR sequences with the human AC9 gene locus (GenBank/EMBL Accession Number AC005736) confirmed the positions of alternative polyadenylation sites.

Expression of AC9 mRNA in Human Brain

Figure 23A:
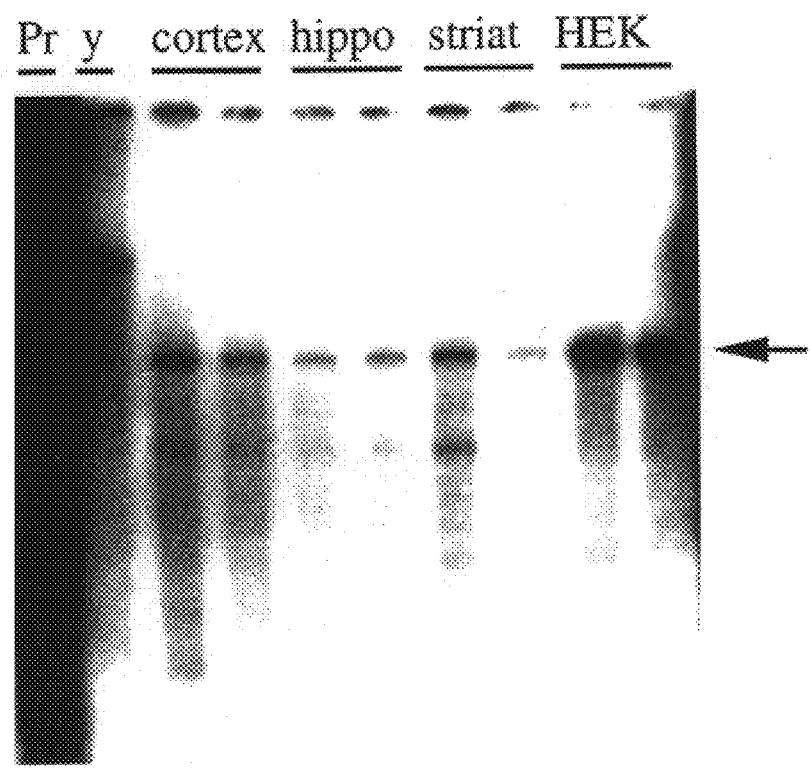
Figure 23B:
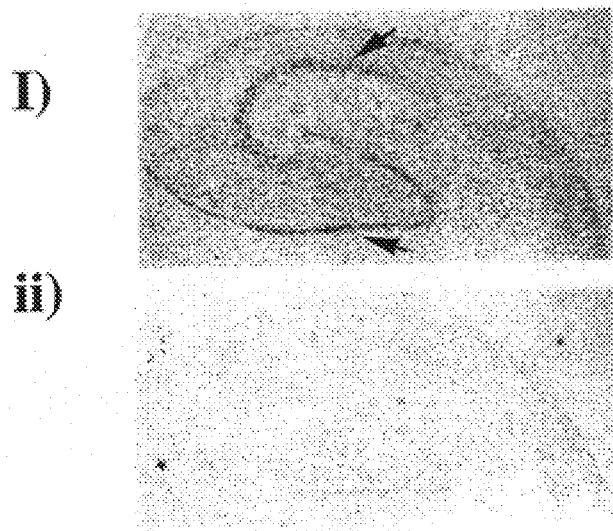

To address the potential role of AC9 within the human brain, expression of AC9 mRNA was investigated by ribonuclease protection assay of total RNA samples isolated from post-mortem hippocampus, cortex and striatum (FIG. 23a). Protection of the anti-sense AC9 riboprobe was observed in each of these regions of human brain, indicating expression of AC9 mRNA in areas important for learning and memory functions. AC9 mRNA distribution in human forebrain was also investigated by in situ hybridisation (FIG. 23b) where enriched expression was detected specifically in neurones of the dentate gyrus and hippocampal CA1–CA3 regions.

Discussion

We have isolated and sequenced a human cDNA encoding an adenylyl cyclase which, distinct from a recently reported predicted human AC9 polypeptide (Hacker et al, (1998) Genomics 50:97–104), encodes a homologue of murine AC9. Cyclic AMP production by this new human AC9 cDNA clone is inhibited by $Ca^{2+}$ through the protein phosphatase calcineurin. Analysis of the pattern of the expression of the novel AC9 mRNA indicates differential tissue specificity in the polyadenylation of transcripts. This has not been observed in the mouse and may provide an additional level of control in the regulation of AC9 expression in humans.

Confirmation of the Predicted Primary Sequence of the Human AC9 Protein

The human AC9 cDNA we have cloned predicts a polypeptide of the same length (1353 amino acid residues) as mouse AC9 and is 92% identical with the mouse AC9 polypeptide sequence. The novel human AC9 could be detected with anti-sera raised against the N- or the C-terminal regions of the mouse AC9 polypeptide sequence, confirming the predicted conservation of these regions between the two proteins. The 3' end of the cDNA reported here is identical to part of a 5'-truncated human AC9 cDNA clone KIAA0520 (Nagase et al, (1998) DNA Research 5:31–9). These sequences differ from that of another human AC9 cDNA clone reported recently by Hacker et al. who predicted an alternative C-terminus for the encoded polypeptide (Hacker et al, (1998) Genomics 50:97–104). By comparison of sequences, the prediction by Hacker et al. results from a 2 bp deletion causing a frame shift in the deduced amino acid sequence. Our data, therefore, predict and confirm an amino acid sequence for human AC9 which is distinct from that reported for a previously isolated clone of the human enzyme but which is conserved with mouse AC9.

Inhibition of Human AC9 Activity by $Ca^{2+}$/Calcineurin

Stably transfected HEK293-derived cell lines which overexpress human AC9 showed a marked increase in cAMP production in comparison to wild type or pcDNA3-transfected control cells. The synthesis of cAMP was reduced by intracellular $Ca^{2+}$ concentrations in the range of 100–150 nM which is similar to previous data with HEK293 cells overexpressing mouse AC9 (Paterson et al, Biochem. Biophys. Res. Commun. 214:1000–8; Antoni et al, (1998) J. Neurosci. 18:9650–61). The inhibitory effect of $Ca^{2+}$ was blocked by FK506 or cyclosporin A, which are two mechanistically distinct blockers of the $Ca^{2+}$/calmodulin activated protein phosphatase calcineurin (Sabatini et al, (1992) Cell 70:365–8). In the presence of FK506 or cyclosporin A, cAMP production in hAC9 expressing cells was enhanced. Furthermore, application of L685,818 or rapamycin had no effect on cAMP production. The results indicate that the activity of human AC9, like mouse AC9 (Paterson et al, Biochem. Biophys. Res. Commun. 214:1000–8; Antoni et al, (1995) J. Biol. Chem. 270:28055–61; Antoni et al, (1998) J. Neurosci. 18:9650–61), is under inhibitory control by $Ca^{2+}$ which is mediated by calcineurin. The lack of $Ca^{2+}$ inhibition of AC9 observed by others may be due to analysis in insect cells (Premont et al, (1996) J. Biol. Chem. 271:13900–7) which may lack the necessary co-factors or may be attributable to a feature of the cDNA and/or transfected cell clone analysed (Hacker et al, (1998) Genomics 50:97–104). Immunological detection of multiple human AC9 polypeptides may represent differential post-translational modifications in HEK293 cells. Correlation of these observations with multiple phosphorylation or other post-translational modifications of human AC9 protein remains to be addressed. Immunocytochemical analysis shown in FIG. 19 suggests that the great majority of human AC9 polypeptides expressed in HEK 293 cells are localised to the plasma membrane.

Differential Human AC9 mRNA Expression

In similarity with the mouse (Premont et al, (1996) J. Biol. Chem. 271:13900–7) and in agreement with a recent study of another human AC9 cDNA clone (Hacker et al, (1998) Genomics 50:97–104), a broad pattern of expression was observed for an 8.5 kb AC9 mRNA in human brain and peripheral tissues when assayed by Northern blotting using a probe derived from the 5' end of the cDNA we have isolated. In the present study, a 6.3 kb human AC9 mRNA also detected by this probe appeared to be restricted to human heart and skeletal muscle. Previously, however, a probe representing a 5'-truncated human AC9 cDNA detected a 6.3 kb transcript at high levels in skeletal muscle, at low levels in kidney, liver, lung and placenta but which was apparently absent from heart (Hacker et al, (1998)

supra). Although the probes used in these two studies overlap by approximately 100 bp near the 5' end of the ORF, the hybridisation conditions used may mean that these probes would be capable of detecting differentially spliced human AC9 mRNA transcripts if an intron/exon junction were located within this region. Lack of detection of the 6.3 kb mRNA in heart may potentially reflect mRNA splicing of upstream exons, detectable by the 5' probe, to alternative downstream exons. Similarly, it is possible that hybridisation to the 6.3 kb transcript by the 5'-truncated 4.65 kb partial cDNA probe reflects the presence of alternative 5'-end sequences not detectable by the 5' probe used in this study. However, comparison of our cDNA sequence with human AC9 genomic sequence available in the GenBank/EMBL database (Accession Number AC005736) indicates no evidence of mRNA splicing in this region. The β-actin control in our Northern blotting analysis suggests the presence of proportionally greater amounts of heart and skeletal muscle mRNAs. Therefore, it is possible that the 6.3 kb AC9 mRNA was present in other tissues but not at a level detectable under the conditions we have used and that expression of this transcript is not necessarily restricted to heart and skeletal muscle as our results suggest. A probe derived from the extended 3' untranslated region of the 8.5 kb human AC9 transcript which is present in the cDNA clone KIAA0520 exclusively detected the 8.5 kb mRNA in northern blotting. This indicates the use of alternative polyadenylation signals within the human AC9 gene to be the mechanism accounting for the observation of two mRNAs. Polyadenylation of many eukaryotic mRNAs is understood to contribute to inhibition of mRNA degradation and/or potentiate mRNA translation, reviewed in (Wickers et al, (1997) Curr. Opin. Genet. Dev. 7:220–32). In addition, 5' and particularly 3' untranslated regions (UTRs) have been found to be important for the regulation of mRNA translation, stability and localisation, reviewed in (Wickers et al, (1997) supra; Jackson et al, (1997) Curr. Opin. Genet. Dev. 7:233–41), most significantly during development, reviewed in (Curtis et al, (1995) Cell 81:171–8; Seydoux (1996) Curr. Opin. Genet. Dev. 6:555–61; Macdonald et al, (1996) Curr. Opin. Genet. Dev. 6:403–7). The spatial and/or temporal distribution of trans-acting factors interacting with cis elements within 3'UTRs and form a complex with the 5'UTR and associated translation initiation factors has been proposed a molecular mechanism for the control of gene expression by regulation of translation efficiency (Wickers et al, (1997) supra). Although sequences within the 3'UTRs of human and mouse AC9 mRNAs are highly conserved, the 3'UTRs of human AC9 transcripts extend beyond that of the mouse with the 8.5 kb mRNA possessing considerable more 3' untranslated sequence than the 6.3 kb message. Although the functional significance of 3'UTRs in AC9 mRNAs remains to be addressed but may be subject to differential post-transcriptional regulation providing an additional mechanism of control at the level of mRNA stability and/or translational efficiency facilitating differential regulation of AC9 expression which may be relevant for the appropriate function of the enzyme in humans.

In cardiac myocytes, adenylyl cyclase VI (AC6) expression has been shown to be limiting for transmembrane β-adrenergic signal transduction. Furthermore, all currently known cardiac adenylyl cyclases are under inhibitory control by $Ca^{2+}$. Thus precise control of cAMP levels mediated through regulation of AC expression and control of AC activity appears essential for optimal cardiac function (Gao et al, (1998) PNAS U.S.A. 95:1038–43). Alterations to the levels of AC expression in heart, including AC9, may therefore contribute to an impairment of cardiac function related to reduction or loss of cAMP production. A role for post-transcriptional regulation in the control of adenylyl cyclase expression has recently been suggested from studies of ACVIII (AC8) (Muglia et al, (1999) J. Neurosci. 19:2051–8) which have revealed conservation of large 5'UTRs of AC8 mRNAs from mouse, rat and human.

Detection of AC9 mRNA by ribonuclease protection assay revealed expression in hippocampus, neocortex and striatum of post-mortem human brain. In situ hybridisation analysis revealed enriched expression of AC9 mRNA in hippocampus and indicated a neuronal localisation in projection neurones of the CA1–CA3 regions. The $Ca^{2+}$/calmodulin activated protein phosphatase calcineurin, which regulates AC9 activity, is also highly abundant in these regions (Winder et al, (1998) Cell 92:25–37). These findings are likely to be relevant to the function of AC9 in brain, particularly in hippocampus, where precise control of $Ca^{2+}$ and cAMP levels is pivotal for synaptic plasticity and suggests potential involvement in functions important for cognitive behaviour (Mons et al, (1995) Trends in Neurosci. 18:536:42; Xia et al, (1997) Curr. Opin. Neurobiol. 7:391–6; Antoni et al, (1998) J. Neurosci. 18:9650–61; Winder et al, (1998) Cell 92:25–27; Mons et al, (1998) Life Sciences 62:1647–52).

Isolation of a human AC9 has enabled our characterisation of the enzyme, allowing comparison with that of the mouse. Differential usage of polyadenylation signals within the gene providing the potential for alternative mRNA post-transcriptional regulation has been identified as a distinct feature of human AC9 likely to be important for precise control of expression. In similarity with mouse AC9, cAMP production by human AC9 is under inhibitory control by $Ca^{2+}$/calcineurin. Post-translational modifications of the human AC9 protein, including possible phosphorylation, now require characterisation and their potential functional consequences investigated. The physiological function of AC9 and its potential involvement in human disease, particularly in view of its broad expression pattern, are complex issues to address. Although important differences have been described, many features are common to the human and murine enzymes. The production of mouse models may, therefore, be useful in the investigation of specific functions of AC9 in vivo.

TABLE I

Effect of pretreatment with FK506 (1 μmol/l) and BAPTA/AM (20 μmol/l) on cAMP accumulation induced by β-adrenergic stimulation in AtT20 cells. Data are means ±SEM, n = 4/group. IBMX 0.5 mmol/l and rokpram 0.1 mmol/l present throughout. nd - not determined, previous studies showed that there is no effect of either preincubation protocol on basal cAMP levels.

| Isoproterenol | Pretreatment | | |
|---|---|---|---|
| (nmol/l) | None | FK506 | BAPTA/AM |
| None | 0.43 ± 04 | nd | nd |
| 0.4 | 0.7 ± 0.04 | 0.94 ± 0.09 | 0.96 ± 0.06 |
| 2 | 2.0 ± 0.08 | 3.3 ± 0.7 | 3.6 ± 0.6 |
| 10 | 9.5 ± 0.33 | 15.3 ± 2.5 | 11.4 ± 0.9 |
| 100 | 19.5 ± .5 | 31.4 ± 1.9 | 35.5 ± 3.4 |
| 1000 | 32.1 ± 0.5 | 45.3 ± 9 | 46.9 ± 9 |

TABLE II

PCR protocols for 5' RACE base cDNA cloning of AC from AtT20 cell total RNA

Reaction using primers 2 or 3 with UAP

| | | |
|---|---|---|
| 1 cycle | 95° C. | 5 min |
| | 80° | 5 min (Taq polymerase added) |
| 5 cycles | 94° C. | 45 sec |
| | 55° C. | 30 sec |
| | 72° C. | 90 sec |
| 30 cycles | 94° C. | 45 sec |
| | 57° C. | 30 sec |
| | 72° C. | 90 sec |
| 1 cycle | 72° C. | 10 min |

Reaction using primer 5 with UAP:

| | | |
|---|---|---|
| 1 cycle | 95° C. | 5 min |
| | 80° C. | 5 min (Taq polymerase added) |
| 35 cycles | 94° C. | 45 sec |
| | 55° C. | 30 sec |
| | 72° C. | 90 sec |
| 1 cycle | 72° C. | 10 min |

Reaction using primer 6 with UAP

| | | |
|---|---|---|
| 1 cycle | 95° C. | 5 min |
| | 80° C. | 5 min (Taq polymerase added) |
| 35 cycles | 94° C. | 60 sec |
| | 58° C. | 60 sec |
| | 72° C. | 90 sec |
| 1 cycle | 72° C. | 10 min |

TABLE III

Potential sites of phosphorylation by common S/T protein kinases in AC

A KINASE:
Motif: RXS Position

| | |
|---|---|
| RAS | 85 |
| RES | 597 |
| RTS | 763 |
| RSS | 919 |

Motif: RXXS

| | | |
|---|---|---|
| RASS | 85 | (SEQ ID NO: 15) |
| RVDS | 201 | (SEQ ID NO: 16) |
| RSRS | 304 | (SEQ ID NO: 17) |
| RESS | 597 | (SEQ ID NO: 18) |
| RPAS | 972 | (SEQ ID NO: 19) |
| RVLS | 1213 | (SEQ ID NO: 20) |

C KINASE
Motif: (S/T)X(K/R)
S preferred with hydrophobic AA on COOH side of S
(23/37 of known sites are like this)

| | |
|---|---|
| SIR | 837 |
| SMR | 1022 |
| SWR | 1310 |
| SVK | 356 |
| SVR | 27 |
| SYR | 761 |
| SYR | 1002 |
| SYR | 1211 |
| TAK | 534 |
| TLR | 187 |
| TVK | 619 |

TABLE III-continued

Potential sites of phosphorylation by common S/T protein kinases in AC

Motif (K/R)XX(S/T)
(S preferred with hydrophobic AA)

| | | |
|---|---|---|
| KIKTI | 1105 | (SEQ ID NO: 21) |
| KTATL | 266 | (SEQ ID NO: 22) |
| KISTL | 436 | (SEQ ID NO: 23) |
| KKSSI | 370 | (SEQ ID NO: 24) |
| KEDSL | 732 | (SEQ ID NO: 25) |
| KFDSM | 94 | (SEQ ID NO: 26) |
| KIQSM | 1019 | (SEQ ID NO: 27) |
| RPASL | 972 | (SEQ ID NO: 28) |

CASEIN KINASE II:
Motif: 3 acidic aa-s atter phosphorylation site are a strong indication (*), highly S preferring

| | | |
|---|---|---|
| SCAEA | 581 | (SEQ ID NO: 29) |
| SGFEV | 588* | (SEQ ID NO: 30) |
| SLCEI | 690 | (SEQ ID NO: 31) |
| SYQEE | 765 | (SEQ ID NO: 32) |
| SEFET | 885* | (SEQ ID NO: 33) |
| SWREP | 1310 | (SEQ ID NO: 34) |
| TTSET | 261 | (SEQ ID NO: 35) |
| TKCEK | 432 | (SEQ ID NO: 36) |
| TKCEK | 432 | |
| TGVEC | 1199 | (SEQ ID NO: 37) |

CAM KINASE II:
Motif: XRXX(S/T) Position

| | | |
|---|---|---|
| ERASS | 84 | (SEQ ID NO: 38) |
| GRVDS | 200 | (SEQ ID NO: 39) |
| VRSRS | 303 | (SEQ ID NO: 40) |
| SRESS | 596 | (SEQ ID NO: 41) |
| RRPAS | 971 | (SEQ ID NO: 42) |
| YRVLS | 1212 | (SEQ ID NO: 43) |
| KRHAT | 358 | (SEQ ID NO: 44) |
| IREKT | 719 | (SEQ ID NO: 45) |
| SRMDT | 1194 | (SEQ ID NO: 46) |
| GRSPT | 1270 | (SEQ ID NO: 47) |

TABLE IV

Inhibition by 1 $\mu$mol/l FK506 of the effect of extracellular calcium ions on 10 nmol/l CRF-induced cAMP formation in calcium-depleted AtT20 cells in the presence of 0.5 mmol/l IBMX (see Legend to Fig 1 and Example 1 for methods). Data are means ± SEM, pmol/well, n = 6/group. 2-way ANOVA gave a significant ($P < 0.05$) interaction between extracellular calcium and FK506. Unstimulated cAMP levels were 0.5 ± 0.06 pmol/l.

| Extracellular free [$Ca^{2+}$] [mmol/l] | Vehicle | FK506 |
|---|---|---|
| 0 | 12.1 ± 0.16 | 10.3 ± 0.10 |
| 0.5 | 10.4 ± 0.96 | 10.0 ± 0.11 |
| 1.0 | 9.7 ± 0.10 | 10.4 ± 0.10 |
| 1.5 | 6.2 ± 0.04 | 11.3 ± 0.13 |
| 2.0 | 5.2 ± 0.54 | 9.5 ± 0.11 |

What is claimed is:

1. An isolated polynucleotide comprising a nucleotide sequence as set out in SEQ ID NO: 98.

2. A recombinant polynucleotide construct comprising a polynucleotide as claimed in claim 1.

3. A vector comprising a polynucleotide as claimed in claim 1.

4. A host cell transformed with a vector as claimed in claim 3.

5. A host cell as claimed in claim 4 which is derived from the Human Embryonic Kidney Cell line 293.

* * * * *